United States Patent
Martin et al.

(10) Patent No.: US 12,146,874 B2
(45) Date of Patent: *Nov. 19, 2024

(54) MICROTENTACLE IMAGING IN PATIENT TUMOR SAMPLES

(71) Applicant: University of Maryland, Baltimore, Baltimore, MD (US)

(72) Inventors: Stuart S. Martin, Severna Park, MD (US); Christopher Jewell, Silver Spring, MD (US); James Andorko, Delran, NJ (US); Elisabeth Sooklal, Reisterstown, MD (US); Rebecca Whipple Bettes, Elkridge, MD (US); Kristi Chakrabarti, Silver Spring, MD (US)

(73) Assignees: UNIVERSITY OF MARYLAND, BALTIMORE, Baltimore, MD (US); UNIVERSITY OF MARYLAND, COLLEGE PARK, College Park, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/301,587

(22) PCT Filed: Apr. 3, 2015

(86) PCT No.: PCT/US2015/024207
§ 371 (c)(1),
(2) Date: Oct. 3, 2016

(87) PCT Pub. No.: WO2015/153948
PCT Pub. Date: Oct. 8, 2015

(65) Prior Publication Data
US 2017/0184568 A1   Jun. 29, 2017

Related U.S. Application Data

(60) Provisional application No. 61/974,753, filed on Apr. 3, 2014, provisional application No. 62/068,034, filed on Oct. 24, 2014.

(51) Int. Cl.
*G01N 33/50* (2006.01)
*G01N 21/95* (2006.01)
*G01N 33/574* (2006.01)
*G02B 21/00* (2006.01)

(52) U.S. Cl.
CPC ......... *G01N 33/5026* (2013.01); *G01N 21/95* (2013.01); *G01N 33/50* (2013.01); *G01N 33/574* (2013.01); *G02B 21/0028* (2013.01); *G01N 2800/7028* (2013.01)

(58) Field of Classification Search
CPC ...... G01N 21/95; G01N 33/50; G01N 33/574; G01N 2800/7028; G02B 21/0028
See application file for complete search history.

(56) References Cited

U.S. PATENT DOCUMENTS

| | | | |
|---|---|---|---|
| 8,193,238 B2 | 6/2012 | Martin | |
| 2009/0137473 A1 | 5/2009 | Martin | |
| 2013/0225656 A1* | 8/2013 | Iragavarapu-Charyulu | G01N 33/6893 |
| | | | 514/44 A |
| 2014/0093953 A1 | 4/2014 | Ingram | |
| 2014/0093962 A1 | 4/2014 | Ingram et al. | |
| 2014/0094383 A1 | 4/2014 | Lee | |
| 2016/0097769 A1 | 4/2016 | Martin | |

FOREIGN PATENT DOCUMENTS

| | | |
|---|---|---|
| WO | 2003/035278 A1 | 5/2003 |
| WO | 2007104011 A2 | 9/2007 |
| WO | 20080144506 A1 | 11/2008 |
| WO | 2012162345 A1 | 11/2012 |
| WO | 2016/064584 A2 | 4/2016 |

OTHER PUBLICATIONS

Bockhorn et al. "Active versus passive mechanisms in metastasis: do cancer cells crawl into vessels, or are they pushed?" May 2007, Lancet Oncology: vol. 8, No. 5: 444-448. (Year: 2007).*
DeRose et al. "Patient-Derived Models of Human Breat Cancer: Protocols for In Vitro and In Vivo Applications in Tumor Biology and Translational Medicine" Mar. 2013, Current Protocols in Pharmacology, 14.23.1-14.23.43. (Year: 2013).*
1 Extended European Search Report from European Appl. No. 15852876, mailed on Feb. 20, 2018.
Matrone et al., Metastatic breast tumors express increased tau, which promotes microtentacle formation and the reattachment of detached breast tumor cells, Oncogene, 29:3217-3227 (2010).
Whipple et al., Detyrosinated microtubule protrusions in suspended mammary epithelial cells promote reattachment, Experimental Cell Research, 313:1326-1336 (2007).
Charpentier et al., Curcumin targets breast cancer stem-like cells with microtentacles that persist in mammospheres and promote reattachment, Cancer Res, 74:1250-1260 (2014).
Charpentier et al., Interplay of Stem Cell Characteristics, EMT, and Microtentacles in Circulating Breast Tumor Cells, Cancers, 5:1545-1565 (2013).
International Search Report from Appl. No. PCT/2015/024207, U.S. Patent and Trademark Office, mailed on Oct. 19, 2015.
Matron el al., Microtentacles Tip the Balance of Cytoskeletal Forces in Circulating Tumor Cells, Cancer Res, 70:7737-7741 (2010).

(Continued)

*Primary Examiner* — Teresa E Knight
(74) *Attorney, Agent, or Firm* — Nevrivy Patent Law Group P.L.L.C.

(57) ABSTRACT

The present invention provides a method for imaging microtentacles on isolated, living, non-adherent primary tumor cells from a cancer subject comprising: i) obtaining one or more living, non-adherent primary tumor cells that has been isolated from a solid tumor from the subject; and ii) imaging the one or more living, non-adherent primary tumor cells and detecting the microtentacles.

36 Claims, 24 Drawing Sheets

(56) References Cited

OTHER PUBLICATIONS

Charpentier, Clinical Studies Co-Investigator UMGCC-0902: A Feasibility Study to Identify Microtentacles and Stem Cell Phenotype of Circulating Cancer Cells in Metastatic Breast Cancer Patients August 2010-Present, Biochemistry and Molecular Biology, 1-125 (2014).
European Official Communication from Appl. No. 15772640.7, European Patent Office, mailed on Oct. 4, 2017.
Kidambi et al., Controlling Primary Hepatocyte Adhesion and Spreading on Protein-Free Polyelectronlyte Multilayer Films, Journal of American Chemical Society, 126:16286-16287 (2004).
Aceto et al., Circulating tumor cell clusters are oligoclonal precursors of breast cancer metastasis, Cell, 158:1110-1122 (2014).
Adams et al., Highly Efficient Circulating Tumor Cell Isolation from Whole Blood and Label-Free Enumeration Using Polymer-Based Microfluidics with an Integrated Conductivity Sensor, Journal of the American Chemical Society, 130:8633-8641 (2008).
Balzer et al., Anti-mitotic chemotherapeutics promote adhesive responses in detached and circulating tumor cells, Breast Cancer Res Treat, 121:65-78 (2010).
Bhandary et al., ROCK inhibition promotes microtentacles that enhance reattachment of breast cancer cells, Oncotarget, 6:6251-6266 (2015).
Brouquet et al., A model of primary culture of colorectal cancer and liver metastasis to predict chemosensitivity, The Journal of Surgical Research, 166:247-254 (2011).
Chambers et al., Dissemination and Growth of Cancer Cells in Metastatic Sites, Nat Rev Cancer, 2:563-572 (2002).
Cristofanilli et al., Circulating Tumor Cells, Disease Progression, and Survival in Metastatic Breast Cancer, The New England Journal of Medicine, 351:781-791 (2004).
Cristofanilli et al., Circulating Tumor Cells: A Novel Prognostic Factor for Newly Diagnosed Metastatic Breast Cancer, J Clin Oncol, 23:1420-1430 (2005).
Cristofanilli et al., Circulating tumor cells in breast cancer: Advanced tools for "tailored" therapy?, Proc Natl Acad Sci USA, 103:17073-17074 (2006).
De Bono et al., Circulating Tumor Cells Predict Survival Benefit from Treatment in Metastatic Castration-Resistant Prostate Cancer, Clin Cancer Res, 14:6302-6309 (2008).
De Rose et al., Tumor grafts derived from women with breast cancer authentically reflect tumor pathology, growth, metastasis and disease outcomes, Nat Med, 17:1514-1520 (2011).
De Rose et al., Patient-derived models of human breast cancer: protocols for in vitro and in vivo applications in tumor biology and translational medicine, Current protocols in pharmacology / editorial board, SJ Enna Chapter 14: Unit 14 23 (2013).
Flessner et al., Degradable polyelectrolyte multilayers that promote the release of siRNA, Langmuir: the ACS journal of surfaces and colloids, 27:7868-7876 (2011).
Hekimian et al., Epithelial Cell Dissemination and Readhesion: Analysis of Factors Contributing to Metastasis Formation in Breast Cancer, ISRN Oncol, Article ID 601810, 8 pages (2012).
Kato et al., Immobilized culture of nonadherent cells on an oleyl poly(ethylene glycol) ether-modified surface, Biotechniques, 35:1014-1018, 1020-1021 (2003).
Li et al., Acoustic separation of circulating tumor cells, Proceedings of the National Academy of Sciences, 112:4970-4975 (2015).
Kohli et al., Arrays of lipid bilayers and liposomes on patterned polyelectrolyte templates, J Colloid Interface Sci, 301: 461-469 (2006).
Krebs et al., Evaluation and Prognostic Significance of Circulating Tumor Cells in Patients With Non-Small-Cell Lung Cancer, J Clin Oncol, 29:1556-1563 (2011).
Jewell et al., Release of Plasmid DNA from Intravascular Stents Coated with Ultrathin Multilayered Polyelectrolyte Films, Biomacromolecules 7:2483-2491 (2006).
Jewell et al., Multilayered polyelectrolyte films promote the direct and localized delivery of DNA to cells, Journal of controlled release, 106:214-223 (2005).
Jewell et al., Multilayered polyelectrolyte assemblies as platforms for the delivery of DNA and other nucleic acid-based therapeutics, Advanced drug delivery reviews, 60:979-999 (2008).
Joosse et al., Biology, detection, and clinical implications of circulating tumor cells, EMBO Mol Med, 7:1-11 (2015).
Mendelsohn et al., Rational Design of Cytophilic and Cytophobic Polyelectrolyte Multilayer Thin Films, Biomacromolecules, 4:96-106 (2003).
Mitchell et al., Surfactant Functionalization Induces Robust, Differential Adhesion of Tumor Cells and Blood Cells to Charged Nanotube-Coated Biomaterials Under Flow, Biomaterials, 56:179-186 (2015).
O'Brien et al., The effect of pore size on cell adhesion in collagen-GAG scaffolds, Bio materials, 26:433-441 (2005).
Pachmann et al., Monitoring the Response of Circulating Epithelial Tumor Cells to Adjuvant Chemotherapy in Breast Cancer Allows Detection of Patients at Risk of Early Relapse, J Clin Oncol, 26:1208-1215 (2008).
Pantel et al., The biology of circulating tumor cells, Oncogene, 35:1216-1224 (2016).
Park et al., Full Surface Embedding of Gold Clusters on Silicon Nanowires for Efficient Capture and Photothermal Therapy of Circulating Tumor Cells, Nano Letters, 12:1638-1642 (2012).
Plaks et al., Circulating Tumor Cells, Science, 341:1186-1188 (2013).
Pierga et al., CirculatingTumor Cell Detection Predicts Early Metastatic Relapse After Neoadjuvant Chemotherapy in Large Operable and Locally Advanced Breast Cancer in a Phase II Randomized Trial, Clin Cancer Res, 14:7004-7010 (2008).
Reategui, Tunable Nanostructured Coating for the Capture and Selective Release of Viable Circulating Tumor Cells, Adv Mater, 27:1593-1599 (2015).
Rhee et al., Patterned cell culture inside microfluidic devices, Lab on a Chip, 5:102-107 (2005).
Richert et al., Improvement of Stability and Cell Adhesion Properties of Polyelectrolyte Multilayer Films by Chemical Cross-Linking, Biomacromolecules, 5:284-294 (2004).
Sarioglu et al., A microfluidic device for label-free, physical capture of circulating tumor cell-clusters, Nat Meth, 12:685-691 (2015).
Saurer et al., Polyelectrolyte multilayers promote stent-mediated delivery of DNA to vascular tissue, Biomacromolecules, 14:1696-1704 (2013).
Selden et al., Chemically programmed cell adhesion with membrane-anchored oligonucleotides, Journal of the American Chemical Society, 134:765-768 (2012).
Slade et al., Comparison of bone marrow, disseminated tumour cells and blood-circulating tumour cells in breast cancer patients after primary treatment, Br J Cancer, 100:160-166 (2009).
Stoler et al., Breast epithelium procurement from stereotactic core biopsy washings: flow cytometry-sorted cell count analysis, Clin Cancer Res, 8:428-432 (2002).
Stott et al. Isolation of circulating tumor cells using a microvortex-generating herringbone-chip, Proceedings of the National Academy of Sciences, 107:18392-18397 (2010).
Sun et al., Assembly of Multilayered Films Using Well-Defined, End-Labeled Poly(acrylic acid): Influence of Molecular Weight on Exponential Growth in a Synthetic Weak Polyelectrolyte System, Langmuir, 23:8452-8459 (2007).
Yamaguchi et al., Photocontrollable Dynamic Micropatterning of Non-adherent Mammalian Cells Using a Photocleavable Poly(ethylene glycol) Lipid, Angewandte Chemie, Supporting Information, (2011).
Takao et al., Enumeration, characterization, and collection of intact circulating tumor cells by cross contamination-free flow cytometry. Cytometry Part A:journal of the International Society for Advancement of Cytometry, 79:107-117 (2011).
Vitolo et al., Loss of PTEN induces microtentacles through PI3K-independent activation of cofilin, Oncogene, 32(17): doi:10.1038/onc.2012.234 (2013).

(56) References Cited

OTHER PUBLICATIONS

Wang et al., Enrichment of Prostate Cancer Stem-Like Cells from Human Prostate Cancer Cell Lines by Culture in Serum-Free Medium and Chemoradiotherapy, International journal of biological sciences, 9:472-479 (2013).
Whipple et al., Vimentin filaments support extension of tubulin-based microtentacles in detached breast tumor cells, Cancer Research, 68:5678-5688 (2008).
Zhang et al., Forming Lipid Bilayer Membrane Arrays on Micropatterned Polyelectrolyte Film Surfaces, Chemistry A European Journal, 19:9059-9063 (2013).
Whipple et al., Epithelial-to-mesenchymal transition promotes tubulin detyrosination and microtentacles that enhance endothelial engagement, Cancer Res, 70:8127-8137 (2010).
Whipple et al., Parthenolide and costunolide reduce microtentacles and tumor cell attachment by selectively targeting detyrosinated tubulin independent from NF-κB inhibition, Breast Cancer Research, 15:R83 (2013).
Yamahira et al., Collagen Surfaces Modified with Photo-Cleavable Polyethylene Glycol-Lipid Support Versatile Single-Cell Arrays of Both Non-adherent and Adherent Cells, Macromol Biosci, 14:1670-1676 (2014).
Yamaguchi et al., Photocontrollable Dynamic Micropatterning of Non-adherent Mammalian Cells Using a Photocleavable Poly(ethylene glycol) Lipid, Angew Chem Int Ed Engl, 51:128-131(2012).
Yang et al., New class of ultrathin, highly cell-adhesion-resistant polyelectrolyte multilayers with micropatterning capabilities, Biomacromolecules, 4:987-994 (2003).
Yang et al., Cellular interactions on nano-structured polyelectrolyte multilayers, Colloids and Surfaces A: Physicochemical and Engineering Aspects, 313-314:526-529 (2008).
Yoon et al., Local anesthetics inhibit kinesin motility and microtentacle protrusions in human epithelial and breast tumor cells, Breast Cancer Res Treat, 129:691-701 (2011).
Yoon et al., Circulating tumor cells: approaches to isolation and characterization, Breast Cancer Res Treat, 129:691-701 (2011).
Yu et al., Circulating tumor cells: approaches to isolation and characterization, JCB: Review, 192:373-382 (2011).
Yu et al., Ex vivo culture of circulating breast tumor cells for individualized testing of drug susceptibility, Science, 345:216-220 (2014).
Yu et al., Circulating Breast Tumor Cells Exhibit Dynamic Changes in Epithelial and Mesenchymal Composition, Science, 339:580-584 (2013).
Zanina et a., Differences in Caco-2 Cell Attachment, Migration on Collagen and Fibronectin Coated Polyelectrolyte Surfaces, Biotechnol Bioproc E, 18:144-154 (2013).
Zheng et al., Precise Control of Cell Adhesion by Combination of Surface Chemistry and Soft Lithography, Advanced Healthcare Materials, 2:95-108 (2013).
Chippada et al., A Nonintrusive Method of Measuring the Local Mechanical Properties of Soft Hydrogel Using Magnetic Microneedles, Journal of Biomechanical Engineering, 131:021014-1-12 (2009).
Liu et al., Silica nanoparticle supported lipid bilayers for gene delivery, Chem Commun (Camb), 34:5100-5102 (2009).
Daniel et al., Structural characterization of an elevated lipid bilayer obtained by stepwise functionalization of a self-assembled alkenyl silane film, Biointerphases, 3:109-118 (2007).
U.S. Office Action from U.S. Application No. U.S. Appl. No. 14/877,864, mailed on Apr. 5, 2018.
Afanasenkau et al., Positively Charged Supported Lipid Bilayers as a Biomimetic Platform for Neuronal Cell Culture, Langmuir, (2012), 28:13387-13394.
Chung et al., Formation and analysis of topological domains between lipid membranes tethered by DNA hybrids of different lengths, Faraday Discuss, (2013), 161:333-459.
Wang et al., Defining Single Molecular Forces Required to Activate Integrin and Notch Signaling, Science, (2013), 24:991-994.
European communication from EP Appl. No. 15852876.0, mailed on Jan. 30, 2020.
U.S. Office Action from Appl. No. U.S. Appl. No. 14/877,864, mailed on Nov. 25, 2019.
Nagrath et al., Isolation of rare circulating tumour cells in cancer patients by microchip technology, Nature, (2007), 450:1235-1241.
Picone et al., A Polarised Population of Dynamic Microtubules Mediates Homeostatic Length Control in Animal Cells, PloS Biology, (2010), 8:1-17.
European communication from EP Appl. No. 15772640.7, mailed on Dec. 10, 2020.
European communication from EP Appl. No. 15852876, mailed on Feb. 2, 2022.
Dzmitry et al., Positively Charged Supported Lipid Bilayers as a Biomimetic Platform for Neuronal Cell Culture, Langmuir, (2012), 28:13387-13394.
Chung et al., Formation and analysis of topological domains between lipid membranes tethered by DNA hybrids of different lengths, Faraday discussions, (2013), 161:333-459.
Wang et al., Defining Single Molecular Forces Required to Activate Integrin and Notch Signaling, Science, 340:991-994.

\* cited by examiner

FIG. 13

| | LnCAP | DU145 | PC3 |
|---|---|---|---|
| Confocal Fluorescence microscopy | | | |
| Differential Interference Contrast (DIC) | | | |
| McTN frequency | 9% | 30% | 57% |
| Avg. McTNs/cell (>3μm) | 1 | 5 | 5 |
| Avg. McTN length | 2.6μm | 3.7μm | 3.7μm |
| Integrated McTN score (freq. x length x #/cell) | 23.4 | 555.0 | 1054.5 |
| Prostate stem cell markers (from literature) | | | |
| CD44+/CD24- | 0.04% | 10% | N.D. |
| CD44+/α2β1+ | 0.08% | 24.25% | 10.85% |
| CD44+/CD133+ | 0% | 10.3% | 3.0% |
| Nestin mRNA (fold over benign) | 0 | 5 | 45 |

Microfluidic device to image free-floating patient tumor cells

Movie frame every 15 seconds, 5 z-stacks (Playback 200x, 24 minute timelapses)

MICROTENTACLE IMAGING IN PATIENT TUMOR SAMPLES

CROSS REFERENCE TO RELATED APPLICATIONS

This application claims the benefit of U.S. Provisional Appl. Nos. 61/974,753, filed Apr. 3, 2014 and 62/068,034, filed Oct. 24, 2014. The content of the aforesaid applications are relied upon and incorporated by reference in their entireties.

STATEMENT OF FEDERALLY SPONSORED RESEARCH AND DEVELOPMENT

This invention was made with government support under Grant No. CA154624 awarded by the National Institutes of Health and Grant No. W81XWH-11-1-0244 awarded by the United States Army. The government has certain rights in the invention.

FIELD OF THE INVENTION

The field of the invention relates to the fields of cancer, particularly methods of diagnosis/prognosis and treatment of metastatic cancer.

BACKGROUND OF THE INVENTION

Circulating tumor cells (CTCs) are shed from a primary tumor into the bloodstream. Such cells can nucleate new tumor masses at sites distant to the primary tumor. The presence of CTC's in a cancer patient's blood is associated with a poorer disease prognosis, and methods are available to measure the number CTCs in a cancer patient's bloodstream. However, CTCs are usually present in very small numbers, and some patients in whom CTCs are not detected eventually do develop tumor metastases. Accordingly, new methods are needed for identifying patients at risk for developing tumor metastases.

The present inventor has previously developed methods to image the dynamic surface of free-floating tumor cells (an experimental model for studying CTCs) and discovered unique "microtentacles" on the surface of such free-floating tumor cells. The inventor discovered that the microtentacles promote reattachment and aggregation of tumor cells, thereby promoting tumor metastasis.

Microtentacles are microtubule-based protrusions of the membrane of certain types of tumor cells. Microtubules composed of detyrosinated alpha-tubulin (Glu-tubulin) or acetylated tubulin (Ace-tubulin) have vastly increased stability in vivo, persisting for hours rather than the three to five minutes observed for microtubules composed of tyrosinated tubulin (Tyr-tubulin). Microtentacles are supported by stable microtubules, enriched with Glu-tubulin or Ace-tubulin. Up-regulation of the intermediate filament vimentin is another mechanism by which tumor cells stabilize microtubules. Experimental metastasis studies revealed that promotion of microtentacles increases lung retention of CTCs (Balzer E M, Whipple R A, Thompson K, Boggs A E, Slovic J, Cho E H et al (2010). c-Src differentially regulates the functions of microtentacles and invadopodia. Oncogene 29: 6402-6408); (Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. Oncogene 29: 3217-3227.). Moreover, previous studies in animal models have shown that CTCs reattach to blood vessel walls with a tubulin-dependent cytoskeletal mechanism that appears to rely on the presence of microtentacles (Korb T, Schluter K, Enns A, Spiegel H U, Senninger N, Nicolson G L et al (2004). Integrity of actin fibers and microtubules influences metastatic tumor cell adhesion. Experimental cell research 299: 236-247.). Microtentacles also promote tumor cell clustering, and clusters of CTCs have recently been shown to have 50-fold higher metastatic potential (Aceto N, Bardia A, Miyamoto D T, Donaldson M C, Wittner B S, Spencer J A et al (2014). Circulating tumor cell clusters are oligoclonal precursors of breast cancer metastasis. Cell 158: 1110-1122.). Accordingly, the presence of microtentacles on the surface of a tumor cell indicates a poorer patient prognosis.

Circulating tumor cells (CTCs) can lead to metastatic recurrence but the effects of current cancer drugs on the dynamic responses of these free-floating tumor cells is almost completely overlooked. There is growing evidence that the presence of CTCs in the bloodstream of breast cancer patients predicts poor outcome and an increased risk of metastatic recurrence (Hekimian, K., et al., ISRN Oncol, 2012. 2012: 601810; Riethdorf, S. and K. Pantel, Pathobiology, 2008. 75: 140-8; Ross, J. S. and E. A. Slodkowska, Am J Clin Pathol, 2009. 132: 237-45). Persistent cell cycle arrest renders CTCs highly resistant to traditional chemotherapies targeting cell growth or division (Naumov, G. N., et al., *Cancer Res*, 2002. 62: 2162-8; Naumov, G. N., et al., Breast Cancer Res Treat, 2003. 82: 199-206). Current clinical studies and ongoing drug development focus on inhibiting growth or invasion of attached tumor cells and largely overlook drug effects on free-floating CTCs (Kim, L. C., L. Song, and E. B. Haura, Nat Rev Clin Oncol, 2009. 6: 587-95; Le, X. F. and R. C. Bast, Jr., Cancer Biol Ther, 2011. 12; Patel, R. A., et al., Oncogene, 2013). This could be an important blind-spot since surgery and neoadjuvant chemotherapy can dramatically increase levels of CTCs if every primary tumor cell is not successfully removed or destroyed (Momma, T., et al., Cancer Res, 1998. 58: 5425-31; Goldfarb, Y. and S. Ben-Eliyahu, Breast Dis, 2006. 26: 99-114). This post-treatment CTC increase predicts poor long-term patient outcome (Pachmann, K., et al., J Clin Oncol, 2008. 26: 1208-15; Hekimian, K., et al., ISRN Oncol, 2012. 2012: 601810) highlighting the need to better understand the determinants of CTC metastasis during the post-treatment window.

Free-floating tumor cells produce microtentacles (McTNs) that promote metastatic reattachment. Studies pioneered by the inventor's lab have identified that mammary epithelial and breast carcinoma cells produce extensions of the plasma membrane when detached from extracellular matrix (ECM) (Whipple, R. A., et al., Cancer Res, 2008. 68: 5678-88; Whipple, R. A., A. M. Cheung, and S. S. Martin, Exp Cell Res, 2007. 313: 1326-36) (See FIG. 1). These extensions occur with higher frequency in metastatic breast tumor cell lines (Whipple, R. A., et al., Cancer Res, 2008. 68: 5678-88). Unlike the actin-based invadopodia and filopodia that are well-characterized in tumor cells attached to extracellular matrix, these extensions are based on microtubule expansion and actively suppressed by contraction of the actin cortex beneath the plasma membrane (Matrone, M. A., et al., Cancer Res, 2010. 70: 7737-41). Since such structures had not been reported previously in tumor cells, the inventor's lab introduced the term, microtentacles to describe them (Whipple, R. A., et al., Cancer Res, 2008. 68: 5678-88).

Microtentacles can encircle adjacent cells promoting reattachment of tumor cells to each other and extracellular matrix (Whipple, R. A., et al., Cancer Res, 2008. 68: 5678-88; Whipple, R. A. et al., Exp Cell Res, 2007. 313: 1326-36), but are not observed when cells are grown attached to matrix. There is currently an overwhelming focus of the tumor biology field on cells that are attached to flattened or 3-dimensional extracellular matrix proteins (Yamaguchi, H., J. Wyckoff, and J. Condeelis, Curr Opin Cell Biol, 2005. 17: 559-64; Fischbach, C., et al., Nat Methods, 2007. 4: 855-60), which limits the understanding of cytoskeletal dynamics in free-floating CTCs. Studies using intravital microscopy have shown that the ability of tumor cells to adhere to capillary endothelial cells while circulating in vivo depends on tubulin and not actin (Korb, T., et al., Exp Cell Res, 2004. 299: 236-47). While these studies were conducted at a relatively macroscopic level, the mechanism by which CTCs bind blood vessel walls in vivo (Korb, T., et al., Exp Cell Res, 2004. 299: 236-47) therefore matches precisely with the mechanisms underlying the McTNs that we observe microscopically in detached tumor cells (Matrone, M. A., et al., Cancer Res, 2010. 70: 7737-41; Whipple, R. A., et al., Cancer Res, 2008. 68: 5678-88; Whipple, R. A., A. M. Cheung, and S. S. Martin, Exp Cell Res, 2007. 313: 1326-36). The inventor's lab has also published that elevating McTNs by increasing microtubule stabilization or decreasing actin contraction can promote the retention of CTCs in the lung capillaries of living mice (Balzer, E. M., et al., Oncogene, 2010. 29: 6402-8; Matrone, M. A., et al., Oncogene, 2010. 29: 3217-27) (See FIG. 2).

Cancer drugs aimed at tumor growth and invasion can promote McTNs and stem cell characteristics. Recent developments show that inhibition of actin contractility by targeting the Rho-kinase (ROCK) strongly promotes the ability of epithelial tumor cells from patients to grow indefinitely (Liu, X., et al., Am J Pathol, 2012. 180: 599-607; Suprynowicz, F. A., et al., Proc Natl Acad Sci USA, 2012. 109: 20035-40). Moreover, treatment with ROCK inhibitor also directly increases tumor stem cell characteristics (Ohata, H., et al., Cancer Res, 2012. 72: 5101-10) and McTNs (Bhandary L, Whipple R A, Vitolo M I, Charpentier M S, Boggs A E, Chakrabarti K R, Thompson K N, Martin S S. ROCK inhibition promotes microtentacles that enhance reattachment of breast cancer cells. Oncotarget. 2015 Jan. 31. [Epub ahead of print] PMID: 25749040). Nevertheless, clinical trials with ROCK inhibitors are proceeding (Ying, H., et al., Mol Cancer Ther, 2006. 5: 2158-64; Yap, T. A., et al., Clin Cancer Res, 2012. 18: 3912-23; Vigil, D., et al., Cancer Res, 2012. 72: 5338-47), due to the efficacy of these inhibitors at reducing tumor cell growth and invasion in some model systems. Similarly, reinforcement of microtubules with Paclitaxel also increases stem cell characteristics and even tumor metastasis (Gupta, P. B., et al., Cell, 2009. 138: 645-59). It is notable that both of these drug effects (actin weakening, microtubule stabilization) simulate the cytoskeletal alterations that accompany wound healing and matrix detachment (Even-Ram, S., et al., Nat Cell Biol, 2007. 9: 299-309; Gundersen, G. G. and J. C. Bulinski, Proc Natl Acad Sci USA, 1988. 85: 5946-50) (See FIG. 3).

The inventor's lab has shown that drugs which reduce actin (Jasplakinolide-Jas) or stabilize tubulin (Paclitaxel-Taxol) strongly promote McTNs (Balzer, E. M., et al., Breast Cancer Res Treat, 2010. 121: 65-78) (See FIG. 4), again supporting a model that these drugs could stimulate wound healing or detachment responses in tumor cells. Similar McTN induction occurs when actin contraction is reduced by targeting Src (Balzer, E. M., et al., Oncogene, 2010. 29: 6402-8). It is therefore possible that targeting the cytoskeleton in these ways can reduce tumor growth and motility in the short-term, but may promote increased stem cell characteristics (Ohata, H., et al., Cancer Res, 2012. 72: 5101-10) and tumor recurrence over the long-term (Hekimian, K., et al., ISRN Oncol, 2012. 2012: 601810). Even the most sensitive clinical imaging methods (MRI/PET-CT) can only detect foci of approximately 5 million tumor cells (Li, G., et al., J Appl Clin Med Phys, 2008. 9: 2781), emphasizing that both current drug development and patient monitoring are overlooking effects on tumor cells below this clinical detection threshold, like CTCs.

Neoadjuvant drug effects on CTCs could be increasing metastatic risk. While the concentration of Taxol (1.2 µM) that promotes McTNs is higher than that used to inhibit cell division, it is worth noting that a routine clinical dose (175 mg/m$^2$) yields blood levels of >60 µM Taxol that do not decrease below 1.2 µM until 6 hours following infusion (Bulitta, J. B., et al., Cancer Chemother Pharmacol, 2009. 63: 1049-63). Since CTCs travel from primary tumors to distant tissues within minutes (Chambers, A. F., A. C. Groom, and I. C. MacDonald, Nat Rev Cancer, 2002. 2: 563-72), this provides ample opportunity for Taxol treatment to influence CTC retention at metastatic sites. Neoadjuvant Taxol treatment also increases CTCs more than 1000-fold (Pachmann, K., et al., J Clin Oncol, 2008. 26: 1208-15) when used in advance of surgery. Since neoadjuvant taxane treatment is growing more common (Gralow, J., et al., Clin Breast Cancer, 2008. 8: 33-7), these results emphasize the importance of determining how an individual patient's tumor cells respond to neoadjuvant chemotherapy. During neoadjuvant therapy, a subset of patients unfortunately can show rapid progression (Caudle, A. S., et al., J Clin Oncol, 2010. 28: 1821-8), and there is currently a need to better predict which patients are at risk for progression during neoadjuvant treatment. A recent clinical study involving 1,762 patients did not detect an appreciable advantage of neoadjuvant therapy to overall patient survival, but 59 of these patients rapidly progressed to metastatic disease, and the one of the greatest risk factors was inclusion of a tubulin-stabilizing taxane in the neoadjuvant regimen (Caudle, A. S., et al., J Clin Oncol, 2010. 28: 1821-8). Current clinical imaging technology makes it very difficult to distinguish if a tumor is shrinking on an MRI because it is dying or because the tumor is scattering (Li, G., et al., J Appl Clin Med Phys, 2008. 9: 2781). These two scenarios have dramatically different implications for the patient. Careful monitoring of CTC levels when chemotherapy was given before surgery (Hekimian, K., et al., ISRN Oncol, 2012. 2012: 601810) (See FIG. 5) showed that when CTCs increased in the bloodstream during therapy, only 4% of these patients were relapse-free after 7 years, while 100% of patients whose CTCs decreased remained relapse-free at 7 years. This 25-fold increased risk of relapse (Hekimian, K., et al., ISRN Oncol, 2012. 2012: 601810) clearly emphasizes the importance of understanding how current cancer drugs could affect the cytoskeletal mechanics of free-floating CTCs. These results (Hekimian, K., et al., ISRN Oncol, 2012. 2012: 601810) and the current limitations of clinical imaging (Li, G., et al., J Appl Clin Med Phys, 2008. 9: 2781) highlight the need to better understand the mechanisms that influence CTC metastasis in individual patients to effectively guide therapy.

Live confocal imaging demonstrates that McTNs promote aggregation and endothelial attachment of free-floating tumor cells. The inventor's lab determined that the delicate structure of McTNs required new methods to image dynamic shape changes in live, detached tumor cells (Balzer, E. M., et al., Oncogene, 2010. 29: 6402-8; Balzer, E. M., et al., Breast Cancer Res Treat, 2010. 121: 65-78.; Whipple, R. A., et al., Cancer Research, 2008. 68: 5678-88). Using high-speed confocal microscopy, the inventor has shown that McTNs encircle neighboring cells to promote the aggregation of detached tumor cells (Matrone, M. A., et al., Cancer Res, 2010. 70: 7737-41) (See FIG. 6). Such resolution of individual McTNs would be impossible with traditional fixed-cell immunofluorescence or even electron microscopy, since surface or cytoskeletal stains cannot distinguish between the neighboring cells (See FIG. 6A). The discovery that McTNS promote tumor cell clustering is particularly notable since CTCs clusters have recently been shown to have 50-fold higher metastatic potential (Aceto N, Bardia A, Miyamoto D T, Donaldson M C, Wittner B S, Spencer J A et al (2014). Circulating tumor cell clusters are oligoclonal precursors of breast cancer metastasis. Cell 158: 1110-1122.).

Using this imaging method in combination with human endothelial cells stably expressing the red fluorescent protein, mCherry, the inventors also published the ability of McTNs to promote the penetration of endothelial cell layers to contact the underlying substratum (Matrone, M. A., et al., Cancer Res, 2010. 70: 7737-41); (Whipple R A, Matrone M A, Cho E H, Balzer E M, Vitolo M I, Yoon J R et al (2010). Epithelial-to-mesenchymal transition promotes tubulin detyrosination and microtentacles that enhance endothelial engagement. Cancer Res 70: 8127-8137). (See FIG. 7). Interestingly, while selectin-mediated adhesion allows tumor cells to roll along blood vessel walls, only integrin-mediated adhesion with the underlying extracellular matrix allows tumor cells to arrest against the force of blood flow and extravasate successfully (Haier, J. and G. L. Nicolson, Apmis, 2001. 109: 241-62). These results add more support for a potential role of McTNs in the initial retention of CTCs in distant tissues (Balzer, E. M., et al., Oncogene, 2010. 29: 6402-8; Matrone, M. A., et al., Oncogene, 2010. 29: 3217-27; Korb, T., et al., Exp Cell Res, 2004. 299: 236-47).

Emerging evidence indicates the potential long-term danger of cytoskeletal cancer drugs that increase circulating tumor cells (Pachmann, K., et al., J Clin Oncol, 2008. 26: 1208-15; Hekimian, K., et al., ISRN Oncol, 2012. 2012: 601810) or promote tumor stem cell characteristics (Balzer, E. M., et al., Breast Cancer Res Treat, 2010. 121: 65-78; Liu, X., et al., Am J Pathol, 2012. 180: 599-607; Suprynowicz, F. A., et al., Proc Natl Acad Sci USA, 2012. 109: 20035-40; Ohata, H., et al., Cancer Res, 2012. 72: 5101-10). These data emphasize the importance of developing rapid methods to define the mechanics and drug responses of tumor cells from individual patients so that cancer drugs aimed at tumor cell division or invasion do not inadvertently increase long-term metastasis.

Accordingly, there remains a need for methods for detecting microtentacles in primary tumor samples to improve prognosis and provide for more effective cancer treatments.

SUMMARY OF THE INVENTION

It is described herein that cells with metastatic potential, when freshly isolated from a solid tumor, generate long and dynamic microtubule-driven protrusions of the plasma membrane after dissociation and detachment referred to herein as microtentacles. The present invention is directed to methods and compositions for detecting microtentacles in cellular samples to improve prognosis and provide for more effective cancer therapies by screening drugs for their ability to inhibit or promote microtentacle formation or stability.

According to non-limiting example embodiments, in one aspect, the present invention provides methods to identify a patient with an increased likelihood of having or developing metastatic cancer. In some embodiments of the invention, tumor cells from a tumor or tumor biopsy removed from the patient are analyzed to determine whether the tumor cells, when dissociated from the tumor and detached from substrate, display microtentacles on their cell surface. The presence of microtentacles on the surface of the tumor cells identifies a patient with an increased likelihood of having or developing metastatic cancer.

The present invention also provides methods to rapidly determine how a patient's tumor will respond to various cancer drugs, by incubating the above-mentioned tumor cells with various cancer drugs while detached from substrate, to determine whether the drugs decrease the incidence of microtentacles on the surface of the tumor cells. In some embodiments, drugs that increase the number and/or length of microtentacles on the surface of the tumor cells should not be administered to the patient, whereas cells that decrease (or at least do not increase) the number and/or length of microtentacles on the surface of the tumor cells can be administered to the patient. In other embodiments, a therapy which increases microtentacles could be used in combination with a therapy that reduces microtentacles to counteract the detrimental effects of microtentacle promotion.

In another aspect, the invention provides a method for imaging microtentacles on isolated, living, non-adherent primary tumor cells from a cancer subject comprising:
  i) obtaining one or more living, non-adherent primary tumor cells that has been isolated from a solid tumor from the subject; and
  ii) imaging the one or more living, non-adherent primary tumor cells and detecting the microtentacles.

In another aspect, the invention provides a method of identifying a subject with an increased likelihood of having or developing metastatic cancer comprising:
  i) obtaining one or more living, non-adherent primary tumor cells that has been isolated from a solid tumor from the subject;
  ii) imaging the one or more living, non-adherent primary tumor cells; and
  iii) scoring the one or more imaged cells for microtentacles to determine whether the subject has an increased likelihood of having or developing metastatic cancer.

In another aspect, the invention provides a method for determining whether a candidate drug inhibits or promotes microtentacle formation and/or stability on isolated, living, non-adherent primary tumor cells from a cancer subject comprising:
  i) obtaining one or more living, non-adherent primary tumor cells that has been isolated from a solid tumor from the subject;
  ii) contacting the one or more living, non-adherent primary tumor cells with the candidate drug;
  iii) imaging the one or more living, non-adherent primary tumor cells treated with the candidate drug; and
  iv) scoring the one or more imaged cells for microtentacles to determine whether a candidate drug inhibits or promotes microtentacle formation and/or stability.

In another aspect, the invention provides a method for determining the stem cell potential of tumor cells from a cancer subject comprising:

i) obtaining one or more living, non-adherent primary tumor cells that has been isolated from a solid tumor from the subject;
ii) imaging the one or more living, non-adherent primary tumor cells; and
iii) scoring the one or more imaged cells for microtentacles to determine the stem cell potential of the tumor cell.

It is to be understood that both the foregoing general description and the following detailed description are exemplary, and thus do not restrict the scope of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 13. McTNs in prostate tumor cell lines. LnCAP, DU145 and PC3 prostate tumor cells were imaged for McTNs with CellMask confocal microscopy (upper panels) or DIC brightfield microscopy (lower panels). Weakly metastatic LnCAP cells have a smooth surface and very few McTNs, while the more highly metastatic DU145 and PC3 cells have more McTNs. Automated McTN analysis and published stem cell markers in prostate cancer are shown for each cell line.

Figure 1:
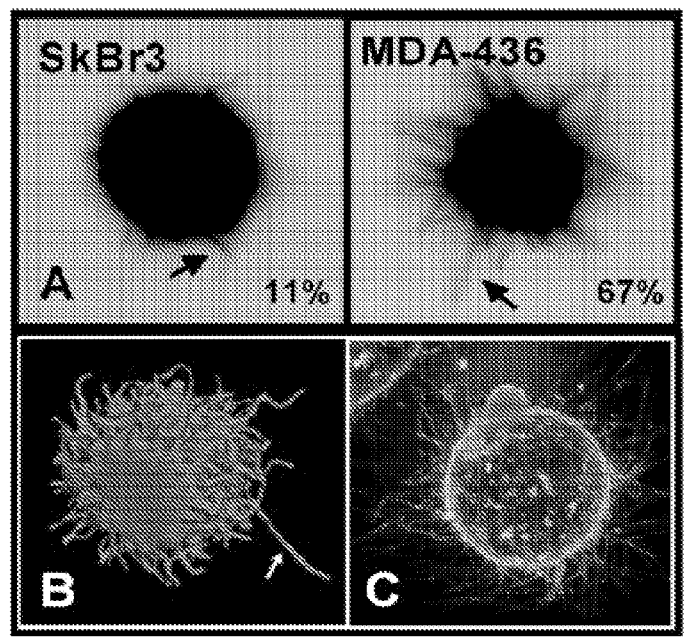
FIG. 1. Microtentacles in metastatic breast tumor cells. A) Human breast tumor cell lines transfected with membrane-localized green fluorescent protein (GFP) display protrusions when detached (black arrows, images inverted for contrast), that we have termed microtentacles (McTNs), due to a novel tubulin-based supporting mechanism. Cell lines with higher metastatic potential (MDA-436) show higher frequencies of McTNs when scored blindly for protrusions longer than the cell radius (Values=avg.±S.D. for 3 expts with at least 100 cells counted blindly). McTNs are only observed when cells are detached from extracellular matrix, regardless of method used (collagenase, trypsin, enzyme-free, scraping). Moreover, the delicate microtubule structure of McTNs causes them to collapse when treated with traditional fixatives (methanol, formaldehyde), which is a major reason why these structures were previously overlooked. Beyond GFP, we have used fluorescent staining methods with dyes based on cell surface glycosylation (B) or lipophilic membrane dyes (C) to resolve McTNs with live-cell confocal microscopy. Comparison with live cells allowed us to pioneer fixation methods that retain McTNs.

The skilled artisan will understand that the drawings, described below, are for illustration purposes only. The drawings are not intended to limit the scope of the present teachings in any way.

DETAILED DESCRIPTION

The present invention generally concerns the previously unknown phenomenon that certain primary tumor cells isolated from a patient's solid tumor and placed under non-adherent in vitro culture conditions can generate microtubule protrusions that increase the cells' ability to reattach to each other and/or surfaces. Because tumor cells become detached during spread through the blood or lymphatics, the generation of these protrusions is important for the ability of the tumor cells to spread metastatically to distant tissues and/or organs. Thus, the ability of a tumor cell to form such microtubule protrusions is an indication of its metastatic potential. In vivo, such microtubule protrusions can act to enhance tumor cell adhesion to vessel walls and/or allow tumor cells to avoid being crushed by size-restriction in capillaries. These protrusions increase in number and size per cell in more metastatic tumor cell lines. Protrusions also occur with a significantly higher frequency in populations of breast tumor cells with greater metastatic potential. In particular, death of cancer patients is most often caused by metastatic spread of the primary tumor through the bloodstream. However, large tumor cells are efficiently killed by shearing when they are pushed through small-diameter capillaries by blood pressure. The microtubule protrusions can help metastatic tumor cells avoid death by adhering to vessel walls and/or bracing against them before the size of the capillary becomes limiting. Inhibition of the function of these microtubule protrusions and/or inhibition of their production, for example, allows metastatic tumor cells to have a greater opportunity to be efficiently killed, such as by shearing through capillary beds, for example. In specific embodiments, the invention focuses on the imaging and detection of these structures in living, non-adherent primary tumor cells isolated from a solid tumor from a cancer subject to improve prognosis and provide for more effective cancer treatments.

As provided herein, it has now been discovered that it is possible to immediately image microtentacles in tumor cells taken directly from tumors, from tumor cell biopsies or primary tumors surgically removed from cancer patients. Before the present invention, it was thought that tumor cells with microtentacles were present only as circulating tumor cells in the bloodstream of cancer patients having tumor metastases or at risk for metastases. The present discovery allows direct examination of cells from a primary tumor or surgical biopsy for the presence of microtentacles, which has various benefits that provide prognostic information and can guide patient treatment.

There are numerous advantages in some embodiments of the present invention. First, the present discovery provides an immediate functional phenotype to measure (as opposed to a static gene or protein expression profile). Second, the tumor cell imaging studies can be immediately conducted with very few cells. Because no long-term cell culturing is needed, the risk of in vitro selection for tumor cells with altered properties relative to the patient's original tumor cells is avoided. Third, the inventor has discovered that tumor stem cells are enriched in microtentacles at their cell surface. Thus, analysis of a patient's fresh tumor cells can provide an indication of a tumor's "stemness," which is known to be associated with an increased metastatic risk. Fourth, since microtentacle dynamics are very rapid, drug effects can be measured within minutes. Thus, the imaging of microtentacles on the surface of tumor cells taken from tumor biopsies or surgically-removed tumor specimens provides the opportunity to rapidly gauge a tumor's potential response to various cancer drugs prior to treatment, thereby allowing treatment to be tailored to the patient.

References will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

The term "microtentacles" as used herein refers to extensions of the plasma membrane in detached cells that are enriched in tubulin protein, for example Glu-tubulin or Ace-tubulin and largely devoid of polymerized actin. When treated with inhibitors of actin depolymerization, there is enhancement of the protrusions, such as with the protrusions increasing in length, number per cell and frequency in a population, for example. This is in contrast to well-known invadopodia and podosomes associated with adherent tumor cells that are actin-based and inhibited by actin depolymerization.

In one embodiment, the invention provides a method for imaging microtentacles on isolated, living, non-adherent primary tumor cells from a cancer subject comprising:
  i) obtaining one or more living, non-adherent primary tumor cells that has been isolated from a solid tumor from the subject; and
  ii) imaging the one or more living, non-adherent primary tumor cells and detecting the microtentacles.

In another embodiment, the invention provides a method of identifying a subject with an increased likelihood of having or developing metastatic cancer comprising:
  i) obtaining one or more living, non-adherent primary tumor cells that has been isolated from a solid tumor from the subject;
  ii) imaging the one or more living, non-adherent primary tumor cells; and
  iii) scoring the one or more imaged cells for microtentacles to determine whether the subject has an increased likelihood of having or developing metastatic cancer.

In some embodiments, the scoring comprises determining whether the one or more cells comprise two or more protrusions longer than the cell radius, wherein the one or more cells comprising two or more protrusions longer than the cell radius indicates an increased likelihood of having or developing metastatic cancer. See, e.g., Balzer, E. M., et al., Oncogene, 2010. 29: 6402-8; Whipple, R. A., et al., Cancer Res, 2010. 70: 8127-37; Balzer, E. M., et al., Breast Cancer Res Treat, 2010. 121: 65-78.

The present invention further comprises methods for identifying which candidate drugs should be administered to a cancer patient by assaying whether the drug inhibits, promotes and/or stabilizes the microtentacles. In some embodiments, drugs which stabilize or promote microtentacle formation should not be administered to patients whereas drugs which inhibit, destabilize or have no effect on microtentacles can be administered. These assays can comprise random screening of large libraries of candidate substances; alternatively, the assays may be used to focus on particular classes of compounds selected with an eye towards structural attributes that are believed to make them more likely to modulate the function of one or more microtubule protrusions or one or more components thereof. In some embodiments, the invention provides a method for determining whether a candidate drug inhibits or promotes microtentacle formation and/or stability on isolated, living, non-adherent primary tumor cells from a cancer subject comprising:
  i) obtaining one or more living, non-adherent primary tumor cells that has been isolated from a solid tumor from the subject;
  ii) contacting the one or more living, non-adherent primary tumor cells with the candidate drug;
  iii) imaging the one or more living, non-adherent primary tumor cells treated with the candidate drug; and
  iv) scoring the one or more imaged cells for microtentacles to determine whether a candidate drug inhibits or promotes microtentacle formation and/or stability.

In some embodiments, the method further comprises administering an effective amount of the candidate drug to the subject to treat the cancer. In some embodiments, the candidate drug is administered if it inhibits microtentacle formation and/or stability or has no effect on microtentacles. In some embodiments, the subject is not administered an effective amount of the candidate drug if that drug promotes microtentacle formation and/or stability.

As used herein the term "candidate drug" refers to any molecule that may potentially inhibit or promote microtentacle formation and/or stability. The candidate drug is not limiting and can include a protein or fragment thereof, a small molecule, or even a nucleic acid molecule. In some embodiments, the candidate drug can include approved drugs currently used in cancer therapy, non-approved drugs, investigational compounds, and compounds from libraries which can be screened for activity.

In some embodiments, the candidate drug is selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate). In some embodiments, the drug is selected from the group consisting of Paclitaxel, Curcumin, Docetaxel, Ixabepilone, Vinblastine, Colchicine, Y-27632 Fasudil, SU6656 Dasatinib, HDAC inhibitors, ROCK inhibitors, Parthenolide, Costunolide and ML-7 Jazplakinolide. U.S. Pat. No. 8,193,238 also describes a number of compounds which have potential for inhibition of microtentacles which can be used in the present methods, the disclosure of which is incorporated by reference herein in its entirety.

In some embodiments, the method further comprises imaging one or more living, non-adherent primary tumor cells that have not been treated with the candidate drug and scoring the untreated cells for microtentacles, and comparing the score for untreated cells with the score obtained from step iv) for treated cells. In some embodiments, the treated and untreated cells are the same cells and the untreated cells are imaged and scored prior to step ii). In some embodiments, the scoring comprises determining whether the one or more cells comprise two or more protrusions longer than the cell radius. See, e.g., Whipple et al., Experimental Cell Research 313(7):1326-36 (2007). In some embodiments, the candidate drug promotes microtentacle formation and/or stability when the one or more cells exhibit a greater number of protrusions longer than the cell radius compared to untreated cells. In some embodiments, the candidate drug inhibits microtentacle formation and/or stability when the one or more cells exhibit a reduced number of protrusions longer than the cell radius compared to untreated cells.

In another embodiment, the invention provides a method for determining the stem cell potential of tumor cells from a cancer subject comprising:
 i) obtaining one or more living, non-adherent primary tumor cells that has been isolated from a solid tumor from the subject;
 ii) imaging the one or more living, non-adherent primary tumor cells; and
 iii) scoring the one or more imaged cells for microtentacles to determine the stem cell potential of the tumor cell.

In some embodiments, the scoring comprises determining whether the one or more cells comprise two or more protrusions longer than the cell radius, wherein the one or more cells comprising two or more protrusions longer than the cell radius have a greater stem cell potential than cells having fewer than two protrusions longer than the cell radius.

As used herein, "non-adherent" primary tumor cells are cells that have been isolated from a solid tumor by human intervention and placed under in vitro conditions in which the cells generally do not form significant protein-based contacts to an in vitro surface (such as that of a coated or uncoated cell culture chamber or microfluidic slide) during the time in which the tumor cells are being tested or studied, so as to allow the formation of microtentacles by the tumor cells capable of forming such microtentacles. Such "non-adherent" cells include cells that are tethered to the in vitro surface, e.g., by a oligonucleic acid tether or lipid tether as described herein.

As used herein, cells "isolated from a solid tumor" means cells are isolated from a solid tumor by human intervention and do not encompass detached cancer cells that have escaped their primary organ site, and are present elsewhere in the body of the patient, for example in the bloodstream or lymph nodes. The cells that are isolated from a solid tumor are primary cells, and do not encompass cells from cancer cell lines, which were originally derived from a solid tumor. In some embodiments, the cells are isolated directly from a non-removed tumor, from a tumor cell biopsy or from a tumor that is surgically removed. In some embodiments, the isolated cells are grown in mice (tumorgrafts, PDX) and then analyzed. In some embodiments, the isolated cells are cultured with conditional reprogramming and then analyzed.

The number of cells that can be isolated and assayed is not limiting. In some embodiments, fewer than 1000 cells are isolated and analyzed. In some embodiments, fewer than 200 cells are isolated and analyzed. In some embodiments, fewer than 50 cells are isolated and analyzed. In some embodiments, about 12 cells are isolated and analyzed. In some embodiments, at least one cell is isolated and analyzed. The cells can be isolated from surrounding cells and tissue to yield single-cell suspensions using standard techniques.

Surgical and needle biopsy samples provide a unique resource for early measurements of tumorigenic and metastatic potential in live tumor cells that is amenable to testing individual patient prognosis and drug responses without requiring long-term growth in cell culture. Culturing of patient-derived tumor cells can impose selective pressures that yield tumor cell populations which do not reflect the molecular characteristics of the patients' original tumors (DeRose, Y. S., et al., Nat Med, 2011. 17: 1514-20). In some embodiments, the invention allows a comprehensive mechanical analysis of free-floating (non-adherent), patient-derived tumor cells within hours or even minutes of their removal from the patient during surgery. In some embodiments, the methods of the invention can be applied on groups of fewer than 200 cells, which would allow their use from even core needle biopsy samples at the time of initial diagnosis. In some embodiments, the cells are freshly isolated from a solid tumor from the subject and the cells are dissociated and imaged for the microtentacles. In some embodiments, the cells are imaged within one week of isolation. In some embodiments, the cells are imaged within 48 hours of isolation, within 24 hours of isolation, within 12 hours of isolation, within 6 hours of isolation, within 2 hours of isolation and within 1 hour of isolation. In some embodiments, the cells have not undergone more than three doublings, more than two doublings, or more than a single doubling since isolation from the solid tumor.

The imaging the one or more living, non-adherent primary tumor cells is not limiting, provided, however, that the imaging allows for the detection of the microtentacles. In some embodiments, the cells are imaged using microscopy. In some embodiments, the cells are imaged by confocal microscopy. In some embodiments, the cells are imaged by flow cytometry image stream analysis (see, e.g., Imagestream by Amnis (Seattle, WA)). In some embodiments, one or more membrane markers are labeled to facilitate visualization of the plasma membrane and the microtentacles. In some embodiments, the plasma membrane is labeled with a fluorescent dye to visualize the microtentacles. In some embodiments, a lipophilic membrane dye (e.g., CellMask, 1:10,000, Invitrogen) can be added to the cells to facilitate membrane and microtentacle visualization of live cells. See, e.g., Charpentier et al., Cancer Research 15; 74(4):1250-60 (2014). In some embodiments, one or more other methods for surface labeling are employed, e.g., WGA (Balzer, E. M., et al., Breast Cancer Res Treat, 2010. 121: 65-78), GFP-membrane (Whipple et al., Cancer Research 68(14):5678-88 (2008); Whipple et al., Cancer Res 70:8127-37 (2010)) or microtubule visualization of microtentacles (Balzer et al., Breast Cancer Res Treat 121: 65-78 (2010)).

Tumor cells that can be analyzed by the methods of the invention can be from any type of tumor in which microtentacle formation is involved in metastasis, for example, breast cancer, prostate cancer, lung cancer, bladder cancer, pancreatic cancer, brain cancer, liver cancer, testicular cancer, thyroid cancer, skin cancer, colon cancer, ovarian cancer, cervical cancer, and uterine cancer.

In some embodiments, the tumor cells are tethered to a substrate during imaging of the cell and microtentacles. The nature of the tethering of the cells to a substrate is not limiting provided that the cells maintain their free-floating, non-adherent character, and are able to form microtentacles. In some embodiments, the substrate is coated with one or more layers of one or more materials that substantially inhibit the cells from adhering to the substrate. In some embodiments, the substrate is coated with one or more polyelectrolytes. In some embodiments, the substrate is coated with polyelectrolyte multilayer films (PEMs) to coat the imaging surface to both prevent the formation of protein-based attachments and reduce cell displacement. In some embodiments, the PEMs are exceptionally thin (10-100 nm) and can incorporate tethering molecules in their top surface, such as DNA oligos or lipids that can interact with cell membranes and hold free-floating cells without allowing cell spreading. In some embodiments, microcontact printing (µCP) can be implemented to allow patterning of these attachment points. Tethered cells maintain the McTN dynamics and drug responses of free-floating cells, but can be held in an arrayed pattern for staining and high-resolution imaging. In some embodiments, the PEMs are prepared by adsorption of alternating layers of polycationic and polyanionic solutions to the substrate that assemble through electrostatic or hydrogen bonding (see FIG. 17A). In some embodiments, the films are ultrathin (10-100 nm), optically clear, and use a simple all-aqueous approach based on sequential exposure of a target surface or substrate to the polyelectrolyte solutions. In some embodiments, the PEMs are created on microfluidic slides or microfluidic channels (see FIG. 17B). In some embodiments, the PEMs are formed from a combination of polymethacrylic acid (PMA) and polyacrylamide (PAAm). In some embodiments, the PEMs comprise about 2-10 layers. PEMs are described in, e.g., Jewell et al., Advanced drug delivery reviews 60: 979-999 (2008); Jewell et al., Biomacromolecules 7: 2483-2491 (2006); Jewell et al., Journal of Controlled Release 106: 214-223 (2005)).

In some embodiments, the coated substrate is further coated with a tethering substance, which will adhere to the substrate and is capable of tethering the cell to the substrate and holding it in a substantially fixed position for imaging analysis. The tether is not limiting and can include any substance, such as proteins, lipids, nucleic acids, carbohydrates, aptamers, etc. In some embodiments, the tether is a lipid. In some embodiments, the tether is a charged lipid. In some embodiments, the tether is a glycerophospholipid. In some embodiments, the tether is selected from the group consisting of dotap (1,2-di-(9Z-octadecenoyl)-3-trimethyl-ammonium-propane (chloride salt)), 18:O-LysoPG and 15:O(3)-16:1-CA.

In some embodiments, the cells are imaged while tethered to a microfluidic slide. In some embodiments, the microfluidic slide comprises a polyelectrolyte multilayer comprising a combination of polymethacrylic acid (PMA) and polyacrylamide (PAAm), and dotap as the tether. In some embodiments, the microfluidic slide can accommodate a sample volume of as little as 30 uL.

The present invention is further illustrated by the following Examples. These Examples are provided to aid in the understanding of the invention and are not to be construed as a limitation thereof.

EXAMPLES

Example 1

Rapid Characterization of Microtentacles on Patient Tumors with Live-Cell Confocal Microscopy.

Figure 8:
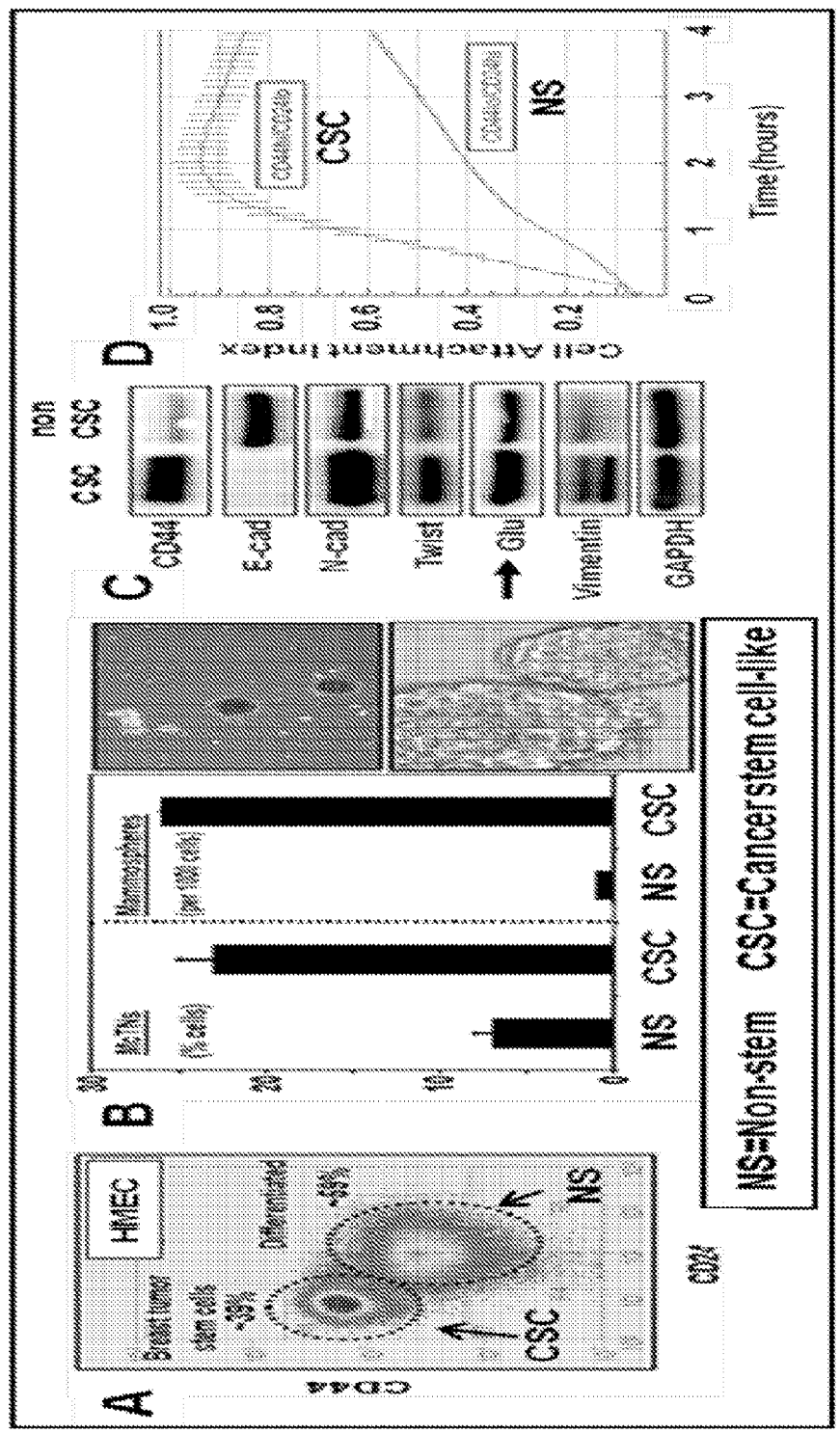
FIG. 8. Breast tumor stem cells have elevated microtentacles that promote reattachment. A) Flow cytometry sorting of immortalized human mammary epithelial (HMEC) cells for those that express high levels of CD44 and low levels of CD24 (CD44+/CD24−) isolates a stem cell population from breast tumor cell lines. B) McTNs and mammospheres are strongly upregulated in the CSC subpopulation. C) Likewise, EMT protein markers increase in the CSC population, including stabilized tubulin (Glu, arrow) and vimentin. D) Reflecting the elevated McTNs, the CSC population reattaches faster, when gauged by electrical impedance.

McTNs on the surface of free-floating tumor cells serve as an indicator of their reattachment efficiency during experimental metastasis in vivo (Balzer, E. M., et al., Oncogene, 2010. 29: 6402-8; Matrone, M. A., et al., Oncogene, 2010. 29: 3217-27). In addition, our data now demonstrate that McTNs are a marker of increased stem cell characteristics (FIG. 8). Live-cell confocal microscopy can be used to examine McTN extension and dynamics in freshly-isolated tumor cells from cancer patients (such as those having breast cancer, prostate cancer, colon cancer, and other cancers as described herein) and relate McTN incidence and drug response to the tumorigenic and metastatic properties of parallel patient-derived tumorgrafts. Mechanical properties of the fresh tumor cells, tumorgraft-derived cells and fresh-frozen tissue can be compared to determine the durability of mechanical properties with different tumor banking techniques.

Example 2

Image Microtentacles in Patient-Derived Tumor Cells with Live-Cell Confocal Microscopy.

For frozen or fresh tumor fragments, stromal matrix is digested with collagenase/hyaluronidase (12 h, 37° C.), and epithelial cell organoids are isolated from residual fat cells and lymphocytes by centrifugation (530×g, 5 min.) (DeRose, Y. S., et al., Curr Protoc Pharmacol, 2013. Chapter 14: Unit14 23). Organoid pellets are washed with growth media (Hyclone DMEM/F12+HEPES, FBS, BSA, insulin, hydrocortisone) and subjected to cycles of centrifugation until the purity of epithelial organoids is confirmed (DeRose, Y. S., et al., Curr Protoc Pharmacol, 2013. Chapter 14: Unit14 23). Organoids are dissociated with Trypsin/EDTA to yield a single-cell suspension of epithelial tumor cells. Half of this suspension is labeled with anti-CD45 (Alexa 648, Genetix) to exclude lymphocytes and anti-EpCAM (Alexa488, Miltenyi) to identify tumor cells. CellMask lipophilic membrane dye (1:10,000, Invitrogen) is added and live cells imaged on an Olympus FV-1000 confocal microscope (FIG. 9) with an incubated stage enclosure (Ibidi). Random fields totaling over 200 cells are blindly scored to determine the percentage of CD45−/EpCAM+ cells displaying two or more McTNs, according to our published methods (Balzer, E. M., et al., Oncogene, 2010. 29: 6402-8; Whipple, R. A., et al., Cancer Res, 2010. 70: 8127-37; Balzer, E. M., et al., Breast Cancer Res Treat, 2010. 121: 65-78; Vitolo, M. I., et al., Oncogene, 2012).

Figure 9:
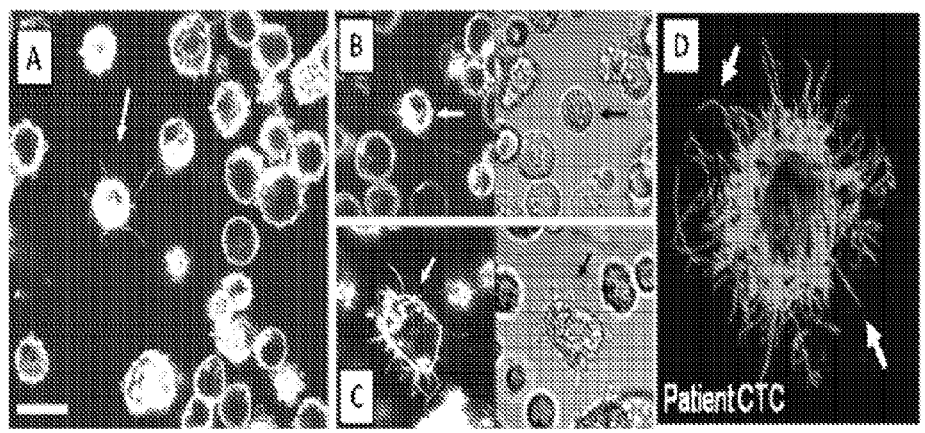
FIG. 9. Live patient tumor cells show evidence of McTNs. Epithelial organoids derived from patient breast tumors were dissociated and viewed live with confocal microscopy after membrane labeling with CellMask. Low (A) and high (B,C) magnification confocal images show evidence of McTNs (white arrows). Similarly, when EpCAM-isolated CTCs from patients are immunofluorescently stained for tubulin, microtentacle extension is also evident (D). McTNs on live patient cells.
Figure 10:
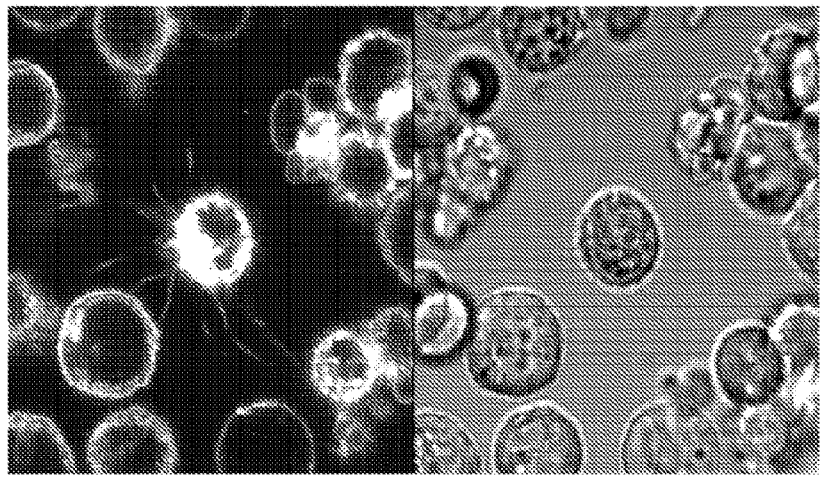
FIG. 10. Surgical samples from breast cancer patients (membrane dynamics—600×)

McTNs are observed in live cells from patients as well as fixed cells that are purified by binding to anti-EpCAM antibodies (FIG. 9). Moreover, McTNs are enriched in the tumor cell subpopulation with increased cancer stem cell characteristics (FIG. 8). The CellMask method is currently the most effective for imaging live cells (Vitolo, M. I., et al., Oncogene, 2012), but numerous other methods for surface labeling (WGA (Balzer, E. M., et al., Breast Cancer Res Treat, 2010. 121: 65-78), GFP-membrane (Whipple, R. A., et al., Cancer Res, 2010. 70: 8127-37)) or microtubule visualization of McTNs (Balzer, E. M., et al., Breast Cancer Res Treat, 2010. 121: 65-78) can be used as CellMask alternatives.

Example 3

Comparison of In Vitro McTN Counts with In Vivo Tumor Growth and Metastasis.

In vitro McTN counts are a possible indicator of in vivo metastatic potential. This was first tested in cultured breast tumor cell lines (Whipple et al., Cancer Research 2008). In subsequent publications, two different genetic models were used to demonstrate that direct induction of McTNs through microtubule stabilization (Matrone et al, Oncogene. 2010 Jun. 3; 29(22):3217-27. doi: 10.1038/onc.2010.68. Epub 2010 Mar. 15) or actin disruption (Balzer et al., Oncogene. 2010 Dec. 2; 29(48):6402-8. doi: 10.1038/onc.2010.360. Epub 2010 Oct. 18) led to increased retention of circulating breast tumor cells in the lungs of living mice with bioluminescence imaging. More recently, it has also been shown that McTNs are increased in breast cancer stem cells (Charpentier et al., Cancer Research, 2014) revealing a possible connection between McTNs and the growth potential of breast tumors.

Advances in the analysis of patient-derived tumor cells (DeRose et al., Nature Medicine, 17(11): 1514-20. 2011) have now shown that direct transplant of fresh tumor fragments from breast cancer patients into the mammary gland of NOD/SCID immunodeficient mice allows the growth of patient-derived xenografts (PDX) that maintain important connections with the original cancer patient. First, the principal molecular markers (ER/PR/HER2) are retained in the PDX compared to the original patient. Second, while only approximately 40% of PDX grow in mice, this growth is prognostic for whether the patient is likely to have tumor recurrence. Third, the pattern of metastatic spread in the mice matches the original patient. For these principal reasons, PDX are currently considered an improved model of patient tumor cells than more traditional cultured cell lines.

As set forth herein, it is now demonstrated that McTNs are detectable in fresh patient tumor cells, within hours of when the patient cells are removed during surgery. To generate more patient-derived cells for analysis, patient cells have been propagated as PDX to retain the important connections to the original patient data (growth, metastasis, etc.).

Table 1 shows the lowest McTN frequencies are found in HCI-003 (ER+/PR+) and the non-metastatic PDX line (HCI-004). These patient profiles have better overall prognosis. The highest McTN counts are also found in those PDX that grow more rapidly (HCI-001, HCI-002), indicating a possible connection with increased stem cell characteristics in cells producing McTNs (Charpentier et al., Cancer Research, 2014). The increased McTN metrics that are enabled by the present invention through image analysis hold the potential to reveal more predictors of clinical outcome (McTN length, # per cell, curvature, motion, etc.).

TABLE 1

List of current human patient-derived xenografts (pdx):

| Cell ID# | ER | PR | HER2 | Metastasis | Initial Growth (time to 0.1 cm$^3$) | Patient race | McTNs (% cells) |
|---|---|---|---|---|---|---|---|
| HCI-001 | − | − | − | Lung, LN | 4 weeks | Caucasian | 31 ± 3 |
| HCI-002 | − | − | − | LN | 5 weeks | Caucasian | 21 ± 3 |
| HCI-003 | + | + | − | Lung, LN | 11 weeks | Caucasian | 5 ± 1 |
| HCI-004 | − | − | − | None detected | 21 weeks | Caucasian | 10 ± 2 |
| HCI-005 | + | + | + | Lung, bone | 13 weeks | Caucasian | 17 ± 2 |
| HCI-011 | + | + | − | LN, pleura | 27 weeks | African-American | |

More importantly, the present invention enables the rapid testing of patient tumor cells for responses to cancer drugs without requiring long-term growth. The cytoskeletal drug responses measured so far range from 5 minutes to 60 minutes treatment. The present invention therefore provides a method to determine how an individual patient's tumor cells respond to different cancer treatments, enabling a rapid and functional personalized medicine profile. The demonstration of McTNs in PDX cells allows application of these drug testing methods to freshly isolated patient cells, thereby allowing rapid tailoring of a patient's treatment regimen in accordance with the patient's microtentacle drug response profile.

Example 4

Examination of McTN and Stem Cell Responses of Patient-Derived Cells to FDA-Approved Drugs.

Patient-derived cells are treated with either vehicle (0.1% DMSO) or each of the drugs in Table 2 at the indicated concentration for 30 minutes and then analyzed for McTN incidence.

TABLE 2

List of cytoskeletal modulators. (FDA-approved*)

| Drugs | Conc. | | Target | Effect | Predicted stemness & McTN effect |
|---|---|---|---|---|---|
| Paclitaxel* | 1 | μM | Microtubules | Stabilize | Increase |
| Docetaxel* | 0.2 | μM | | | |
| Ixabepilone* | 0.2 | μM | | | |
| Vinblastine* | 0.1 | μM | Microtubules | Depolymerize | Decrease |
| Colchicine* | 50 | μM | | | |
| Y-27632 | 30 | μM | Actomyosin (ROCK) | Weaken | Increase |
| Fasudil* | 50 | μM | | | |
| SU6656 | 10 | μM | Actomyosin (Src) | Weaken | Increase |
| Dasatinib* | 3 | μM | | | |
| ML-7 | 30 | μM | Actomyosin | Strength | Decrease |
| Jazplakinolide | 0.5 | μM | | | |
| Parthenolide | 10 | μM | Glumicrotubules | Reduce | Decrease |
| Costunolide | 10 | μM | | | |

Example 5

Applying the Molecular Understanding of Breast Tumor McTNs to Prostate Cancer Cells.

The following Example leverages the understanding of the biochemical and biophysical mechanisms underlying McTNs (Balzer et al., Oncogene. 2010; 29(48):6402-8; Whipple et al., Cancer Research. 2008; 68(14):5678-88; Whipple et al., Experimental cell research. 2007; 313(7):1326-36. PubMed PMID: 17359970; Whipple et al., Cancer Res. 2010; 70(20):8127-37) and the advanced imaging methods we have developed (Whipple et al., Cancer Res. 2010; 70(20):8127-37; Balzer et al., Breast Cancer Res Treat. 2010; 121(1):65-78; Matrone et al., Cancer Res. 2010; 70(20):7737-41) to examine McTN generation in prostate cancer cells. A proposed wound healing model would predict that the cytoskeletal alterations that support McTNs would occur in many epithelial cancer cell types. Like breast cancer, prostate cancer predominantly arises from epithelial carcinomas (Birchmeier et al., Acta Anat. 1996; 156(3):217-26; Birchmeier W, Behrens J. Cadherin expression in carcinomas: role in the formation of cell junctions and the prevention of invasiveness. Biochimica et biophysica acta. 1994; 1198(1):11-26). Applying our McTN imaging methods to three commonly-used prostate cancer cell lines (Ln-CAP, DU145, PC3)(Kleeberger et al., Cancer Res. 2007; 67(19):9199-206; Windus et al., Experimental cell research. 2012; 318(19):2507-19) demonstrates that these cells form McTNs differentially (FIG. 13). The weakly metastatic LnCAP cell lines, which was derived from lymph node metastases demonstrates an exceptionally smooth surface, either with confocal or DIC microscopy. The more metastatic DU145 (brain met) or PC3 (bone met) cell lines have higher McTN incidences. Automated McTN analysis shows that McTN length is generally shorter in the prostate tumor cell lines compared to the HCI-001 breast tumorgraft line (compare FIGS. 12 and 13). While there is far less consensus in the prostate cancer field for effective markers of stem cell characteristics, numerous published measures show that LnCAP cells have lower stem cell markers than the DU145 and PC3 cells (Wang et al., International journal of biological sciences. 2013; 9(5):472-9; Bansal et al., The Prostate. 2014; 74(2):187-200; Hurt et al., Br J Cancer. 2008; 98(4):756-65). As shown in FIG. 13, an integrated McTN score (frequency×length×#/cell) shows much higher values for DU145 (555.0) and PC3 (1054.5) compared to LnCAP (23.4).

In addition to breast cancer cells and prostate cancer cells, McTNs are also observed in other types of cancer cells, such as colon cancer cells and B-cell lymphoma cells (for example, in HCT-116 colon cancer cell lines and Jurkat B-cell lymphoma cell lines). McTNs are likely to be found on many different types of tumor cells with metastatic potential; accordingly, the present methods can be applied to any cancer in which tumor cells display microtentacles.

Example 6

Design of Nanoscale Surface Coatings to Capture, Study and Destroy Circulating Tumor Cells.

Microtentacles are plasma membrane extensions that occur only when tumor cells are unable to form protein-based attachments (such as when they are in the bloodstream during metastasis). McTNs enable circulating tumor cells to reattach in distant tissues during metastasis and are associated with more aggressive cancer phenotypes and stem cell characteristics.

However, such non-adherent cells can be challenging to image with advanced microscopy, since they continuously drift through the field of view. Attempting to exchange the surrounding media can displace nonadherent cells, greatly increasing the challenge of adding dyes or drugs to non-adherent cells. The current example uses polyelectrolyte multilayer films to coat the imaging surface to both prevent the formation of protein-based attachments and reduce cell displacement. This technology enables tethering of nonadherent tumor cells to allow high-resolution imaging of microtentacles and measurement of time-dependent drug responses through media exchange.

Provided is a microfluidic device to rapidly image cytoskeletal dynamics in free-floating patient tumor cells. There are currently serious limitations in the ability to detect metastatic breast tumors in patients. Even the most sensitive clinical imaging methods (MRI/PET-CT) will not detect a breast tumor until it reaches a size of more than 10 million tumor cells. This means that doctors are currently unable to accurately follow early metastasis. Importantly, since most cancer drug development and clinical trials are aimed at reducing the growth of these large tumors, very little is known about how current cancer therapies are influencing tumor metastasis. In addition, these imaging limitations make it very difficult to determine by imaging methods (such as MRI) if a tumor is shrinking because the tumor is dying or because it is scattering. These two scenarios have dramatically different implications for patients. This principle is particularly critical when patients are given drugs before surgery (neoadjuvant) since these patients already harbor tumors containing millions of cells and any inadvertent dissemination must be minimized A new study that monitored circulating tumor cells (CTCs) during neoadjuvant chemotherapy showed that when CTCs increased during therapy (scattering model), there was a 25-fold higher risk of relapse in these patients within seven years. These findings emphasize that we need to improve the ability to measure early responses of patients' tumors to cancer drug treatment and understand potential impacts on metastasis.

Described herein is a new medical device (microfluidic cell tethering slide) to rapidly image live tumor cells from patients within hours of their surgery to better understand how individual patient tumors respond to cancer drugs. The device can also be used for research purposes on cultured cells. We will focus on FDA-approved therapies that target the network of cytoskeletal filaments that allow tumor cells to reattach to blood vessel walls. Since these drugs are already FDA-approved, the ability to translate these findings to the clinic will be accelerated so that the following challenges can be rapidly addressed:

Eliminate the mortality associated with metastatic breast cancer

Revolutionize treatment regimens by replacing drugs that have life-threatening toxicities with safe, effective interventions Identify what drives breast cancer growth and metastasis; identify why some breast cancers become life-threatening metastases The inventor first identified that free-floating tumor cells produce unique microtentacles (McTNs) on their surface that enable circulating tumor cells to reattach to capillary blood vessel walls in distant tissues. However, these McTNs only occur when tumor cells are free-floating and rapidly disappear when tumor cells are attached to surfaces or extracellular matrix proteins. Since McTNs are only observable in free-floating cells they were overlooked for years by studies that used attached breast tumor cells. New technologies to effectively image McTNs in patient tumor cells are needed. This invention provides means to secure the membrane of tumor cells to an imaging surface that is exceptionally thin (10 nm-100 nm) and optically clear. Tethered tumor cells continue to move dynamically as if they are free-floating, because the cell membrane is only held at a small point. The invention will enable a new microfluidic slide to capture and image McTNs on patient tumor cells to determine their responses to cytoskeletal cancer drugs. These data can be compared to how the patients' tumor cells grow and metastasize in mice (tumorgrafts), which is known to predict long-term patient outcome.

By creating and clinically testing this imaging slide for patient tumor cells, this invention provides a new early perspective on how patient tumors respond to drug treatments (in less than 24 hours). In some embodiments, the invention tests FDA-approved drugs and tests conducted on patient-isolated tumor cells. The findings can be rapidly translated to clinical treatment. The invention establishes which immediate McTN responses of the tumor cells to drugs predict metastasis in mouse tumorgrafts (which is a known indicator of eventual patient metastasis). The new device provides a platform that can be used for testing patient tumors and to improve the understanding of how to select cancer therapies that reduce metastatic risk.

The current limitations of clinical cancer imaging prevent a clear understanding of how drugs aimed at cell growth affect the metastatic potential of circulating tumor cells in patients. Recent discoveries in the inventor's lab have shown that free-floating breast tumor cells produce unique microtentacles (McTNs) that promote metastatic efficiency. Moreover, these McTNs can be detected on live patient tumor cells within hours of the surgical collection of the tumor cells from breast cancer patients. Given the rapid dynamics of McTNs, the responses of these patient-derived cells to cytoskeletal cancer drugs can be measured within one hour. Since the molecular mechanism supporting McTNs depends on microtubules (and not actin), current cancer therapies that stabilize tubulin (like taxanes and epothilones) increase McTNs and tumor cell reattachment. These results emphasize the need for improved technology to measure how current drugs affect free-floating tumor cells to better tailor cancer therapies to individual patients and reduce long-term metastatic risk.

By establishing a new microfluidic device to rapidly image live patient tumor cells in a free-floating microenvironment, this invention will advance the ability to measure circulating tumor cell behavior and response to cancer drugs. This approach will provide an immediate alternative perspective on drug responses in individual patients that can be used to guide therapy selection. In this way, the following challenges will be addressed:

Eliminate the mortality associated with metastatic breast cancer

Revolutionize treatment regimens by replacing drugs that have life-threatening toxicities with safe, effective interventions Identify what drives breast cancer growth and metastasis; identify why some breast cancers become life-threatening metastases In some aspects, the invention provides a microfluidic device to enable the rapid imaging of free-floating tumor cells removed from cancer patients (e.g., breast, prostate, colon, lymphoma, or other cancer types) during surgery or core needle biopsy, which provides an outstanding opportunity to advance clinical imaging of live patient tumor cells. With this device, we will demonstrate that the cytoskeletal dynamics and drug responses of free-floating tumor cells from breast cancer patients can be used as a rapid and early indicator of metastatic potential that can be used to guide therapy.

Specific Aims: 1) Develop non-adhesive PEM film with an integrated DNA oligo to tether free-floating tumor cells. 2) Engineer a direct lipid anchor as an alternative label-free approach to tether tumor cells. 3) Analyze patient tumor cell microtentacles and drug responses and relate to tumorgraft outcome.

In some aspects, the device uses either of two parallel PEM-based approaches (DNA or lipid) to tether tumor cells to an imaging surface while maintaining free-floating tumor cell behavior. The most effective strategy can be prioritized for the analysis of live tumor cells from 40 breast cancer patients. Parallel samples from these patients are transplanted orthotopically into immunodeficient mice. This tumorgraft approach has been demonstrated to recapitulate the metastatic behavior of the patient's original tumor far more faithfully than any tissue culture model. McTN characteristics (frequency, length, number per cell) and drug responses in individual patients can be compared to the molecular characteristics (ER/PR/HER2) of the original patient's tumor, as well as eventual growth and metastasis in the tumorgraft model.

This project establishes a new medical device and methods for imaging live patient tumor cells (e.g., breast, prostate, colon, lymphoma, and the like) within hours of surgery and identifying responses to major cancer drugs. Current treatment strategies focus largely on inhibiting tumor growth, so this technology will open a new early window on cytoskeletal dynamics in patient tumor cells and relate this data to eventual tumorgraft outcomes. Since this project will focus on FDA-approved cytoskeletal drugs, the findings can be more easily translated to impact the clinical treatment of breast cancer.

Many current cancer therapies target tumor cell division or local invasion and comparatively little is known about how to reduce distant metastasis of circulating tumor cells. Even the most sensitive clinical imaging methods are only able to detect tumors once they grow into a foci of more than 10 million tumor cells, significantly limiting the ability to determine how patient treatment strategies are affecting the metastasis of circulating tumor cells. Emerging evidence shows that while some patients benefit from chemotherapy before surgery (neoadjuvant), there are subsets of patients that rapidly progress following neoadjuvant therapy and there is a need to rapidly identify early predictors of response to neoadjuvant therapy.

The current Example focuses on the development of a novel microfluidic medical device for analyzing fresh patient tumor cells. Using this device, live patient tumor cells are imaged with confocal microscopy within hours of their removal from breast cancer patients during surgery. These patient-derived tumor cells need not be grown in vitro, reducing the potential for artificial adaptations that occur during growth in tissue culture. In parallel, the fresh patient tumor cells are transplanted orthotopically into the mammary gland of immunodeficient mice as tumorgrafts. More than any tissue culture model, such tumorgrafts are outstandingly effective at retaining the molecular characteristics of the original patient's tumor as well as serving as predictors of long-term patient prognosis and metastatic pattern. However, tumorgraft analysis can often take more than a year to complete, emphasizing the need to identify early indicators of tumorgraft characteristics.

The inventor first discovered the presence of unique microtentacles (McTNs) on the surface of free-floating breast tumor cells and have shown in a series of Cancer Research and Oncogene articles that these McTNs promote tumor cell reattachment to blood vessel endothelial cells and the retention of circulating tumor cells in lung capillaries. Importantly, existing cancer therapies can actually increase McTNs and tumor cell reattachment, raising the possibility that cancer drugs which are aimed at tumor growth might actually increase metastatic risk. For this reason, it is critical to develop new technology to rapidly define patient tumor cell drug responses so that detrimental effects of therapies on circulating tumor cell metastasis can be avoided and the most effective treatments can be prioritized. However, McTNs only occur on free-floating breast tumor cells and disappear within minutes of attachment to surfaces or extracellular matrix. This challenge necessitates the development of cell tethering technology to secure cells for imaging but not allow attachment.

The inventor has now shown that fresh patient tumor cells display McTNs within hours of tumor cell isolation by surgery and that drug responses can be gauged in these fresh cells in less than one hour. The current project describes a new microfluidic device to identify the cytoskeletal drug responses of individual patient's tumors within 24 hours and relate these responses to eventual tumorgraft growth characteristics and metastasis from 40 breast cancer patients. By developing and clinically testing this microfluidic device with a panel of FDA-approved therapies, this project can maximize the potential to rapidly translate this technology to the clinical treatment of breast cancer and other cancers.

This project provides a new microfluidic medical device to tether fresh patient tumor cells to a patterned surface for McTN imaging with confocal microscopy. Such a cell-tethering array slide will only require ~200 tumor cells from patients, an amount easily obtainable from surgical samples or even core needle biopsies. Moreover, this cell-tethering array will hold cells but prevent cell adherence to the surface so that the dynamic behavior of McTNs continues. One of the greatest challenges to McTN studies in live cells is the fact that they only occur on free-floating tumor cells and rapidly retract upon cell attachment. This particular requirement for a free-floating cell environment is a major reason why McTNs were only recently discovered, since nearly all previous studies of the breast tumor cell cytoskeleton focus on cancer cells which are attached to surfaces or extracellular matrix. However, generation of McTNs within the free-floating microenvironment of the bloodstream promotes tumor cell retention in distant capillaries, emphasizing the importance of defining how McTNs respond to current cancer therapies to help reduce metastatic potential.

The inventor first identified McTNs on the surface of free-floating breast tumor cells and developed innovative methods to image McTNs in live cells, define their molecular dependence on tubulin and establish the role of McTNs in breast tumor metastasis. Data from the inventor now shows that these imaging techniques can detect McTNs on live patient tumor cells within hours of surgery. Importantly, treatment of these patient tumor cell samples with cytoskeletal drugs yields rapid results on McTNs in less than one hour. These findings reveal a window of opportunity to use McTN dynamics to serve as a predictor of metastatic potential and drug response in individual patient tumors. Improved technology will facilitate automation of imaging live tumor cell McTNs routinely from these clinical samples.

Polyelectrolyte multilayer (PEM) films to regulate cell attachment. PEMs are exceptionally thin (10-100 nm) and can incorporate tethering molecules in their top surface, such as DNA oligos or lipids that can interact with cell membranes and hold free-floating cells without allowing cell spreading. Microcontact printing (µCP) will allow patterning of these attachment points. Tethered cells maintain the McTN dynamics and drug responses of free-floating cells, but can be held in an arrayed pattern for staining and high-resolution confocal imaging.

This invention enables the development of an innovative medical device and will yield important new information to guide breast cancer treatment.

In some aspects, the objective of this project is to develop a microfluidic device to enable the rapid imaging of free-floating tumor cells removed from breast cancer patients during surgery or core needle biopsy. In some aspects, with this microfluidic device, the invention provides that the cytoskeletal dynamics and drug responses of free-floating tumor cells from breast cancer patients can be used as a rapid and early indicator of metastatic potential. This technology can provide a critical early window on characteristics of individual patients' tumors from a free-floating perspective that is highly understudied in the field. Many of the cytoskeletal therapies we will test are already FDA-approved cytoskeletal therapies that are widely used, which will accelerate our ability to translate these findings to the clinical treatment of breast cancer. Development of the novel microfluidic device and testing of the hypothesis will follow these specific aims:

Aim 1: Develop non-adhesive PEM films with an integrated DNA oligo to tether free-floating tumor cells.
a) Test PEM film composition to inhibit attachment in a wide variety of breast tumor cell lines.
PEM films composed of PMA/PAAm will be deposited within microfluidic channels of Ibidi µ-slideVI0.4 6-channel slides. Breast tumor cell attachment to two index breast tumor cell lines (MDA-436, MCF-7) will be used to confirm reduced attachment. PLL/PGA multilayer will serve as an alternative in case of technical difficulty with PMA/PAAm. This subaim will produce 10 PEM-coated devices. Initial PEM designs and characterization (e.g., stability, surface roughness) will also be carried out on coated planar substrates to support extension to the Ibidi slides.
Microfluidic slides will be tested against a broader panel of 10 human breast tumor cell lines and imaged with live-cell confocal microscopy. Comparison of cytoskeletal dynamics in these cell lines to published results will be used to confirm tumor cell behavior. Adhesion will be tested by media exchange and automated hemocytometer count.
Milestones:
Generate microfluidic devices with both PMA/PAAm and PLL/PGA multilayer films.
Identify PEMs that prevent tumor cell attachment for 4 hours in 10 cell line panel. (Priority: PMA/PAAm).
b) Validate PEM-mediated attachment inhibition with patient-derived cells (fresh surgical and tumorgraft).
Fabricate and characterize devices with channels coated with the optimal PEM identified in Aim 1a.
Existing tumorgraft cell lines and fresh surgical samples will be used to test adhesion of more complex clinical cell mixtures to PEM films. Optimize tumor cell identification methods (EpCAM/CD45, CK8/18) for use in microfluidic slides.
Milestones:
Fabricate 15 devices for clinical analysis with non-adhesive PEM.
Test non-adhesive PEM with 10 tumorgraft samples and 5 fresh clinical samples.
c) Integrate a DNA oligo for membrane tethering into the upper layer of the PEM surface.
Use published methods to integrate a DNA oligo into the top layer of the PEM film. Validate DNA integration with a fluorescent complementary DNA oligo. Characterize interactions (e.g., stability, binding affinity).
Test tethering approaches with PEM-DNA devices with 10 human breast tumor cell lines and quantitate cell attachment with automated hemocytometer counts. Validate tethering technology with 4 tumorgraft and 4 fresh clinical samples.
Milestones:
Confirm DNA oligo integration into PEM microfluidic device. Fabricate 15 PEM-DNA test devices.
Test DNA tethering with breast tumor cell lines in Jewell lab and Martin lab.
Aim 2: Engineer a direct lipid anchor as an alternative label-free approach to tether tumor cells.
a) Design lipid tethers to support McTNs on cells without use of DNA oligos or other additives (label-free).
Compare two different glycerophospholipids (18:O-LysoPG and 15:O(3)-16:1-CA) for integration into PEM film in microfluidic channels. Optimization of lipid integration conditions to allow tethering of two breast tumor cell lines (MDA-436 and MCF-7).
Testing of lipid-coated PEMs for tethering in 10 breast tumor cell lines, 4 tumorgrafts and 4 fresh clinical samples.
Milestones:
Develop a lipid anchor for tethering cells to the PEM film. Fabricate 10 PEM-lipid devices.
Validate lipid tethering technique with a panel of breast tumor cell lines, tumorgrafts and patient cells.
b) Use µCP to generate lipid islands of 5-10 µm in diameter for single-cell tethering.
Use microcontact printing in the UMCP nanofabrication facility (Fablab) to print 5-10 mm spots functionalized with lipid anchors on PEM-coated coverglass. Screen in 2 tumor cells lines. Fabricate 24 optimized devices using adhesive microfluidic channels (Sticky-slide, Ibidi) for testing.
Test lipid-printed PEM slides for localized adhesion of 10 human breast tumor cell lines, 4 tumorgrafts and 4 fresh samples of patient tumor cells.
Milestones:
Deposit lipid anchor in a localized manner on PEM films.
Validate localized tethering with panel of tumor cell lines and patient-derived cell mixtures.
c) Develop photoactivatable lipid anchor for lithography directly in microfluidic channels.
Test strategies to allow photoactivation of lipid anchor adhesiveness. Coordinate with Avanti Polar Lipids to contract lipid modifications. Generate photolithography masks in Fablab with pattern features of 7 µm islands with a 40 µm spacing. Characterize mechanical robustness of photoactive PEMs and optimize to maximize cell/tether interactions using 2 cells lines. Fabricate 24 devices within intact Ibidi microfluidic slides for testing in the Martin lab. Martin lab: Test optimized photoactivated lipid-PEM slides for localized adhesion of 10 human breast tumor cell lines, 4 tumorgrafts and 4 fresh patient samples.
Milestones:
Generate and optimize photoactivatable lipid.
Prepare photolithography mask for microfluidic slide geometry.
Fabricate 24 optimized devices with photoactivated lipid islands within microfluidic channels.
Validate localized tethering with panel of tumor cell lines and patient-derived cell mixtures.
Aim 3: Analyze patient tumor cell microtentacles and drug responses and relate to tumorgraft outcome.
a) Compare efficiency of 2 PEM devices for tethering patient-derived tumorgraft cells.
Generate 10 devices each using i) PEM-DNA tethers and ii) PEM-lipid tethers.
Compare PEM-DNA and PEM-lipid devices for tethering and retention of tumorgraft cell lines and fresh patient samples with automated hemocytometer counting.
Milestones:
Fabricate 20 devices for testing in Martin lab (10 PEM-DNA, 10 PEM-lipid).
Validate lipid tethering technique with a panel of 4 tumorgrafts and 4 patient tumor cell samples.
b) Expand analysis with prioritized device to 40 patients for McTN analysis and drug response studies.
Generate 48 devices with PEM tethering strategy selected in Aim 3a.
Use devices supplied by Jewell lab to test fresh tumor cell preparations from 40 breast cancer patients. Each patient's cells will be characterized for McTN frequency (#1100 cells), average McTNs per cell and average McTN length under the following conditions for 1 hour: (untreated, vehicle, Paclitaxel, Ixabepilone, Vinblastine, Colchicine, Parthenolide, Curcumin) This will require one slide per patient, as untreated and vehicle datasets will be collected first before drug treatments and all drugs will be tested simultaneously in the six channels. An automated microscope stage will collect images from each channel every 5 minutes across the one hour drug treatment.

Milestones:

Fabricate 48 devices with the prioritized tethering strategy for clinical use.

Collect data on WIN dynamics and drug response in cells and tumorgrafts from 40 breast cancer patients.

c) Analyze patient tumor cell microtentacles and drug responses and relate to tumorgraft outcome.

Provide feedback on relating McTN characteristics to patient outcome. Assistance with MatLab methods to optimize methods for measuring McTN metrics (frequency, avg. per cell, avg. length). Discussions and feedback with publications arising from the studies.

Work with Biostatistics shared service of the Greenebaum Cancer Center to relate McTN metrics and drug responses to tumorgraft outcome (growth rate, metastatic efficiency, metastasis site). Begin to relate de-identified patient outcome data to McTN metrics and drug responses. Work with Translational core laboratory to add McTN metrics to de-identified breast cancer patient-tumorgraft outcome database.

Milestones:

Use data gathered with PEM device and live cell imaging to compare McTN metrics to tumorgraft outcome.

Conduct analysis of McTN metrics to patient tumor characteristics outcome.

Conduct preliminary analysis of McTN metrics to patient outcome.

Add McTN metrics to de-identified patient-tumorgraft database.

Breast tumor metastasis is currently very difficult to monitor with clinical imaging and therefore our understanding of how drug treatments affect metastasis is poorly understood (Dogan B E, Turnbull L W (2012). Annals of oncology: official journal of the European Society for Medical Oncology/ESMO 23 Suppl 6: vi23-29; Marino et al., The American journal of pathology 183: 1084-1095). Cancer drug development focuses on inhibiting growth or invasion of attached tumor cells and largely overlooks drug effects on circulating tumor cells (CTCs) in the free-floating microenvironment of the bloodstream (Kim et al., Nat Rev Clin Oncol 6:587-595; Le et al., (2011). Cancer biology & therapy 12; Patel et al., (2013) Oncogene). This could be an important clinical blind-spot since surgery and neoadjuvant chemotherapy can dramatically increase levels of CTCs if every primary tumor cell is not successfully removed or destroyed (Momma et al., Cancer Res 58: 5425-5431; Goldfarb Y, Ben-Eliyahu S (2006). Surgery as a risk factor for breast cancer recurrence and metastasis: mediating mechanisms and clinical prophylactic approaches. Breast Dis 26: 99-114). This invention will develop a new microfluidic medical device to specifically test the drug responses of free-floating breast tumor cells from individual patients to model how such drug treatments will affect the metastatic reattachment potential of CTCs. Past approaches have prevented these studies because the function and morphology of tumor cells change upon adhesion (Balzer E M, Whipple R A, Thompson K, Boggs A E, Slovic J, Cho E H et al (2010). c-Src differentially regulates the functions of microtentacles and invadopodia. Oncogene 29: 6402-6408; Yamaguchi H, Wyckoff J, Condeelis J (2005). Cell migration in tumors. Current opinion in cell biology 17: 559-564), defining a need for the novel biomaterial and microfluidic approach we propose to tether free-floating tumor cells without altering their dynamic movements. This new perspective on the drug responses of individual patient tumor cells will help ensure that cancer drugs aimed at cell division and local invasion to not inadvertently increase metastatic risk and help identify safer, more effective therapies for each patient. In this way, we will address the following overarching challenges:

Eliminate the mortality associated with metastatic breast cancer.

Revolutionize treatment regimens by replacing drugs that have life-threatening toxicities with safe, effective interventions.

Identify what drives breast cancer growth and metastasis; identify why some breast cancers become life-threatening metastases.

2) Background

Current clinical imaging only effectively detects large, focal breast tumors1, producing a critical blind spot for how cancer therapies could affect early metastasis2. Even the most sensitive clinical imaging methods (MRI/PET-CT) can only detect a foci of approximately 10 million tumor cells10, emphasizing that both current drug development and patient monitoring are overlooking effects on tumor cells below this clinical detection threshold. This imaging limitation is particularly important with neoadjuvant setting, where patients already harbor tumors with millions of cells and are administered cancer drugs prior to tumor removal surgery.

Figure 5:
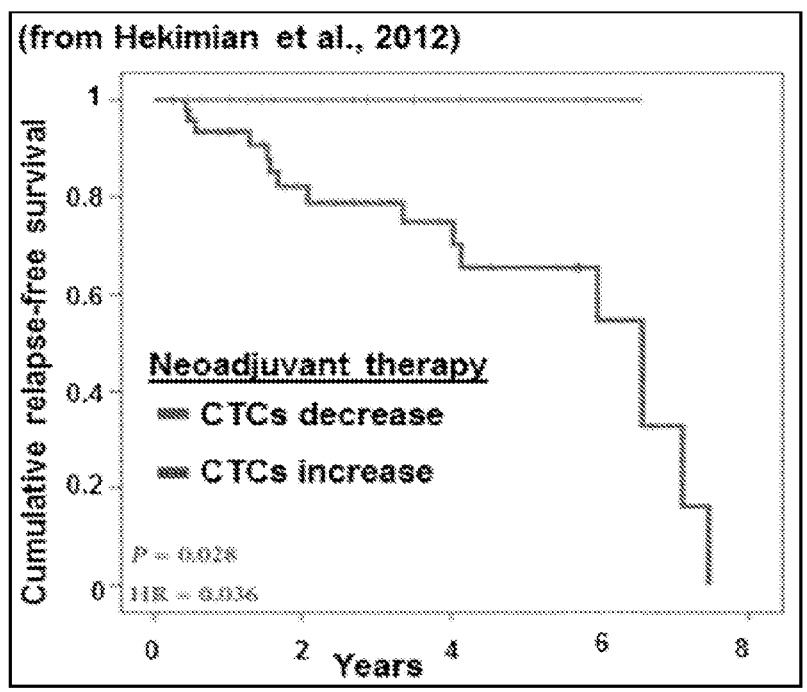
FIG. 5. Poor recurrence-free survival when CTCs increase during neoadjuvant chemotherapy. Patients whose CTC levels decrease during neoadjuvant chemotherapy have a 100% recurrence-free survival after 7 years (upper line). In stark contrast, patients whose CTC levels increase during neoadjuvant therapy have only a 4% recurrence-free survival after 7 years (lower line).

While some patients clearly show tumor response from neoadjuvant chemotherapy (Redden et al., (2013). The Surgical clinics of North America 93: 493-499; von Minckwitz et al., (2011). Breast 20 Suppl 3: S142-145), the overall survival benefit is fairly limited (Davidson et al., (2005) Journal of the National Cancer Institute 97: 159-161) and some patients unfortunately rapidly progress (Caudle et al. (2010). Journal of Clinical Oncology 28: 1821-1828; Caudle et al., Annals of Surgical Oncology 18: 932-938). There is clearly a need to identify which patients will benefit most from specific neoadjuvant treatments. During neoadjuvant therapy, it would be very difficult to distinguish by clinical imaging whether a tumor is shrinking because it is dying or because the tumor is scattering. These two scenarios have dramatically different implications for the patient. Recent studies monitoring circulating tumor cells (CTCs) in breast cancer patients receiving neoadjuvant chemotherapy (FIG. 5) (Hekimian et al., (2012). ISRN Oncology 2012: 601810) show that in patients where CTCs increase in the bloodstream during therapy, only 4% of these patients were relapse-free after 7 years. Strikingly, 100% of patients whose CTCs decreased during therapy remained relapse-free at 7 years. This 25-fold increased risk of relapse when CTCs increase during therapy clearly emphasizes the importance of understanding how current cancer drugs could affect free-floating CTCs. These results and the current limitations of clinical imaging highlight the need to better understand the mechanisms that influence CTC metastasis in individual patients to effectively guide therapy (Li et al., (2008). Journal of Applied Clinical Medical Physics/American College of Medical Physics 9: 2781).

Figure 6:
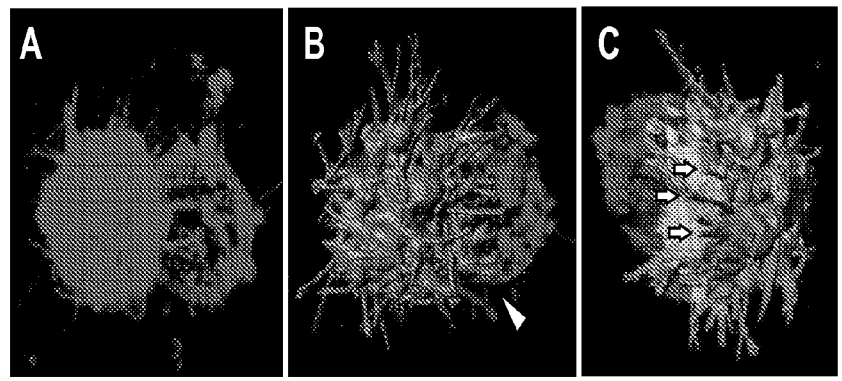
FIG. 6. McTNs promote tumor cell aggregation. A) Detached MDA-436 breast tumor cells were labeled with the lipophilic membrane dye CellMask. When mixed with a population of cells transiently transfected with GFP, this allows specific tracking of the McTNs that encircle neighboring cells during aggregation (B and C, arrowhead). Rotation of the confocal image indicates McTNs bind along surface of adjacent cells.
Figure 7:
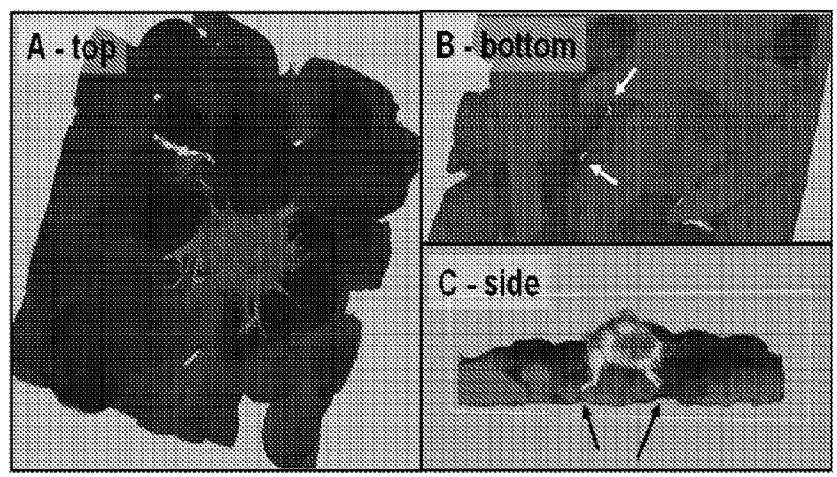
FIG. 7. McTNs promote penetration of endothelial monolayers. A) Live MDA-436 cells expressing membrane-localized GFP were suspended over endothelial monolayers expressing mCherry. Confocal imaging as the cell attaches discerns the penetration of the tumor cell through the layer when viewed from underneath (B, white arrows) or in cross-section (C, black arrows). We will use this high-resolution imaging technique to examine the how altering tubulin detyrosination and Tau affects McTN generation and endothelial binding in this live-cell in vitro model of tumor cell extravasation.
Figure 11:
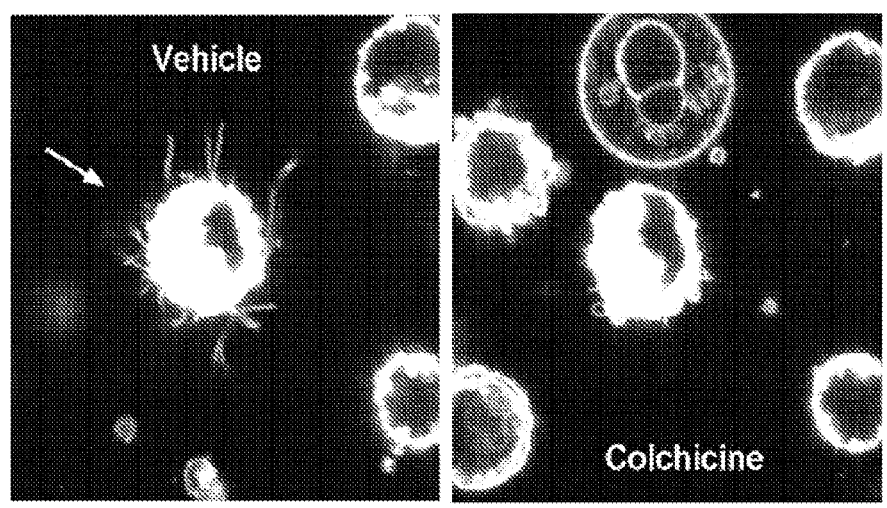
FIG. 11. Drug responses can be measured quickly in patient-derived tumor cells (30 minute Colchicine response)

Free-floating breast tumor cells produce microtentacles (McTNs) that can now be imaged in live tumor cells freshly-isolated from breast cancer patients. Studies pioneered by the Martin lab have identified that mammary epithelial and breast carcinoma cells produce unique microtentacles (McTNs) on their plasma membrane when detached from extracellular matrix (Whipple R A, Balzer E M, Cho E H, Matrone M A, Yoon J R, Martin S S (2008). Vimentin filaments support extension of tubulin-based microtentacles in detached breast tumor cells. Cancer Res 68: 5678-5688; Whipple R A, Cheung A M, Martin S S (2007). Detyrosinated microtubule protrusions in suspended mammary epithelial cells promote reattachment. Experimental cell research 313: 1326-1336). These microtentacles occur with higher frequency in metastatic breast tumor cell lines (FIG. 1A). Unlike the actin-based invadopodia and filopodia that are well-characterized in tumor cells attached to extracellular matrix, McTNs are based on microtubule extension and actively suppressed by contraction of the actin cortex beneath the plasma membrane (Matrone M A, Whipple R A, Balzer E M, Martin S S (2010). Microtentacles tip the balance of cytoskeletal forces in circulating tumor cells. Cancer Res 70: 7737-7741). McTNs can encircle adjacent cells promoting reattachment of tumor cells to each other (FIG. 6B) and endothelial cells that compose blood vessel walls (FIG. 7A) (Whipple R A, Balzer E M, Cho E H, Matrone M A, Yoon J R, Martin S S (2008). Vimentin filaments support extension of tubulin-based microtentacles in detached breast tumor cells. Cancer Res 68: 5678-5688; Whipple R A, Cheung A M, Martin S S (2007). Detyrosinated microtubule protrusions in suspended mammary epithelial cells promote reattachment. Experimental cell research 313: 1326-1336), as well as increasing the retention of circulating tumor cells in the lungs of mice (Balzer E M, Whipple R A, Thompson K, Boggs A E, Slovic J, Cho E H et al (2010). c-Src differentially regulates the functions of microtentacles and invadopodia. Oncogene 29: 6402-6408.; Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. Oncogene 29: 3217-3227.). Recent preliminary data now demonstrate that McTNs can be imaged in fresh tumor cells from breast cancer patients (FIG. 11) and that responses of McTNs to drug treatments can be judged in less than one hour (FIG. 11). In contrast to current technology, this imaging method can be conducted on <200 patient tumor cells and does not require any in vitro expansion that imposes selective pressures in cultured cell growth.

There is currently an overwhelming focus of the tumor biology field on cells that are attached to flattened or 3-dimensional extracellular matrix proteins (Yamaguchi H, Wyckoff J, Condeelis J (2005). Cell migration in tumors. Current opinion in cell biology 17: 559-564; Fischbach C, Chen R, Matsumoto T, Schmelzle T, Brugge J S, Polverini P J et al (2007). Engineering tumors with 3D scaffolds. Nature methods 4: 855-860), which limits the understanding of cytoskeletal dynamics in free-floating CTCs. Studies using intravital microscopy have shown that the ability of tumor cells to adhere to capillary endothelial cells while circulating in vivo depends on tubulin and not actin (Korb T, Schluter K, Enns A, Spiegel H U, Senninger N, Nicolson G L et al (2004). Integrity of actin fibers and microtubules influences metastatic tumor cell adhesion. Experimental cell research 299: 236-247). While these studies were conducted at a macroscopic level, the mechanism by which CTCs bind blood vessel walls in vivo therefore aligns precisely with the mechanisms underlying the McTNs in detached tumor cells (Whipple R A, Balzer E M, Cho E H, Matrone M A, Yoon J R, Martin S S (2008). Vimentin filaments support extension of tubulin-based microtentacles in detached breast tumor cells. Cancer Res 68: 5678-5688; Whipple R A, Cheung A M, Martin S S (2007). Detyrosinated microtubule protrusions in suspended mammary epithelial cells promote reattachment. Experimental cell research 313: 1326-1336; Matrone M A, Whipple R A, Balzer E M, Martin S S (2010). Microtentacles tip the balance of cytoskeletal forces in circulating tumor cells. Cancer Res 70: 7737-7741).

Figure 2:
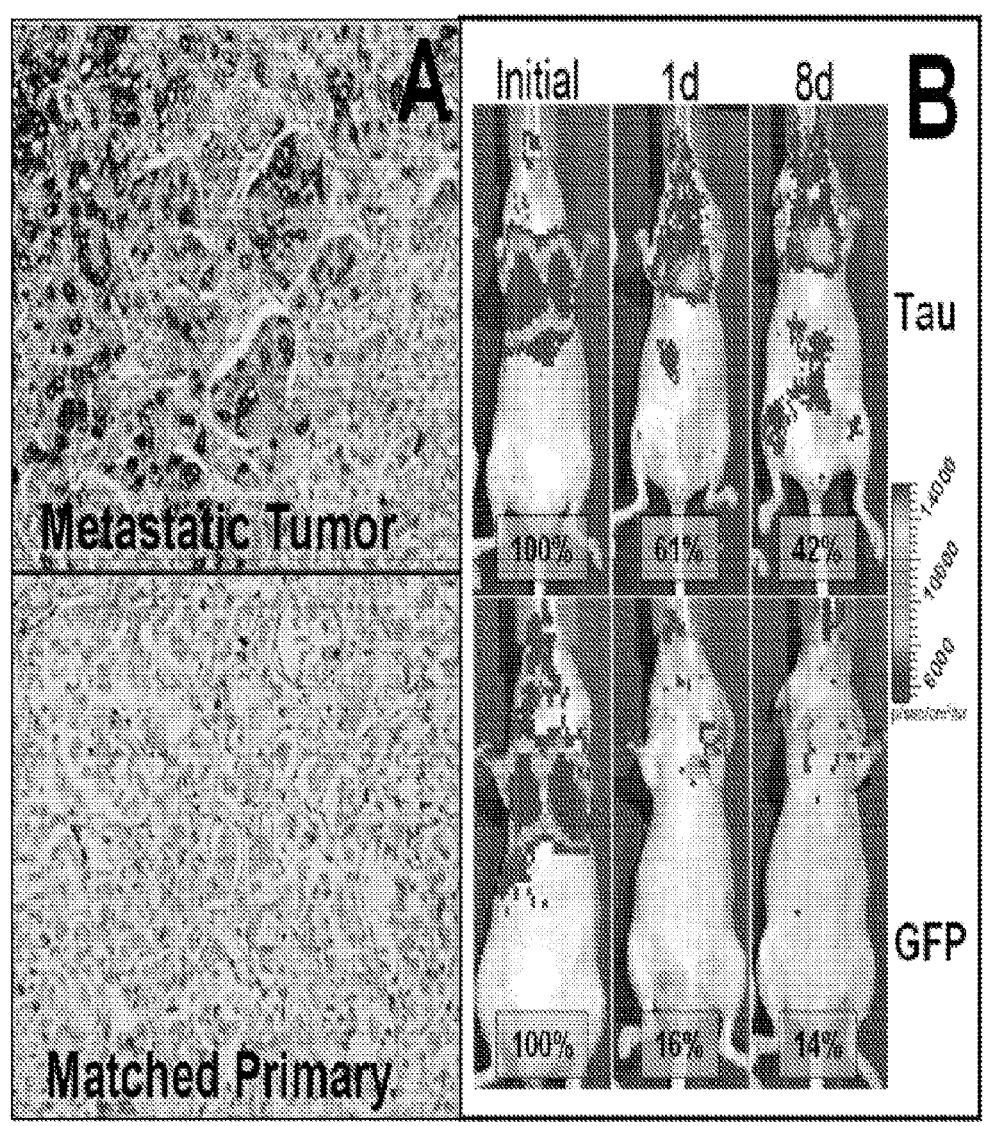
FIG. 2. The microtubule-stabilizing Tau protein is elevated in metastatic tumors and increases lung retention of injected tumor cells. A) Immunohistochemistry for expression of the Tau microtubule-stabilizing protein in 102 matched primary and metastatic tumors showed a specific upregulation of Tau in 53% of metastatic tumors, suggesting that microtubule stabilization provides a selective advantage to metastatic tumor cells. B) MCF7 human breast tumor cells were stably transfected with firefly luciferase and either Tau or the vector control containing GFP. Tail vein injection of $5 \times 10^5$ cells demonstrates equal initial lung retention, but after 1 or 8 days the MCF7 cells expressing Tau are retained more efficiently in the lung (values=avg. luminescence normalized to initial value for each mouse, n=6, P<0.05, t-test). These data demonstrate that genetically-induced microtubule stabilization that promotes McTNs can increase the ability of CTCs to reattach in distant tissues.
Figure 3:
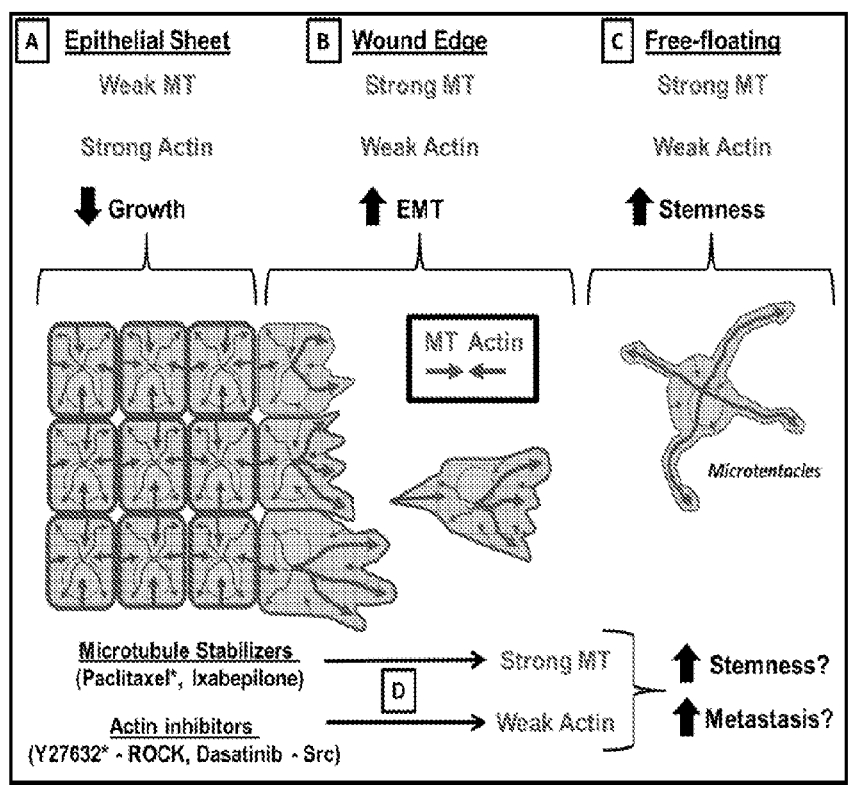
FIG. 3. Cancer drugs can mimic the cytoskeletal effects of wound healing and detachment. A) Epithelial cells within a barrier layer possess relatively weak microtubules expanding from the cell center that are counteracted by strong contraction of the actin filaments that form a cortical layer beneath the cell surface at cell-cell contacts. B) When an epithelial layer is scratched or wounded, cell-cell mediated actin contraction is reduced and microtubules become stabilized toward the wound, helping direct cells to reseal the epithelial barrier by moving into the wound. Epithelial cells at the wound edge also undergo an epithelial-to-mesenchymal transition (EMT) that induces increased stem cell characteristics. C) This wounding effect is even more pronounced when epithelial cells become fully detached (FIG. 3C), and the reinforcement of microtubules and weakening of actin yields unique microtentacles (McTNs) that promote epithelial cell aggregation and reattachment. This cytoskeletal imbalance response may explain why one of the most reliable ways to promote stem cell growth is floating culture. D) In support of this model, publications in the past year have shown that drugs which inhibit actin contraction or stabilize microtubules can directly induce stem cell characteristics (*).
Figure 4:
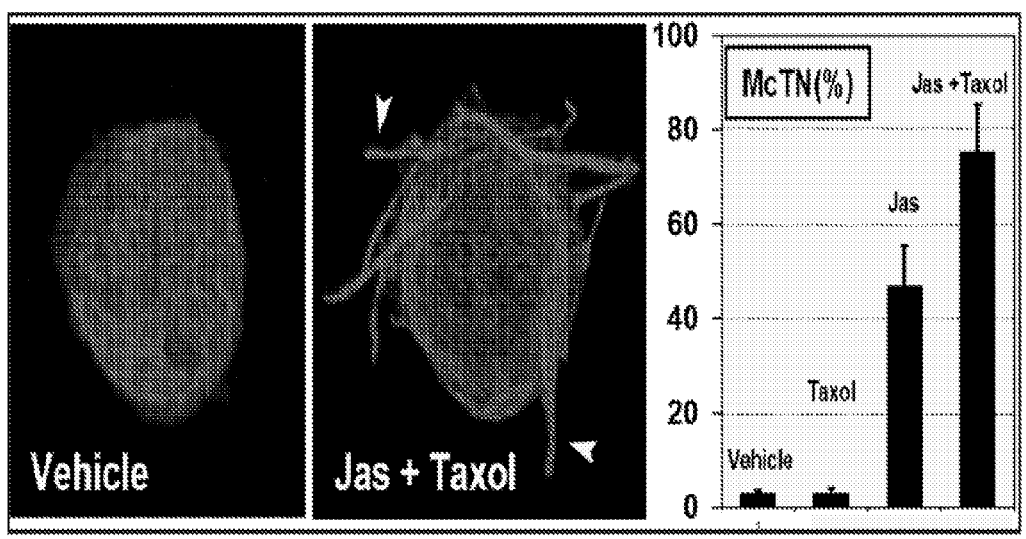
FIG. 4. Targeting cell division can increase McTNs. Treatment of nonmetastatic SkBr3 cells with drugs that prevent cell growth by reducing actin (Jas, 500 nM) and stabilizing microtubules (Paclitaxel-Taxol, 1.2 µM), increases levels of McTNs dramatically, when imaged with confocal microscopy for tubulin localization (white arrows). These data raise concern that some drugs which inhibit cell division could actually increase metastatic potential. (Bars=mean+S.D from 3 expts. with McTNs scored blindly).

Genetic alterations and chemotherapies that stabilize tubulin can increase McTNs. Actin-disrupting drugs, such as jasplakinolide (Jas) are currently being developed as therapies to reduce tumor cell division and migration (Takeuchi H, Ara G, Sausville E A, Teicher B (1998). Jasplakinolide: interaction with radiation and hyperthermia in human prostate carcinoma and Lewis lung carcinoma. Cancer chemotherapy and pharmacology 42: 491-496). Likewise, tubulin-stabilizing drugs (Paclitaxel) are valued for their suppressive effect on dividing cells (Morris P G, Fornier M N (2008). Microtubule active agents: beyond the taxane frontier. Clin Cancer Res 14:7167-7172). However, the combination of Jas and Taxol increased McTNs dramatically in nonmetastatic SkBr3 cells (FIG. 4, white arrows) (Balzer E M, Whipple R A, Cho E H, Matrone M A, Martin S S (2010). Antimitotic chemotherapeutics promote adhesive responses in detached and circulating tumor cells. Breast Cancer Res Treat 121: 65-78). Blinded McTN scoring shows the strength of this response in tumor cell populations and emphasizes the importance of considering how therapies targeting cell division could affect CTCs25. While the concentration of Paclitaxel (1.2 µM) that promotes McTNs is higher than that used to inhibit cell division, it is worth noting that a routine clinical dose (175 mg/m2) yields blood levels of >60 µM Paclitaxel that do not decrease below 1.2 µM until 6 hours after infusion (Bulitta J B, Zhao P, Arnold R D, Kessler D R, Daifuku R, Pratt J et al (2009). Mechanistic population pharmacokinetics of total and unbound paclitaxel for a new nanodroplet formulation versus Taxol in cancer patients. Cancer chemotherapy and pharmacology 63: 1049-1063. CTCs travel from primary tumors to distant tissues within minutes (Chambers A F, Groom A C, MacDonald I C (2002). Dissemination and growth of cancer cells in metastatic sites. Nature reviews Cancer 2: 563-572), providing ample opportunity for Paclitaxel treatment to influence CTC retention. We have published that genetic alterations which promote McTNs (FIG. 2B) increase CTC lung retention in living mice (Balzer E M, Whipple R A, Thompson K, Boggs A E, Slovic J, Cho E H et al (2010). c-Src differentially regulates the functions of microtentacles and invadopodia. Oncogene 29: 6402-6408; Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. Oncogene 29: 3217-3227).

Figure 17:
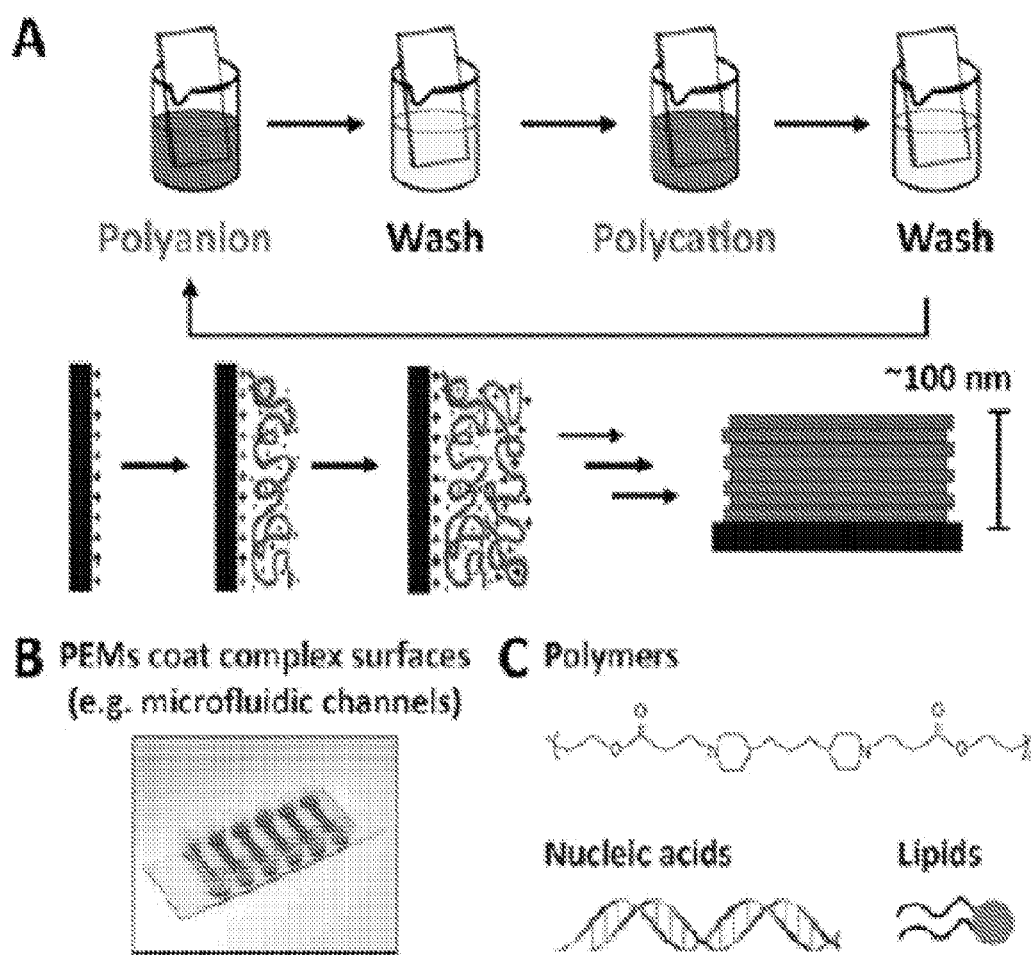
FIG. 17. Polyelectrolyte multilayer (PEM) films as ultra-thin surface coatings. A) Sequential exposure of surfaces to polycation and polyanion solutions generates multilayer films. B) PEMs can be deposited on complex geometries such as microfluidic channels. C) Coatings can be assembled from synthetic or natural components, allowing tuning of CTC adhesion by modifying PEMs with DNA or lipids.

Polyelectrolyte multilayer (PEM) films provide a tunable surface for tethering and imaging CTCs. Adsorption of alternating layers of polycationic and polyanionic solutions to surfaces can be used to generate polyelectrolyte multilayers (PEM) that assemble through electrostatic or hydrogen bonding (FIG. 17A). These films are ultrathin (10-100 nm), optically clear, and use a simple all-aqueous approach based on sequential exposure of a target surface or substrate to the polyelectrolyte solutions. This feature allows simple deposition of films on complex surface geometries, including microfluidic channels (FIG. 17B). Furthermore, this platform allows assembly from a robust combination of synthetic polymers and biological molecules such as nucleic acids, lipids, proteins (FIG. 17C). We will exploit this unique benefit to tune the cytophilicity of PEM surfaces to adjust and maintain McTNs persistence on CTCs adhered to PEMs (Saurer E M, Jewell C M, Roenneburg D A, Bechler S L, Torrealba J R, Hacker T A et al (2013). Polyelectrolyte multilayers promote stent-mediated delivery of DNA to vascular tissue. Biomacromolecules 14: 1696-1704; Jewell C M, Lynn D M (2008). Multilayered polyelectrolyte assemblies as platforms for the delivery of DNA and other nucleic acid-based therapeutics. Advanced drug delivery reviews 60: 979-999; Jewell C M, Zhang J, Fredin N J, Wolff M R, Hacker T A, Lynn D M (2006). Release of plasmid DNA from intravascular stents coated with ultrathin multilayered polyelectrolyte films. Biomacromolecules 7: 2483-2491; Jewell C M, Zhang J, Fredin N J, Lynn D M (2005). Multilayered polyelectrolyte films promote the direct and localized delivery of DNA to cells. Journal of controlled release: official journal of the Controlled Release Society 106: 214-223). In addition, numerous approaches can be used to integrate DNA oligos into the top surfaces of PEM multilayers (Saurer E M, Jewell C M, Roenneburg D A, Bechler S L, Torrealba J R, Hacker T A et al (2013). Polyelectrolyte multilayers promote stent-mediated delivery of DNA to vascular tissue. Biomacromolecules 14: 1696-1704; Jewell C M, Zhang J, Fredin N J, Lynn D M (2005). Multilayered polyelectrolyte films promote the direct and localized delivery of DNA to cells. Journal of controlled release: official journal of the Controlled Release Society 106: 214-223; Flessner R M, Jewell C M, Anderson D G, Lynn D M (2011). Degradable polyelectrolyte multilayers that promote the release of siRNA. Langmuir: the ACS journal of surfaces and colloids 27: 7868-7876) which can be used for controlled cell transfection with plasmids or gene silencing with siRNA. Recent studies have shown that free-floating cells can be tethered to surfaces by integrating DNA oligos into the cell membrane with a hydrophobic lipid tail and hybridizing with a complementary DNA strand placed on a surface that has been passivated to prevent cell spreading (Onoe H, Hsiao S C, Douglas E S, Gartner Z J, Bertozzi C R, Francis M B et al (2012). Cellular microfabrication: observing intercellular interactions using lithographically-defined DNA capture sequences. Langmuir: the ACS journal of surfaces and colloids 28: 8120-8126; Selden N S, Todhunter M E, Jee N Y, Liu J S, Broaders K E, Gartner Z J (2012). Chemically programmed cell adhesion with membrane-anchored oligonucleotides. Journal of the American Chemical Society 134: 765-768). Such membrane-tethered cells are incapable of using the lipid-based attachment to organize their cytoskeleton, so they maintain a free-floating cell behavior. The present invention provides a cytophobic surface coating that integrates a cell membrane tether to improve the analysis of free-floating breast tumor cell behavior and drug responses.

In some aspects, the present invention provides a microfluidic device to enable the rapid imaging of free-floating tumor cells removed from breast cancer patients during surgery or core needle biopsy. With this device, the cytoskeletal dynamics and drug responses of free-floating tumor cells from breast cancer patients can be used as a rapid and early indicator of metastatic potential that can be used to guide therapy. Two parallel PEM-based approaches (DNA tethering and lipid microcontacting printing) will identify the most effective biomaterial strategy. The potential to use this immediate cytoskeletal analysis in free-floating tumor cells as an early predictor of metastasis in the highly clinically-relevant, but longer-term tumorgraft model (Onoe H, Hsiao S C, Douglas E S, Gartner Z J, Bertozzi C R, Francis M B et al (2012). Cellular micro fabrication: observing intercellular interactions using lithographically-defined DNA capture sequences. Langmuir: the ACS journal of surfaces and colloids 28: 8120-8126; Selden N S, Todhunter M E, Jee N Y, Liu J S, Broaders K E, Gartner Z J (2012). Chemically programmed cell adhesion with membrane-anchored oligonucleotides. Journal of the American Chemical Society 134: 765-768) and the ability to rapidly gauge patient tumor cell drug responses highlight the advances that could be made with this technology.

Specific Aims

Aim 1: Develop non-adhesive PEM film with an integrated DNA oligo to tether free-floating tumor cells. Polyelectrolyte multilayers can form exceptionally thin films (10-100 nm) that prevent cell attachment while remaining optically clear (Sun B, Jewell C M, Fredin N J, Lynn D M (2007). Assembly of multilayered films using well-defined, end-labeled poly(acrylic acid): influence of molecular weight on exponential growth in a synthetic weak polyelectrolyte system. Langmuir: the ACS journal of surfaces and colloids 23: 8452-8459). Since PEM films can be formed simply through sequential exposure of solutions to the substrate (Jewell C M, Lynn D M (2008). Multilayered polyelectrolyte assemblies as platforms for the delivery of DNA and other nucleic acid-based therapeutics. Advanced drug delivery reviews 60: 979-999), we will coat microfluidic slides with a PEM that prevents tumor cell attachment to enable the study of free-floating cell behavior. To allow rapid fluorescent staining and drug treatments while maintaining this free-floating state, we will use an integrated DNA oligo to tether the tumor cell membrane to a PEM film (Selden N S, Todhunter M E, Jee N Y, Liu J S, Broaders K E, Gartner Z J (2012). Chemically programmed cell adhesion with membrane-anchored oligonucleotides. Journal of the American Chemical Society 134: 765-768).

a) Test PEM film composition to inhibit attachment in a wide variety of breast tumor cell lines (10 lines).
b) Validate PEM-mediated attachment inhibition with patient-derived cells (fresh surgical and tumorgraft).
c) Integrate a DNA oligo for membrane tethering into the upper layer of the PEM surface.

Aim 2: Engineer a direct lipid anchor as an alternative label-free approach to tether tumor cells. This aim will generate precise 5-10 µm lipid points of attachment to tether cells without requiring the addition of transient membrane surface labels to tumor cells (i.e., DNA). Bypassing DNA-labeling will allow direct application of clinical samples to the tethering array with dramatically reduced cell numbers compared to the requirements for DNA labeling (~$10^7$ cells/ml) (Selden N S, Todhunter M E, Jee N Y, Liu J S, Broaders K E, Gartner Z J (2012). Chemically programmed cell adhesion with membrane-anchored oligonucleotides. Journal of the American Chemical Society 134: 765-768). This one-step lipid array will also reduce the number of cells needed from patient samples because the entire volume of the microfluidic channel is 304, allowing viewing of all patient cells in a single channel. Initial tests with breast tumor cell lines show that reproducible McTN counts can be obtained from as few as 200 cells per channel, increasing the feasibility that this analysis could even be conducted on core needle biopsy samples, which routinely yield between 2,000 and 10,000 tumor cells (Stoler D L, Stewart C C, Stomper P C (2002). Breast epithelium procurement from stereotactic core biopsy washings: flow cytometry-sorted cell count analysis. Clin Cancer Res 8: 428-432).

a) Design lipid tethers for cells without use of DNA oligos or other additives (label-free).
b) Use microcontact printing (µCP) to generate lipid islands of 5-10 µm in diameter for single-cell tethering.
c) Develop photoactivatable lipid anchor for lithography directly in microfluidic channels.

Aim 3: Analyze patient tumor cell microtentacles and drug responses and relate to tumorgraft outcome.

The most effective PEM microfluidic device (DNA-Aim 1 or Lipid-Aim 2) will be prioritized to analyze microtentacles on freshly-derived tumor cells from 40 patients and their responses to 6 common and emerging cytoskeletal cancer drugs that either increase microtubule stabilization and McTNs (Paclitaxel, Ixabepilone) or decrease microtubule stabilization and McTNs (Colchicine, Parthenolide, Vinblastine, Curcumin).

a) Determine efficiency of 2 PEM devices (DNA or lipid) for tethering patient-derived tumorgraft cells.
b) Expand analysis with prioritized device to 40 patients for McTN analysis and drug response studies.
c) Compare tumorgraft outcome (growth rate, metastasis and organ of colonization) to live-cell data from fresh-patient samples and tumorgrafts (McTN metrics and drug responses).

5) Research Strategy

Figure 18:
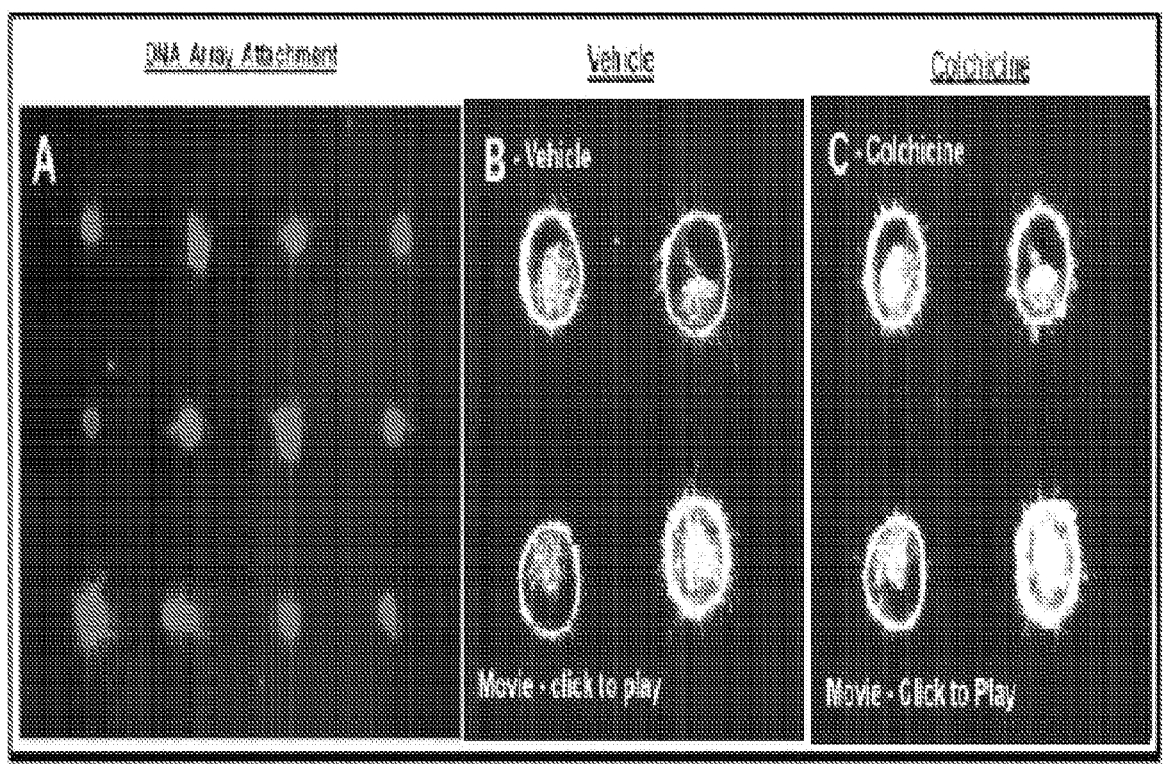
FIG. 18. DNA-lipid tethering of breast tumor cells maintains free-floating cell behavior. A) The DNA labeling technique can be used to pattern CTCs on planar surfaces), creating a platform to monitor McTN dynamics in arrayed cells (B) and the impact of drug exposure (C) in real-time.

Specific Aim 1: Develop non-adhesive PEM film with integrated DNA oligo to tether free-floating tumor cells.
Rationale: It is possible to tether breast tumor cells to surfaces using a DNA-lipid anchor (FIG. 18).

Such tethered cells can be attached in specific patterns and maintain the dynamic behavior of free-floating tumor cells, including McTN formation. In addition, solutions can be passed over the cells to allow cell surface staining and the application of drugs without significantly disrupting cell tethering or displacing cells.

Building on our expertise and the PEM literature (Yang S Y, Mendelsohn J D, Rubner M F (2003). New class of ultrathin, highly cell-adhesion-resistant polyelectrolyte multilayers with micropatterning capabilities. Biomacromolecules 4: 987-994; Kohli N, Vaidya S, Ofoli R Y, Worden R M, Lee I (2006). Arrays of lipid bilayers and liposomes on patterned polyelectrolyte templates. J Colloid Interface Sci 301: 461-469), we have designed and tested 6 PEM bilayer compositions to control breast tumor cell adhesion in both a high-McTN cell line (MDA-436) and one with fewer McTNs (MCF-7). PEMs formed from a combination of polymethacrylic acid (PMA) and polyacrylamide (PAAm) provided a weakly cytophillic surface that supported weak attachment of tumor cells (<5%) even after 4 hours of incubation (FIG. 19A). In comparison, in both cells line more than 80% of cells attached to an uncoated surface. Ellipsometry showed that the thickness of the PMA/PAAm layer was proportional to the number of layers deposited, ranging from 10 nm (1 bilayer) to 90 nm (8 bilayers). The optical clarity of the coatings remained close to 100%, irrespective of the number of layers. Simple application of the PMA/PAAm film to commercially-available microfluidic chips (FIG. 19B, Ibidi, u-slideVI0.4) prevented adhesion of MDA-436 and MCF-7 cells. The coatings also provided outstanding optical clarity for confocal microscopy imaging of McTNs, even allowing detailed observation of live cell-cell attachment with McTNs (FIG. 19C). Moreover, this was achievable with a very small sample volume (30 uL). In this aim, we will combine PMA/PAAm PEMs with DNA-based tethering technology to develop a coating that can be applied to microfluidic channels to tether cells while maintaining free-floating cell behavior.

a) Test PEM Film Composition to Inhibit Attachment in a Wide Variety of Breast Tumor Cell Lines.

Strategy and Analysis: We have characterized 15 different breast cancer cell lines for McTNs (Balzer E M, Whipple R A, Thompson K, Boggs A E, Slovic J, Cho E H et al (2010). c-Src differentially regulates the functions of microtentacles and invadopodia. Oncogene 29: 6402-6408; Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. Oncogene 29: 3217-3227; Whipple R A, Balzer E M, Cho E H, Matrone M A, Yoon J R, Martin S S (2008). Vimentin filaments support extension of tubulin-based microtentacles in detached breast tumor cells. Cancer Research 68: 5678-5688; Whipple R A, Matrone M A, Cho E H, Balzer E M, Vitolo M I, Yoon J R et al (2010). Epithelial-to-mesenchymal transition promotes tubulin detyrosination and microtentacles that enhance endothelial engagement. Cancer Res 70: 8127-8137; Charpentier M S, Whipple R A, Vitolo M I, Boggs A E, Slovic J, Thompson K N et al (2013). Curcumin targets breast cancer stem-like cells with microtentacles that persist in mammospheres and promote attachment. Cancer Res) and we will test the efficiency of a PMA/PAAm film to reduce cell attachment across this panel. Sequential exposure and washing will be used to apply 1, 4 or 8 bilayers PMA/PAAm film to the Ibidi slides, and suspensions of breast tumor cell lines (1000 cells in 30 uL complete growth media) will then be applied to the channels. Cell attachment will be gauged by microscopy at 30 minute intervals from 0-240 minutes. We will also investigate the material properties (e.g., stability, surface roughness) of the PEMs before and after cell incubation using atomic force microscopy and ellipsometry as we have published previously (Yang S Y, Mendelsohn J D, Rubner M F (2003). New class of ultrathin, highly cell-adhesion-resistant polyelectrolyte multilayers with micropatterning capabilities. Biomacromolecules 4: 987-994; Kohli N, Vaidya S, Ofoli R Y, Worden R M, Lee I (2006). Arrays of lipid bilayers and liposomes on patterned polyelectrolyte templates. J Colloid Interface Sci 301: 461-469).

Figure 19:
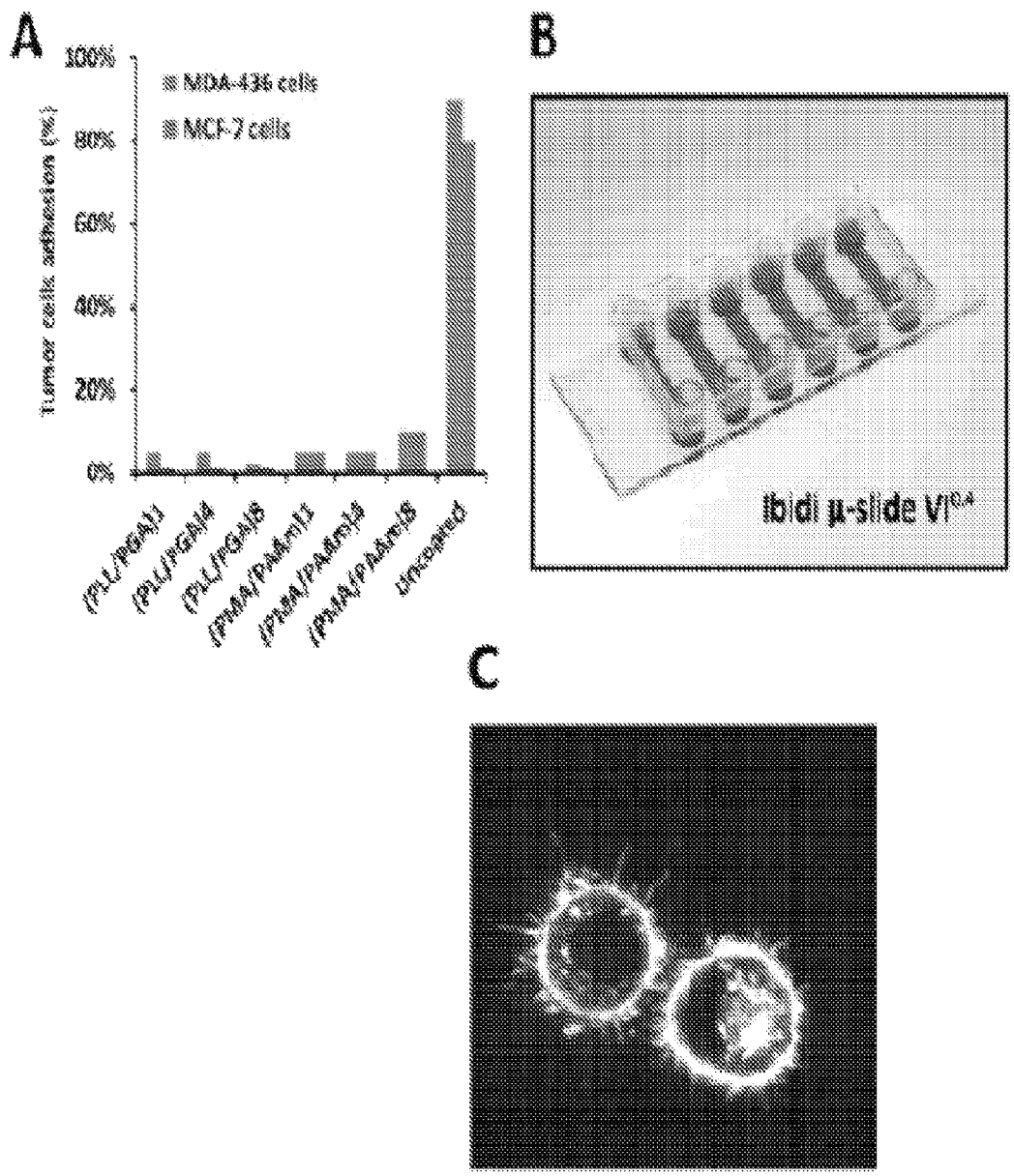
FIG. 19. PEM allows tuning of tumor cell adhesion and support maintenance of McTNs. A) Breast tumor cell lines incubated on PEM-coated surface adhere at differential levels depending on film composition and the number of bilayers deposited (i.e., film thickness). B) Films can be readily deposited on a commercially available microfluidic chamber used for direct visualization of (C) McTNs in live tumor cells.

PAAm is well-studied in terms of its ability to reduce cell attachment without causing cell toxicity and PMA is a key component of polyhydroxyethylmethacrylate (polyHEMA) that has been used widely to prevent cell attachment (Brouquet A, Taleb P, Lot A S, Beauchet A, Julie C, Prevost G et al (2011). A model of primary culture of colorectal cancer and liver metastasis to predict chemosensitivity. The Journal of surgical research 166: 247-254). For these reasons, we expect that this coating will be effective and non-toxic. To control for cytotoxicity, we will culture the 15 cell lines within the microfluidic slides for 3 days and gauge cell death by trypan blue exclusion. If the planned PMA/PAAm films allow attachment of more than 3 out of the 15 breast tumor cell lines within 240 minutes, or causes toxicity in more than 3 out of 15 cell lines over 3 days, we will test alternative surface compositions or increased numbers of layers. As shown in FIG. 19, we have already identified that PEMs composed of Poly-L-lysine (PLL) and Poly-L-Glutamic acid (PGA) have a very similar ability to prevent MDA-436 and MCF-7 attachment. We prioritized PMA/PAAm because PAAm has an amide side group that has many options for surface modification and cross-linking applications (Lakins J N, Chin A R, Weaver V M (2012). Exploring the link between human embryonic stem cell organization and fate using tension-calibrated extracellular matrix functionalized polyacrylamide gels. Methods in molecular biology 916: 317-350). However, if we encounter difficulties with PMA/PAAm, the PLL/PGA film can serve as an immediate alternative.

b) Validate PEM-Mediated Attachment Inhibition with Patient-Derived Cells (Fresh Surgical and Tumorgraft).

Figure 20:
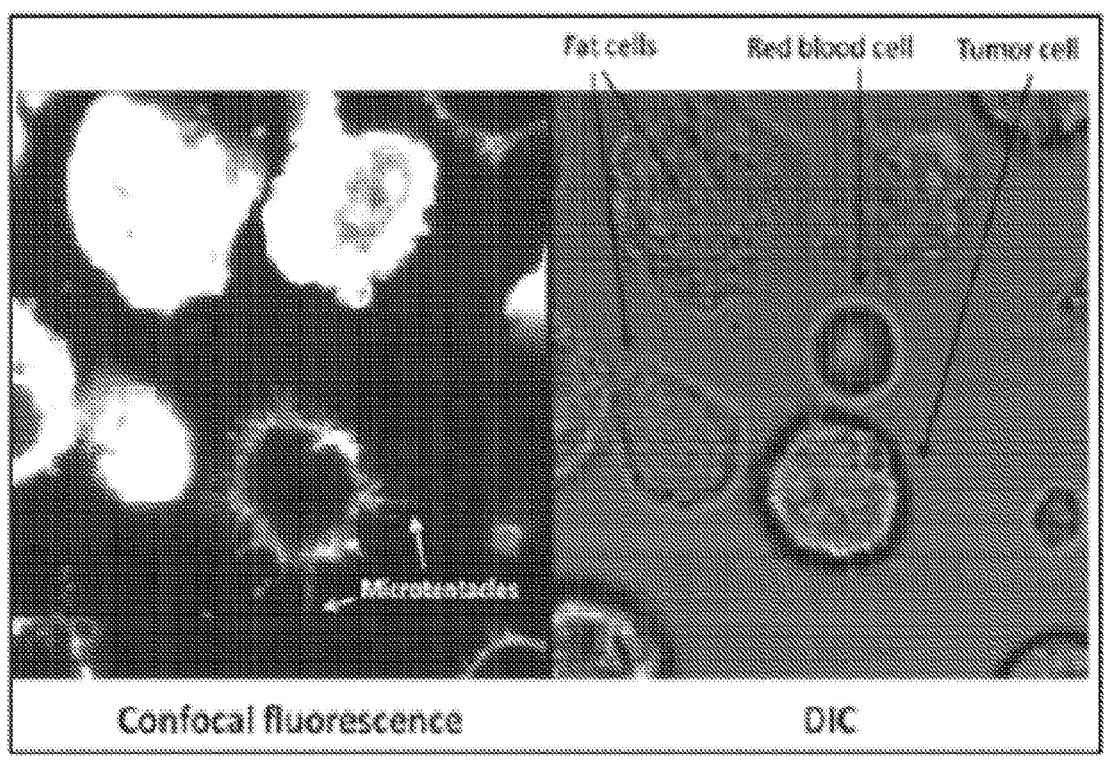
FIG. 20. Testing adhesion of patient-derived cell mixtures in microfluidic slides. Microtentacles are observable in patient tumor cells (arrows, left), but samples include non-tumor cell types (right).

Strategy and Analysis: Ibidi microfluidic slides coated with 2 PMA/PAAm films will be used to test the adhesion of more complex mixtures of patient-derived cells. Epithelial cell suspensions are purified by enzymatic digestion (collagenase/hyaluronidase) and differential centrifugation (DeRose Y S, Gligorich K M, Wang G, Georgelas A, Bowman P, Courdy S J et al (2013). Patient-derived models of human breast cancer: protocols for in vitro and in vivo applications in tumor biology and translational medicine. Current protocols in pharmacology/editorial board, S J Enna Chapter 14: Unit14 23) from either fresh patient tumor fragments or tumorgrafts that have been expanded through orthotopic transplant into the mammary glands of NOD/SCID mice (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. Nat Med 17: 1514-1520). It is possible to generate 105-106 epithelial cells from these preparations (DeRose Y S, Gligorich K M, Wang G, Georgelas A, Bowman P, Courdy S J et al (2013). Patient-derived models of human breast cancer: protocols for in vitro and in vivo applications in tumor biology and translational medicine. Current protocols in pharmacology/editorial board, S J Enna Chapter 14: Unit14 23), but there is inevitably some contamination with other cell types, primarily fat cells and red blood cells (FIG. 20). To advance the PEM microfluidic approach to clinical application, we will need to ensure that these additional cell types do not obscure the observation of tumor cells by adhering to the surface. Independent preparations from 5 patients and the resulting tumorgrafts will therefore be tested for adhesion to PEM-coated channels over four hours.

Expected Outcomes, Potential Problems and Alternative Strategies: While the differential centrifugation strategy has been established to enrich for epithelial tumor cells (DeRose Y S, Gligorich K M, Wang G, Georgelas A, Bowman P, Courdy S J et al (2013). Patient-derived models of human breast cancer: protocols for in vitro and in vivo applications in tumor biology and translational medicine. Current protocols in pharmacology/editorial board, S J Enna Chapter 14: Unit14 23), it remains possible that some of the observed cells in the clinical samples could be lymphocytes. To rigorously identify tumor cells, we will use a standard identification for circulating breast tumor cells to distinguish epithelial tumor cells (EpCAM+/CD45−) and lymphocytes (EpCAM−/CD45+) (Takao M, Takeda K (2011). Enumeration, characterization, and collection of intact circulating tumor cells by cross contamination-free flow cytometry. Cytometry Part A: the journal of the International Society for Analytical Cytology 79: 107-117). An independent double-positive stain for cytokeratins (CK8/CK18) (Stoler D L, Stewart C C, Stomper P C (2002). Breast epithelium procurement from stereotactic core biopsy washings: flow cytometry-sorted cell count analysis. Clin Cancer Res 8: 428-432) can also be used to identify breast tumor cells. Red blood cells are easily identifiable by their small size and concave morphology and fat cells stain very brightly with the lipophilic compound (CellMask) used to visualize microtentacles (FIG. 20, left panel), making it relatively simple to exclude these cell types during imaging. c) Integrate a DNA oligo for membrane tethering into the upper PEM surface. Strategy and Analysis: Using published methods (Saurer E M, Jewell C M, Roenneburg D A, Bechler S L, Torrealba J R, Hacker T A et al (2013). Polyelectrolyte multilayers promote stent-mediated delivery of DNA to vascular tissue. Biomacromolecules 14: 1696-1704; Jewell C M, Zhang J, Fredin N J, Lynn D M (2005). Multilayered polyelectrolyte films promote the direct and localized delivery of DNA to cells. Journal of controlled release: official journal of the Controlled Release Society 106: 214-223; Flessner R M, Jewell C M, Anderson D G, Lynn D M (2011). Degradable polyelectrolyte multilayers that promote the release of siRNA. Langmuir: the ACS journal of surfaces and colloids 27: 7868-7876), a short DNA oligo (20 nts) will be electrostatically adsorbed to PEMs by incubation (304, 0.2 mg/mL) over a PMA/PAAm film with a cationic capping layer of PAAm or the strong polycation, PLL. A lipid-coupled complementary DNA strand will be added to suspended MDA-436 and MCF-7 cells34 (Adheren, Inc.). Suspensions of 5,000 cells in 30 μL of PBS will then be applied to the channels and hybridized for 30 minutes with the complementary DNA displayed on the PEM-coated channel. The ability of cells to remain on the PEM-DNA surface will be tested by repeatedly washing the channel with 50 uL of media. The number of cells released will be measured by a Countess automated hemocytometer after each wash.

Expected Outcomes, Potential Problems and Alternative Strategies: We have already established the DNA-tethering method (FIG. 18), so we do not anticipate difficulty with that part of the approach. There may be potential complications if the electrostatic interaction of the charged DNA with the PEM layer is not sufficient to secure cells during the media exchanges. In this case, we will incorporate a strong polyelectrolyte (e.g., PDAC) as the "capping" layer or explore covalent linkage for the DNA to the PAAm, as published by others (Chippada U, Yurke B, Georges P C, Langrana N A (2009). A nonintrusive method of measuring the local mechanical properties of soft hydrogels using magnetic microneedles. Journal of biomechanical engineering 131: 021014).

Specific Aim 2: Engineer a direct lipid anchor as an alternative label-free approach to tether tumor cells.

Rationale: DNA-based cell tethering is certainly effective for McTN imaging in cultured cell lines. However, since this strategy requires very high concentrations of cells ($10^7$ cells/ml) for the initial DNA membrane labeling procedure (Selden N S, Todhunter M E, Jee N Y, Liu J S, Broaders K E, Gartner Z J (2012). Chemically programmed cell adhesion with membrane-anchored oligonucleotides. Journal of the American Chemical Society 134: 765-768), it would be advantageous to develop a more direct strategy for the analysis of clinical samples, where limited numbers of cells are available. In this aim, we will develop methods for the direct conjugation of membrane-tethering lipid to the top layer of the PEM film within the microfluidic channel slide. This also avoids the difficulties that arise during the DNA-tethering method when the DNA-lipid label is rapidly internalized into the target cells by membrane recycling, effectively reducing the tethering capability. Moreover, this lipid conjugation approach will remove any need to pre-label the cells applied to the attachment surface, since the interaction between the lipid-coated surface and the cell membrane will be direct.

a) Design Lipid Tethers to Support McTNs on Cells without Use of DNA Oligos or Other Additives (Label-Free).

Figure 21:
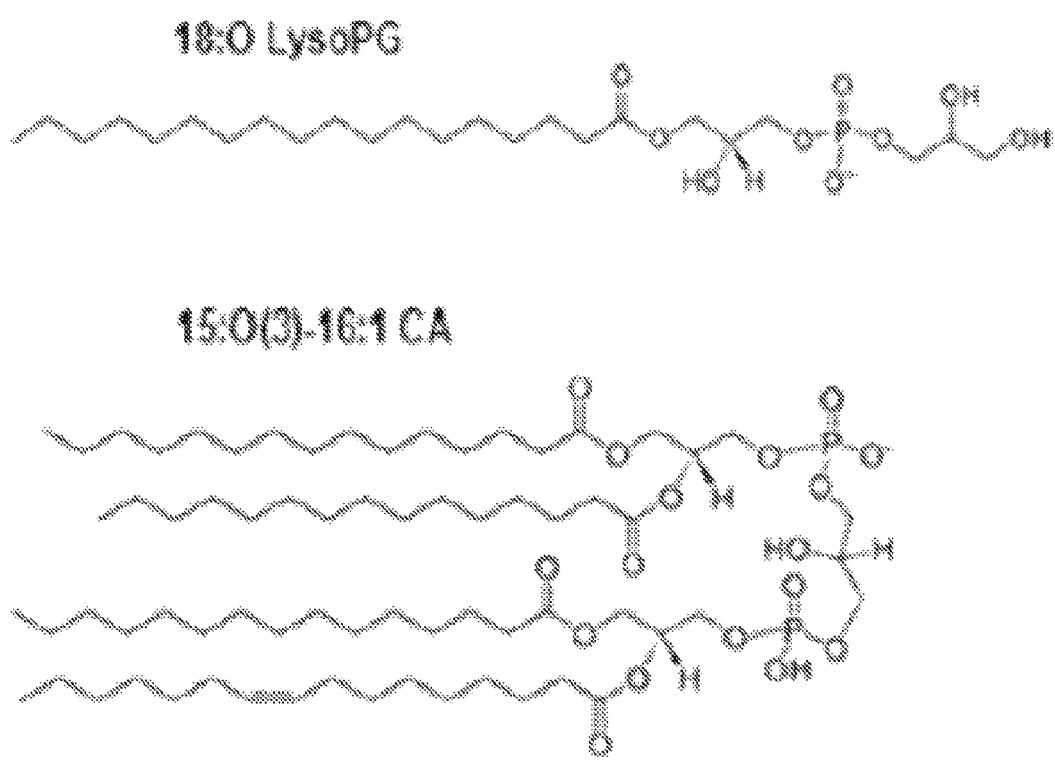
FIG. 21. Commercially-available glycerophospholipids (Avanti Polar Lipids, Inc.) for integration into a polyelectrolyte layer.

Strategy and Analysis: For efficient cell tethering, a lipid with long, hydrophobic fatty acids is required to associate with the membrane. The ideal molecule would also have a charged headgroup to support PEM adsorption. Using these constraints, we have prioritized the following two commercially-available glycerophospholipids (Avanti Polar Lipids, Inc.) for integration into our PMA/PAAm bilayer (FIG. 21). The negatively charged phosphate in each glycerophospholipid can be used to interact with the positively charged amide group in the terminal PAAm layer of the PEM film. To optimize the lipid surface density and tune tumor cell adhesion, lipids will be prepared for adsorption using the lipid film rehydration technique. Briefly, different lipid ratios (1:10-10:1 LysoPG:CA) at total concentrations of 1-10 μmol of lipid will be dried under nitrogen, then sonicated (12 W, 30 sec) in 500 μL of HEPES. The PEM-coated surface or channel will then be exposed to the lipid solution for 5 minutes and washed twice.

Expected Outcomes, Potential Problems and Alternative Strategies: Since the tethering of the cells to the surface will be direct, it will be important to control the seeding cell density to avoid overcrowding the imaging area. Our initial tests show that the dimensions of our microfluidic channel (14 mm×3.8 mm×0.2 mm height) allows for an even distribution of approximately 5,000 to 20,000 cells. Higher densities lead to rapid cell-cell clustering without a tethering method to keep cells from drifting into each other. The major potential complication we foresee with the lipid method is that our primary fluorescent labeling method is based on a lipophilic cell membrane dye, which may also bind to lipids conjugated to the channel surface and generate high fluorescence background. There are several strategies that we can use to overcome this challenge. First, confocal microscopy excludes the out-of-focus light, so increased labeling at the attachment surface will not prevent us from imaging the center plane of the cells with low background. We currently use this strategy, since a low concentration of the membrane dye (CellMaskOrange, 1:20,000) is left on the cells during imaging, and confocal imaging allows exclusion of background and high-resolution imaging of the membrane. If the background signal remains too high, there are several other membrane dyes that could be used (DiI, DiO), but might present similar difficulties. In the case that all lipophilic dyes are ineffective for this reason, we can also stain live cells with a fluorescent wheat-germ agglutinin (Alexa594-WGA) which binds glycosylated residues on the cell membrane rather than through lipid affinity and labels McTNs efficiently (FIG. 1B, arrow).

b) Use μCP to Generate Lipid Islands of 5-10 μm in Diameter for Single-Cell Tethering.

Figure 22:
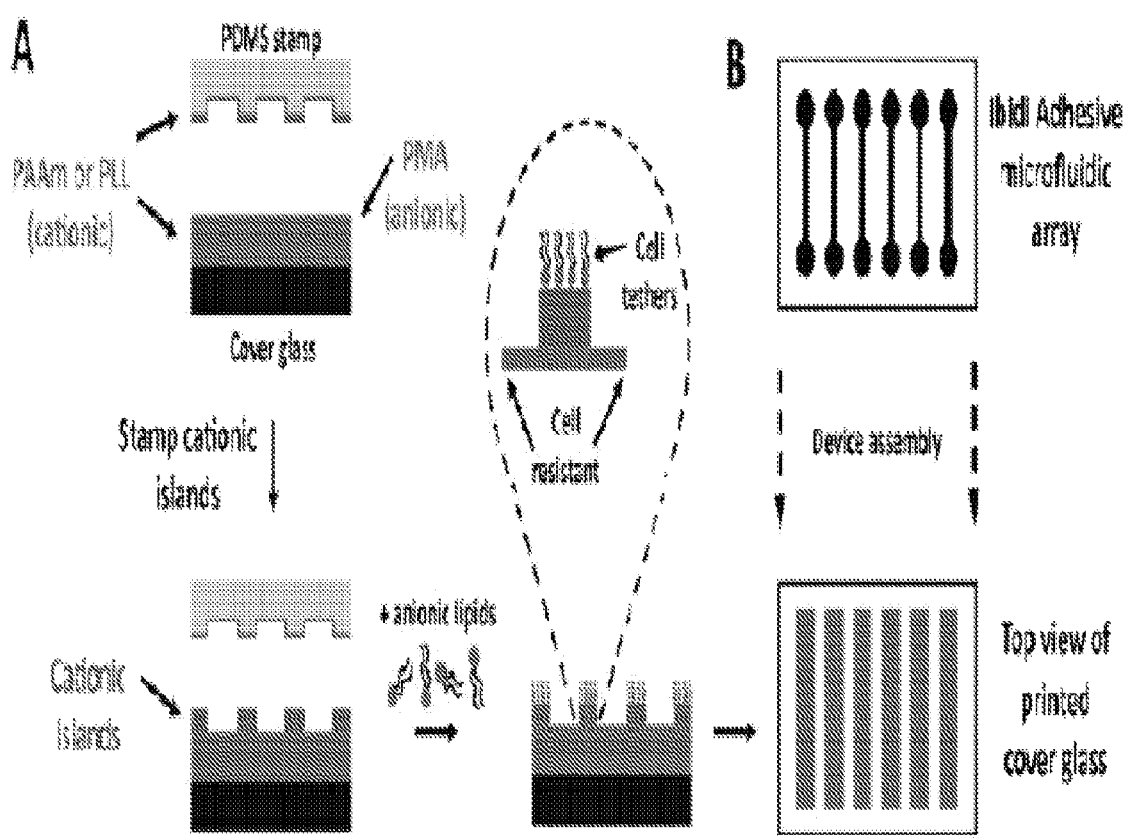
FIG. 22. μCP allows patterning of single-cell lipid tethers on a cytophobic PEM background. A) μCP of a cationic layer produces cationic islands for integration of lipid tethers on a background of a CTC resistant PEM. B) The patterned cover glass is then aligned and assembled with an adhesive microfluidic array.

To generate an array of single-cell lipid attachment points, we will use a PDMS microcontact printing (μCP) procedure that patterns lipid on the upper PEM layer (PAAm or PLL) in small 5-10 μm spots (Kohli N, Vaidya S, Ofoli R Y, Worden R M, Lee I (2006). Arrays of lipid bilayers and liposomes on patterned polyelectrolyte templates. J Colloid Interface Sci 301: 461-469). The geometry that we used for FIG. 18 (7 μm spots with 40 μm spacing between centers) is a good starting point, since it works well for the DNA tethering approach. Since the μCP method will require a flat surface, we will first deposit PAAm/PAM PEMs on ultra-clean glass coverslips (Nexterion—Applied Microarrays, Inc.) along the Ibidi slide channel geometry in the UMCP nanofabrication facility (Fablab). A PDMS master containing the stamping geometry will be "inked" with a cationic layer (i.e., PAAm or PLL) and brought in contact with the PEM using a robotic deposition system or EVG aligners (FIG. 22A). Surfaces will then be exposed to the lipid compositions and densities described in Aim 2a, washed, followed by assembly of the final device by binding the coverslip to a matching adhesive array of six microfluidic channels (FIG. 22B), which is available from Ibidi (sticky-Slide VI0.4, FIG. 19B).

Expected Outcomes, Potential Problems and Alternative Strategies: The μCP technique is more complicated than simple solution based adsorption of DNA labels (Aim 1), but the technique is well-established and we do not anticipate significant challenges considering the outstanding instrumentation and expertise available. For Aim 2b, Suss and EVG proximity/contact aligners, Headway photoresist spinners (for preparation of masters), and SEMs will be the most useful resources. To simplify cell tethering in intact channels, we will design a photoactivatable lipid tether in Aim 2c.

c) Develop Photoactivatable Lipid Anchor for Lithography Directly in Microfluidic Channels.

Figure 23:
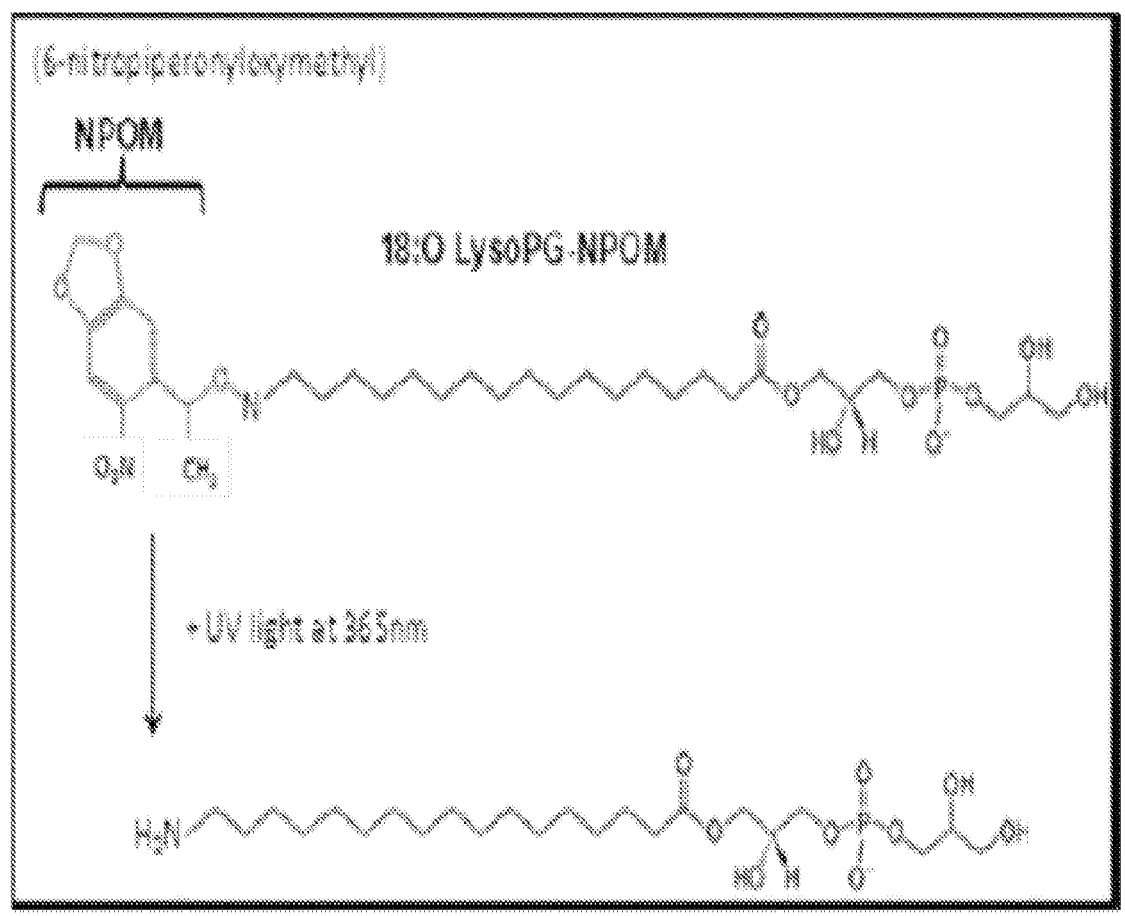
FIG. 23. Photoactivatable lipid anchor for lithography directly in microfluidic channels.
Figure 24:
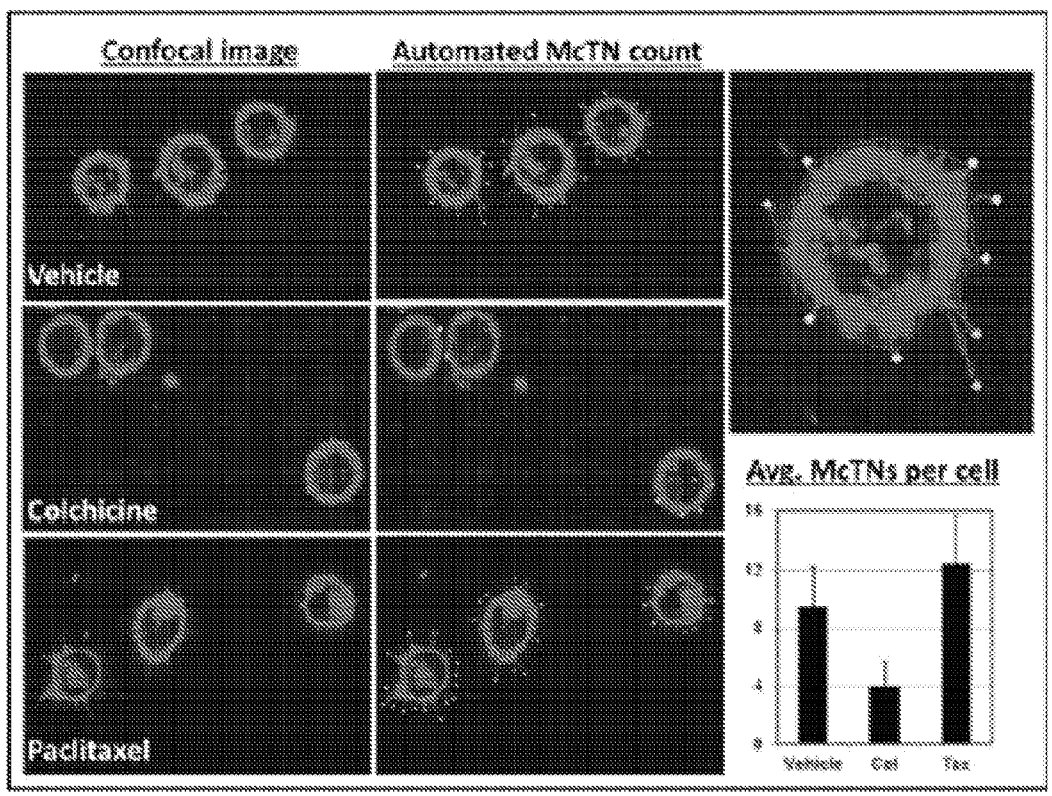
FIG. 24. Automated McTN analysis. MDA-436 cells were treated with vehicle (0.1% DMSO) or colchicine (50 μM) or paclitaxel (1 μM) and imaged for McTNs with confocal microscopy. A gradient vector flow snake algorithm was used to define the cell edges and a local curvature maxima effectively identified McTN ends (yellow diamonds). Quantitation of at least 10 random cells shows that Colchicine (Col) significantly reduces the average number of McTNs per cell, while paclitaxel (Tax) increases McTNs, but this does not reach significance in MDA-436 cells. This automated cell shape analysis will also enable calculations of average McTN length, curvature, etc. that will yield more multi-dimensional data for McTN studies.

Strategy and Analysis: Conjugation of a photo-cleavable charged group to the end of the lipid used for Aim 2a would generate a molecule that could be integrated in solution to the PEM layer in intact microfluidic channels. We will use a 6-nitropiperonyloxymethyl (NPOM) group, which can be coupled to lipid via an amine linker and then cleaved through illumination with UV light at 365 nm (FIG. 23). The charges present on the NPOM should reduce hydrophobic interactions with the cell membrane. We will prepare a photolithography mask in the Fablab and use the Suss mask aligner—able to pattern features>1 μm—to directly illuminate PEM coated Ibidi microchannels with 7 μm islands and 40 μm center spacing (as in the DNA tethering arrays, FIG. 18). Stocks of 18:OLysoPG-NPOM will be custom synthesized by Avanti Polar Lipids, Inc. If successful, this approach will eliminate the need for stamping.

Expected Outcomes, Potential Problems and Alternative Strategies: The precise lipid for NPOM conjugation will be guided by the studies in Aim 2a. However, it is possible that the single remaining amine will provide enough charge to significantly reduce the membrane tethering of 18:OLysoPG. In this case, we will have to identify another photoactive group with reduced residual charge upon cleavage and work with Fablab experts on a new lithography method.

Specific Aim 3: Analyze patient tumor cell microtentacles and drug responses and relate to tumorgraft outcome Rationale: McTNs on the surface of free-floating tumor cells serve as an indicator of their reattachment efficiency during experimental metastasis in vivo (Balzer E M, Whipple R A, Thompson K, Boggs A E, Slovic J, Cho E H et al (2010). c-Src differentially regulates the functions of microtentacles and invadopodia. Oncogene 29: 6402-6408; Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. Oncogene 29: 3217-3227). In addition, we have recently published an article in Cancer Research demonstrating that McTNs are a marker of increased tumor stem cell characteristics (Charpentier M S, Whipple R A, Vitolo M I, Boggs A E, Slovic J, Thompson K N et al (2013). Curcumin targets breast cancer stem-like cells with microtentacles that persist in mammospheres and promote attachment. Cancer Res). In this aim, we will use the prioritized PEM devices and live-cell confocal microscopy to examine McTN extension and dynamics in freshly-isolated tumor cells from breast cancer patients. These findings on McTN incidence and drug response will be related to the tumorigenic and metastatic properties of parallel patient-derived tumorgrafts. Tumor cells acquired from residual de-identified patient tissue by the Translational Core lab will be directly transplanted into the cleared mammary fat pad of immunodeficient NOD/SCID mice. This system was developed by Dr. Alana Welm at the University of Utah Huntsman Cancer Institute and avoids altering the properties of patient-derived tumor cells through selection with in vitro culture conditions. In a recent Nature Medicine article (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. Nat Med 17: 1514-1520), Dr. Welm's group showed that the direct transplantation method allows tumorgrafts to retain the ER/PR/HER2 status and emulate the metastatic dissemination pattern of the original patient's tumor. It was particularly notable that when the patients' tumors successfully grew in mice, those patients were at a much higher risk of early recurrence and shortened survival (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. Nat Med 17: 1514-1520). We already have a number of tumorgraft lines in-hand (Table 3), that were generated from residual de-identified tissue from breast cancer patients at the UMGCC by the Translational Core lab, or provided by the Huntsman Cancer Institute. However, while tumorgrafts faithfully retain the clinical characteristics of the original patient, tumorgraft results often require many months to develop (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. Nat Med 17: 1514-1520; DeRose Y S, Gligorich K M, Wang G, Georgelas A, Bowman P, Courdy S J et al (2013). Patient-derived models of human breast cancer: protocols for in vitro and in vivo applications in tumor biology and translational medicine. Current protocols in pharmacology/editorial board, S J Enna Chapter 14: Unit14 23). The device we will develop through this project will allow rapid analysis of patient tumor cell cytoskeletal dynamics and drug response in the first 24 hours that can be compared to tumorgraft outcome and patient outcome. Since this approach avoids any expansion of patient cells in culture, selective pressures imposed by long-term in vitro growth are reduced.

TABLE 3

Initial Tumorgraft cell lines

| ID# | ER | PR | HER2 | Metastasis Sites | Dormancy (time to 0.1 cm$^3$) | Race |
|---|---|---|---|---|---|---|
| HCI-001 | − | − | − | Lung, LN | 4 weeks | Caucasian |
| HCI-002 | − | − | − | LN | 5 weeks | Caucasian |
| HCI-003 | + | + | − | Lung, LN | 11 weeks | Caucasian |
| HCI-004 | − | − | − | None detected | 21 weeks | Caucasian |
| HCI-005 | + | + | + | Lung, bone | 13 weeks | Caucasian |
| HCI-008 | − | − | + | Lung, bone | 20 weeks | Caucasian |
| HCI-010 | − | − | − | Lung, LN | 25 weeks | Caucasian |
| HCI-011 | + | + | − | LN, pleura | 27 weeks | African-American |
| UMB-BR-001 | − | − | − | Pending | 3 weeks | African-American |
| UMB-BR-002 | − | − | − | Pending | 5 weeks | African-American | a) Compare Efficiency of 2 PEM Devices for Tethering Patient-Derived Tumorgraft Cells.

Strategy and Analysis: The efficiency of DNA-mediated (Aim 1) and lipid-mediated (Aim 2) tumor cell tethering will be compared to determine which device will be advanced to a larger clinical study. We will use these existing tumorgrafts (Table 1) to recover breast tumor cells from tissue and determine which approach yields the most efficient retention of 5,000 purified epithelial cells with the least residual contamination with fat cells, lymphocytes and red blood cells. Cell retention will be followed by automated hemocytometer (Countess), as in Aim 1. Following the outcome of this analysis, we will select either the DNA or lipid-based tethering approach for subaims 3b and 3c.

Expected Outcomes, Potential Problems and Alternative Strategies: Since only about 40% of human breast cancer tumorgrafts grow after orthotopic transplantation (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. Nat Med 17: 1514-1520), we will start our analysis with existing tumorgrafts obtained from our Translational Core lab and the Huntsman Cancer Institute (Table 1). While we are confident that one or both of the tethering strategies will work for tumorgraft and fresh patient samples, it remains possible that neither tether will be effective. In this case, we will still be able to analyze the McTN incidence and drug response of the samples (as we did in FIGS. 1, 6, 7 and 11), the cells will just be more randomly distributed and we will have to use fewer cells per channel to prevent cell-cell clustering during random cell drifting.

b) Expand Analysis with Prioritized Device to 40 Patients for McTN Analysis and Drug Response Studies.

Figure 12:
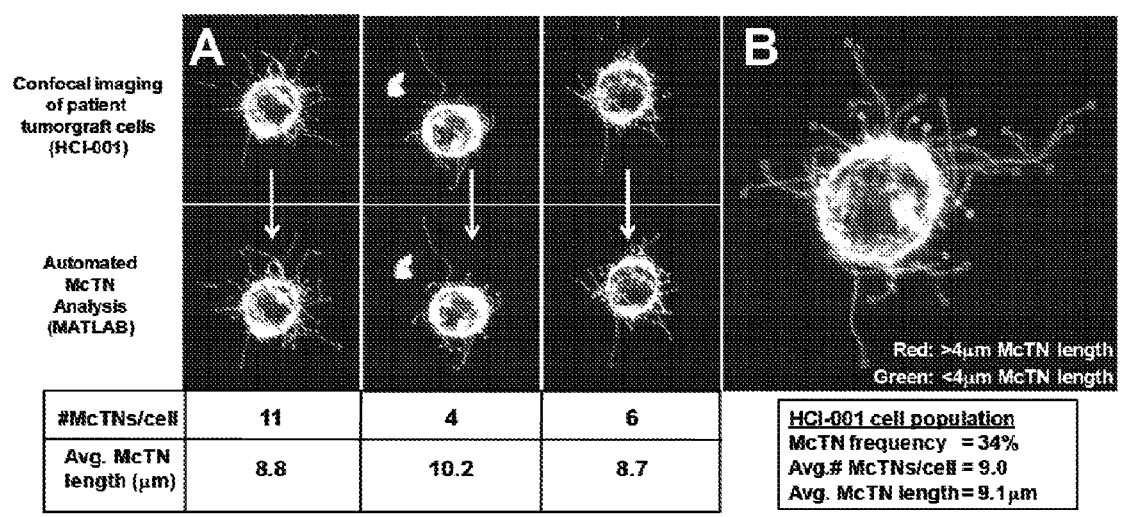
FIG. 12. Automated Measurements of Microtubule (McTN) Characteristics.
Figure 14:
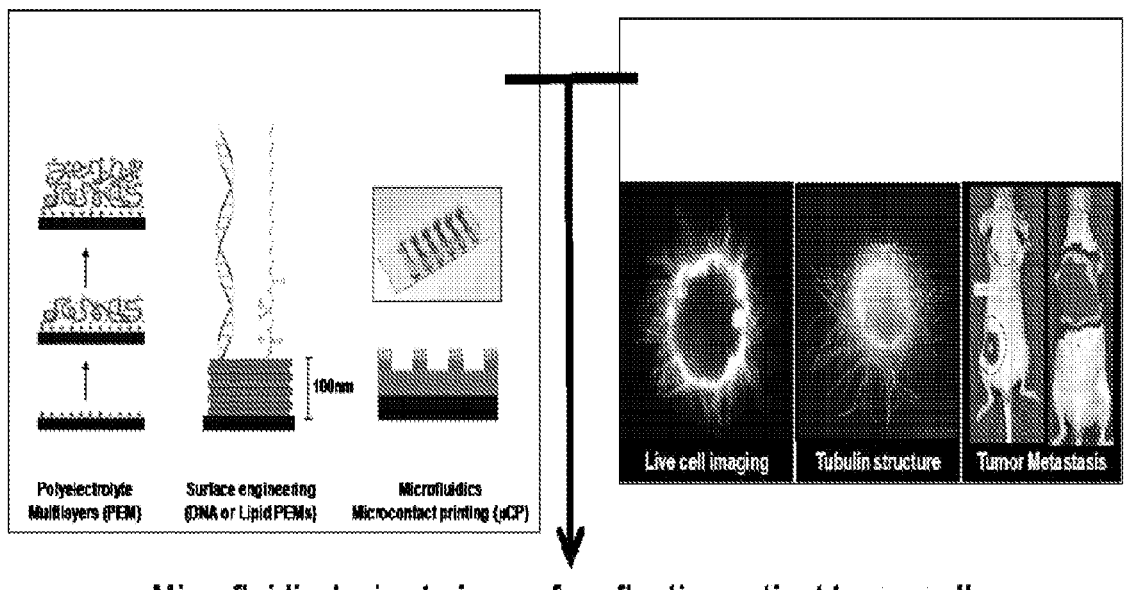
FIG. 14. Schematic showing tethering of cells to a microfluidic slide to image free floating patient cancer cells. The tether can hold the cell in place for confocal imaging and efficient capture of images.
Figure 14:
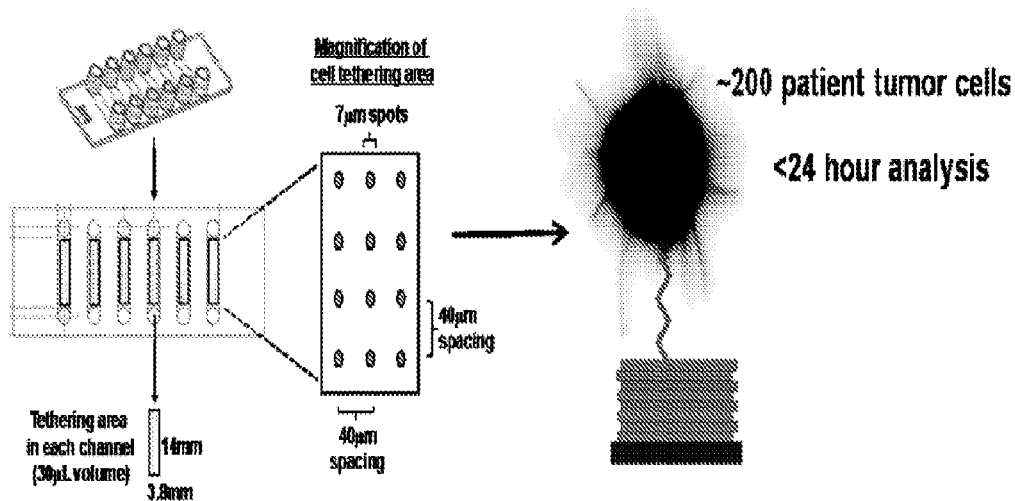
Figure 15:
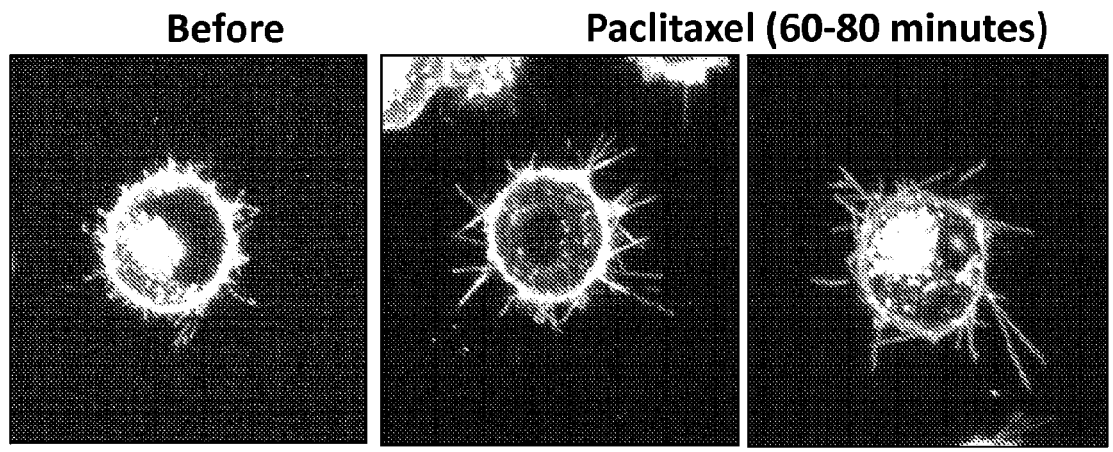
FIG. 15. Confocal images of tethered cells treated with paclitaxel and cholchicine.
Figure 15:
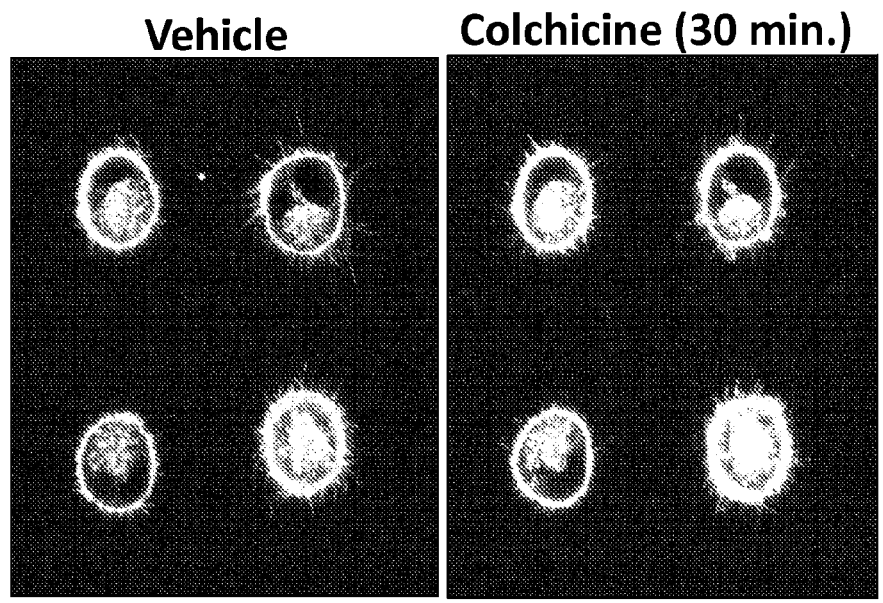
Figure 16:
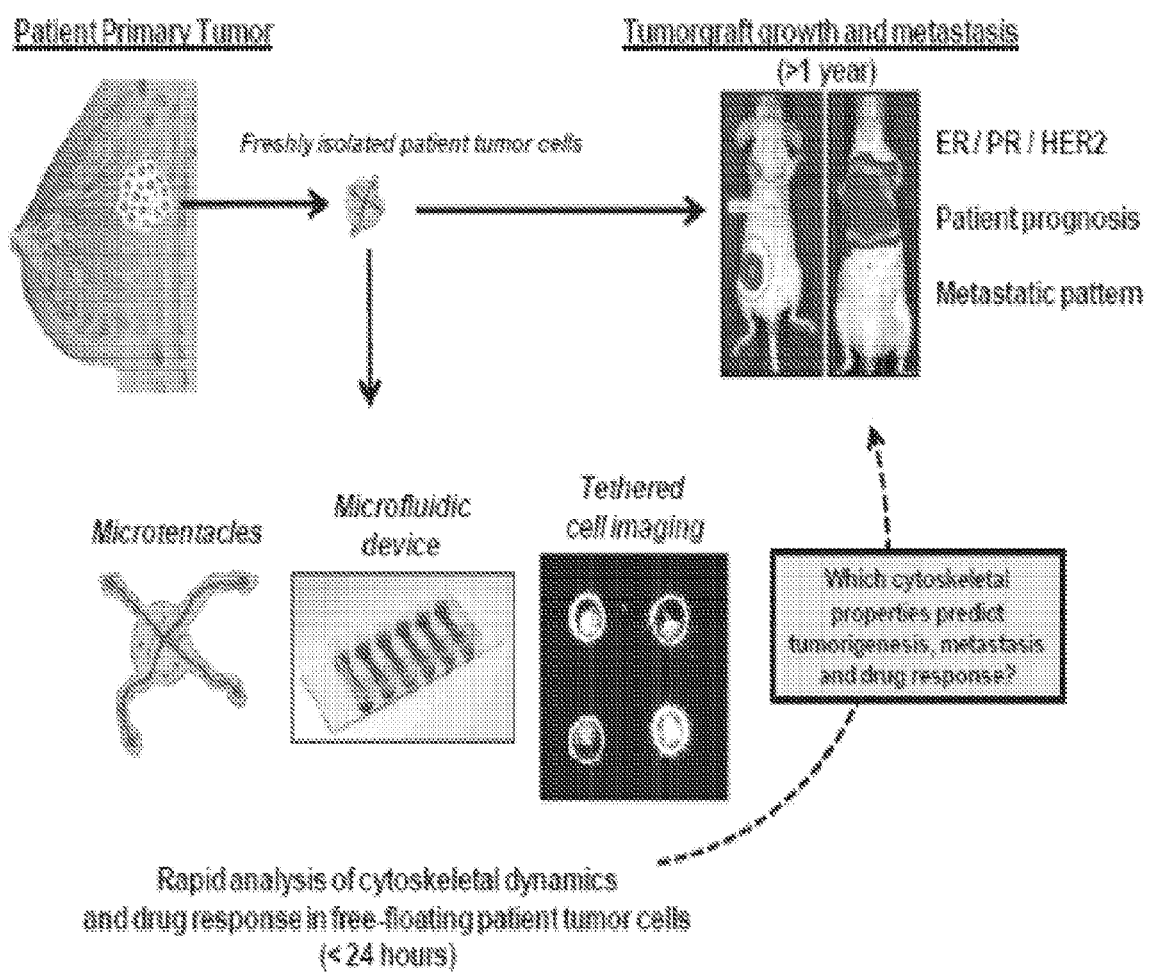
FIG. 16. Schematic showing isolation of cancer cells and subsequent analysis of microtentacles using a microfluidic device and tumor graft growth and metastasis.

Strategy and Analysis: The device prioritized from subaim 2a will be used to analyze fresh patient samples as well as the resulting tumorgrafts from 40 patients during the three years of the project. McTN images collected from each cell sample will be analyzed with a custom MatLab algorithm developed for this assay that can automatically identify McTNs but also score metrics that were previously not possible to measure, such as the average number of McTNs per cell (FIG. 12). We are currently incorporating the ability to measure average McTN length and curvature. Once we have established the baseline levels of McTNs for each cell sample, we will test the responses to 6 different microtubule-directed drug compounds that are either already FDA-approved or in trials (Table 2). Drugs will be added by media exchange across the six microfluidic channels at the concentrations listed in Table 4 for 60 minutes, which each affect McTNs in 1 hr. (Whipple R A, Balzer E M, Cho E H, Matrone M A, Yoon J R, Martin S S (2008). Vimentin filaments support extension of tubulin-based microtentacles in detached breast tumor cells. Cancer Research 68: 5678-5688; Whipple R A, Matrone M A, Cho E H, Balzer E M, Vitolo M I, Yoon J R et al (2010). Epithelial-to-mesenchymal transition promotes tubulin detyrosination and microtentacles that enhance endothelial engagement. Cancer Res 70: 8127-8137; Charpentier M S, Whipple R A, Vitolo M I, Boggs A E, Slovic J, Thompson K N et al (2013). Curcumin targets breast cancer stem-like cells with microtentacles that persist in mammospheres and promote attachment. Cancer Res.; Whipple R A, Vitolo M I, Boggs A E, Charpentier M S, Thompson K, Martin S S (2013). Parthenolide and costunolide reduce microtentacles and tumor cell attachment by selectively targeting detyrosinated tubulin independent from NF-kappaB inhibition. Breast Cancer Res 15: R83), except Ixabepilone, which has not been tested yet on McTNs.

TABLE 4

List of cytoskeletal modulators. (FDA-approved*)

| Drugs | Conc. | Target | Effect | Predicted stemness & McTN effect |
|---|---|---|---|---|
| Paclitaxel* | 1 μM | Micro-tubules | Stabilize | Increase |
| Ixabepilone* | 0.2 μM | | | |
| Vinblastine* | 0.1 μM | Micro-tubules | Depolymerize | Decrease |
| Colchicine* | 50 μM | | | |

TABLE 4-continued

List of cytoskeletal modulators. (FDA-approved*)

| Drugs | Conc. | Target | Effect | Predicted stemness & McTN effect |
|---|---|---|---|---|
| Parthenolide | 10 µM | | | |
| Curcumin | 50 µM | | | |

Expected Outcomes, Potential Problems and Alternative Strategies: As noted in subaim 3a, it remains possible that the tethering strategies will not be effective for clinical samples. In this case, we can use untethered cells on tuned PEM surfaces, (FIG. 11 and FIG. 19). The cells will be arranged randomly and are more apt to cluster, but our analysis method can score randomly-spaced cells. However, time-dependent drug responses would not work in untethered cells (as in FIG. 18) because drug addition will cause cell displacement.

c) Analyze Patient Tumor Cell Microtentacles and Drug Responses and Relate to Tumorgraft Outcome.

Strategy and Analysis: The McTN metrics measured for the fresh cells and tumorgrafts in Aim 3b (McTN frequency, Avg. McTNs per cell, Avg. McTN length) will be compared to the eventual outcome of the tumorgrafts (growth rate, metastatic efficiency, metastatic site), through a generalized McNemar's test of matrix results, as we have published previously (Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. Oncogene 29: 3217-3227). McTN metrics will also be compared to patient outcome and survival data, but the timeframe of this comparison will exceed the project period and likely take >10 years.

Expected Outcomes, Potential Problems and Alternative Strategies: This aim is simply a comparison of tumorgraft and clinical outcome data to McTN and drug response metrics, so we do not anticipate challenges with that comparison. However, an adequate group size for patients with different clinical characteristics will be important to allow cytoskeletal predictors of tumorgraft outcome to be determined, which will be as follows: Biostatistical Analysis and Group Size Calculations: We have published a comparison of McTN incidences in 8 breast tumor cell lines (Whipple R A, Balzer E M, Cho E H, Matrone M A, Yoon J R, Martin S S (2008). Vimentin filaments support extension of tubulin-based microtentacles in detached breast tumor cells. Cancer Research 68: 5678-5688), and a comparison of 5 breast tumor cell lines with McTNs on the optical cell stretcher (Kiessling T R, Herrera M, Nnetu K D, Balzer E M, Girvan M, Fritsch A W et al (2013). Analysis of multiple physical parameters for mechanical phenotyping of living cells. European biophysics journal: EBJ 42: 383-394) as well as a recent comparison of tumor stem cell markers and McTNs in 6 breast tumor cell lines44. Based on our preliminary data and published results (Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. Oncogene 29: 3217-3227; Whipple R A, Balzer E M, Cho E H, Matrone M A, Yoon J R, Martin S S (2008). Vimentin filaments support extension of tubulin-based microtentacles in detached breast tumor cells. Cancer Research 68: 5678-5688; Charpentier M S, Whipple R A, Vitolo M I, Boggs A E, Slovic J, Thompson K N et al (2013). Curcumin targets breast cancer stem-like cells with microtentacles that persist in mammospheres and promote attachment. Cancer Res), a sample size of at least 5 patients in each group will have an adequate power (~80%) to detect a probability of 0.08 that an observation in Group 1 is less than an observation in Group 2 using a Wilcoxon (Mann-Whitney) rank-sum test with a 0.05 two-sided significance level. We will aim to compare 4 groups as follows: 1) ER+/PR+/HER2-2) ER+/PR+/HER2+3) ER-/PR-/HER2+4) ER-/PR-/HER2-. The banking goal from residual de-identified tissue in the Translational Core tumorgraft bank will be 20 patients per year of the study, which is realistic since our hospital treats ~280 new breast cancer patients each year. Only about 40% of these samples can be expected to grow in mice (Welm), yielding approximately 24 new viable tumorgraft samples by the end of the grant period. The University of Maryland also has an exceptional level of recruitment of African-American patients to clinical studies (36%) compared to an average of ~5% among other Cancer Centers nationwide. It will be our goal to include de-identified samples from at least 13 African-American patients during the 3 year study so that free-floating tumor cell dynamics in this group can be analyzed independently with respect to metastasis (~5 will form successful tumorgrafts). If necessary, there are also alternative sources of patient-derived tumor cells from commercial (Champions Oncology—Baltimore, MD) and academic (Georgetown, Center for Cellular Reprogramming) sources.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A method for imaging microtentacles on cells taken directly from a primary solid tumor in a cancer patient to provide prognostic information and guide the patient's treatment comprising:
   i) obtaining one or more live primary tumor cells that has been isolated by dissociation ex vivo from the primary solid tumor in the patient; and
   ii) imaging the one or more live primary tumor cells and detecting the microtentacles.

2. The method of claim 1, wherein the one or more tumor cells are isolated directly from a non-removed tumor, from a tumor cell biopsy or from a tumor that is surgically removed.

3. The method of claim 1, wherein the one or more tumor cells are imaged by confocal microscopy.

4. The method of claim 1, wherein the one or more tumor cells are from a cancer selected from the group consisting of breast cancer, prostate cancer, lung cancer, bladder cancer, pancreatic cancer, brain cancer, liver cancer, testicular cancer, thyroid cancer, skin cancer, colon cancer, ovarian cancer, cervical cancer, and uterine cancer.

5. The method of claim 1, wherein the cells are isolated from the tumor within 48 hours of imaging.

6. The method of claim 1, wherein the cells have not undergone more than three doublings since isolation up to the point of imaging the cells.

7. The method of claim 1, wherein the method comprises adding the one or more live primary tumor cells to a device comprising a substrate, wherein the substrate is coated with one or more layers of one or more materials that substantially inhibit the cells from adhering to the substrate, wherein the substrate is coated with a tethering substance that adheres to the substrate and is capable of tethering the cell to the substrate and holding the cell in a substantially fixed position for imaging the cell.

8. The method of claim 7, wherein the substrate is coated with polyelectrolyte multilayer films and wherein the tethering substance is a charged lipid.

9. A method of identifying a subject with an increased likelihood of having or developing metastatic cancer comprising:
i) obtaining one or more live primary tumor cells that has been isolated by dissociation ex vivo from a primary solid tumor from the subject;
ii) imaging the one or more live primary tumor cells; and
iii) scoring the one or more imaged cells for microtentacles to determine whether the subject has an increased likelihood of having or developing metastatic cancer.

10. The method of claim 9, wherein the scoring comprises determining whether the one or more cells comprise two or more protrusions longer than the cell radius, wherein the one or more cells comprising two or more protrusions longer than the cell radius indicates an increased likelihood of having or developing metastatic cancer.

11. The method of claim 9, wherein the one or more tumor cells are isolated directly from a non-removed tumor, from a tumor cell biopsy or from a tumor that is surgically removed.

12. The method of claim 9, wherein the one or more tumor cells are imaged by confocal microscopy.

13. The method of claim 9, wherein the one or more tumor cells are from a cancer selected from the group consisting of breast cancer, prostate cancer, lung cancer, bladder cancer, pancreatic cancer, brain cancer, liver cancer, testicular cancer, skin cancer, colon cancer, ovarian cancer, cervical cancer, and uterine cancer.

14. The method of claim 9, wherein the cells are isolated from the tumor within 48 hours of imaging.

15. The method of claim 9, wherein the cells have not undergone more than three doublings since isolation up to the point of imaging the cells.

16. The method of claim 9, further comprising administering to the subject an effective amount of a drug to treat cancer.

17. A method for determining whether a candidate drug inhibits or promotes microtentacle formation and/or stability on isolated, live primary tumor cells from a cancer subject comprising:
i) obtaining one or more live primary tumor cells that has been isolated by dissociation ex vivo from a solid tumor from the subject;
ii) contacting the one or more live primary tumor cells with the candidate drug;
iii) imaging the one or more live primary tumor cells treated with the candidate drug; and
iv) scoring the one or more imaged cells for microtentacles to determine whether a candidate drug inhibits or promotes microtentacle formation and/or stability.

18. The method of claim 17, further comprising imaging one or more untreated, live primary tumor cells and scoring the untreated cells for microtentacles, and comparing the score for untreated cells with the score obtained from step iv) for treated cells.

19. The method of claim 18, wherein the treated and untreated cells are the same cells and the untreated cells are imaged and scored prior to step ii).

20. The method of claim 17, wherein the scoring comprises determining whether the one or more cells comprise two or more protrusions longer than the cell radius.

21. The method of claim 17, wherein the candidate drug promotes microtentacle formation and/or stability when the one or more cells exhibit a greater number of protrusions longer than the cell radius compared to untreated cells.

22. The method of claim 17, wherein the candidate drug inhibits microtentacle formation and/or stability when the one or more cells exhibit a reduced number of protrusions longer than the cell radius compared to untreated cells.

23. The method of claim 17, wherein the one or more tumor cells are isolated directly from a non-removed tumor, from a tumor cell biopsy or from a tumor that is surgically removed.

24. The method of claim 17, wherein the one or more tumor cells are imaged by confocal microscopy.

25. The method of claim 17, wherein the one or more tumor cells are from a cancer selected from the group consisting of breast cancer, prostate cancer, lung cancer, bladder cancer, pancreatic cancer, brain cancer, liver cancer, testicular cancer, skin cancer, colon cancer, ovarian cancer, cervical cancer, and uterine cancer.

26. The method of claim 17, wherein the cells are isolated from the tumor within 48 hours of imaging.

27. The method of claim 17, wherein the cells have not undergone more than three doublings since isolation up to the point of imaging the cells.

28. The method of claim 17, further comprising administering to the subject an effective amount of a candidate drug that inhibits microtentacle formation and/or stability to treat the cancer.

29. A method for determining the stem cell potential of tumor cells from a cancer subject comprising:
i) obtaining one or more live primary tumor cells that has been isolated by dissociation ex vivo from a solid tumor from the subject;
ii) imaging the one or more live primary tumor cells; and
iii) scoring the one or more imaged cells for microtentacles to determine the stem cell potential of the tumor cell.

30. The method of claim 29, wherein the scoring comprises determining whether the one or more cells comprise two or more protrusions longer than the cell radius, wherein the one or more cells comprising two or more protrusions longer than the cell radius have a greater stem cell potential than cells having fewer than two protrusions longer than the cell radius.

31. The method of claim 29, wherein the one or more tumor cells are isolated directly from a non-removed tumor, from a tumor cell biopsy or from a tumor that is surgically removed.

32. The method of claim 29, wherein the one or more tumor cells are imaged by confocal microscopy.

33. The method of claim 29, wherein the one or more tumor cells are from a cancer selected from the group consisting of breast cancer, prostate cancer, lung cancer, bladder cancer, pancreatic cancer, brain cancer, liver cancer, testicular cancer, skin cancer, colon cancer, ovarian cancer, cervical cancer, and uterine cancer.

34. The method of claim 29, wherein the cells are isolated from the tumor within 48 hours of imaging.

35. The method of claim 29, wherein the cells have not undergone more than three doublings since isolation up to the point of imaging the cells.

36. The method of claim 29, further comprising administering to the subject an effective amount of a drug to treat cancer.

* * * * *